US012655205B2

(12) United States Patent
Vijayendran et al.

(10) Patent No.: US 12,655,205 B2
(45) Date of Patent: Jun. 16, 2026

(54) ANTIBODIES AND ASSAYS FOR CCL14

(71) Applicant: bioMerieux, Inc., Salt Lake City, UT (US)

(72) Inventors: Ravi A. Vijayendran, San Diego, CA (US); Hua Wang, San Diego, CA (US)

(73) Assignee: bioMerieux, Inc., Salt Lake City, UT (US)

( * ) Notice: Subject to any disclaimer, the term of this patent is extended or adjusted under 35 U.S.C. 154(b) by 0 days.

(21) Appl. No.: 18/390,942

(22) Filed: Dec. 20, 2023

(65) Prior Publication Data

US 2024/0124569 A1 Apr. 18, 2024

Related U.S. Application Data

(62) Division of application No. 16/958,072, filed as application No. PCT/US2018/068000 on Dec. 28, 2018, now Pat. No. 11,891,439.

(60) Provisional application No. 62/611,510, filed on Dec. 28, 2017.

(51) Int. Cl.

| *C07K 16/24* | (2006.01) |
|---|---|
| *C07K 16/00* | (2006.01) |
| *C07K 16/18* | (2006.01) |
| *G01N 33/543* | (2006.01) |
| *G01N 33/68* | (2006.01) |

(52) U.S. Cl.
CPC .............. *C07K 16/24* (2013.01); *C07K 16/00* (2013.01); *C07K 16/18* (2013.01); *G01N 33/543* (2013.01); *G01N 33/54388* (2021.08); *G01N 33/6863* (2013.01); *C07K 2317/20* (2013.01); *C07K 2317/34* (2013.01); *C07K 2317/54* (2013.01); *C07K 2317/55* (2013.01); *C07K 2317/565* (2013.01); *C07K 2317/567* (2013.01); *C07K 2317/62* (2013.01)

(58) Field of Classification Search
None
See application file for complete search history.

(56) References Cited

U.S. PATENT DOCUMENTS

| 4,477,575 | A | 10/1984 | Vogel et al. |
|---|---|---|---|
| 5,166,051 | A | 11/1992 | Killeen et al. |
| 5,413,923 | A | 5/1995 | Kucherlapati et al. |
| 5,480,792 | A | 1/1996 | Buechler et al. |
| 5,525,524 | A | 6/1996 | Buechler et al. |
| 5,530,101 | A | 6/1996 | Queen et al. |
| 5,545,806 | A | 8/1996 | Lonberg et al. |
| 5,569,825 | A | 10/1996 | Lonberg et al. |
| 5,571,698 | A | 11/1996 | Ladner et al. |
| 5,585,089 | A | 12/1996 | Queen et al. |
| 5,625,126 | A | 4/1997 | Lonberg et al. |
| 5,631,171 | A | 5/1997 | Sandstrom et al. |
| 5,633,425 | A | 5/1997 | Lonberg et al. |

| 5,661,016 | A | 8/1997 | Lonberg et al. |
|---|---|---|---|
| 5,679,526 | A | 10/1997 | Buechler et al. |
| 5,693,761 | A | 12/1997 | Queen et al. |
| 5,693,762 | A | 12/1997 | Queen et al. |
| 5,807,715 | A | 9/1998 | Morrison et al. |
| 5,814,318 | A | 9/1998 | Lonberg et al. |
| 5,821,337 | A | 10/1998 | Carter et al. |
| 5,824,799 | A | 10/1998 | Buechler et al. |
| 5,851,776 | A | 12/1998 | Valkirs |
| 5,859,205 | A | 1/1999 | Adair et al. |
| 5,885,527 | A | 3/1999 | Buechler |
| 5,922,615 | A | 7/1999 | Nowakowski et al. |
| 5,939,272 | A | 8/1999 | Buechler et al. |
| 5,939,598 | A | 8/1999 | Kucherlapati et al. |
| 5,947,124 | A | 9/1999 | Buechler et al. |
| 5,955,377 | A | 9/1999 | Maul et al. |
| 5,985,579 | A | 11/1999 | Buechler et al. |
| 6,019,944 | A | 2/2000 | Buechler |
| 6,054,297 | A | 4/2000 | Carter et al. |
| 6,057,098 | A | 5/2000 | Buechler et al. |
| 6,113,855 | A | 9/2000 | Buechler |
| 6,143,576 | A | 11/2000 | Buechler |
| 6,180,370 | B1 | 1/2001 | Queen et al. |
| 6,391,265 | B1 | 5/2002 | Buechler et al. |
| 6,407,213 | B1 | 6/2002 | Carter et al. |
| 6,797,492 | B2 | 9/2004 | Daugherty et al. |
| 6,946,292 | B2 | 9/2005 | Kanda et al. |
| 7,125,493 | B2 | 10/2006 | Wang et al. |
| 7,214,775 | B2 | 5/2007 | Hanai et al. |
| 7,657,380 | B2 | 2/2010 | Lazar et al. |
| 11,891,439 | B2 * | 2/2024 | Vijayendran .... G01N 33/54388 |
| 2005/0118586 | A1 | 6/2005 | Bejanin et al. |
| 2008/0085241 | A1 | 4/2008 | Stassar et al. |
| 2011/0059107 | A1 | 3/2011 | Allison et al. |
| 2012/0301488 | A1 | 11/2012 | Zhang et al. |
| 2013/0108640 | A1 | 5/2013 | Allison et al. |
| 2013/0203079 | A1 | 8/2013 | Goodman et al. |
| 2015/0030586 | A1 | 1/2015 | Warren et al. |

(Continued)

FOREIGN PATENT DOCUMENTS

| CN | 102597001 A | 7/2012 |
|---|---|---|
| CN | 102782148 A | 11/2012 |

(Continued)

OTHER PUBLICATIONS

Shijing et al., "Clinical Immunological Testing," Chinese Medicine Publishing House, 2015, 11 pp (including English translation).
Official action issued Feb. 1, 2024, in Chinese Application No. 201880088190.3.
Baldridge et al., "Monophosphoryl Lipid A (MPL) Formulations for the Next Generation of Vaccines," Methods, 1999, 19:103-107.
Bieg et al., "GAD65 and Insulin B Chain Peptide (9-23) are not Primary Autoantigens in the Type 1 Diabetes Syndrome pf the BB Rat," Autoimmunity, 1999, 31:15-24.
Bitter et al., "Expression and Secretion Vectors for Yeast," Methods Enzymol, 1987, 153:516-544.
Brüggemann et al., "Production of human antibody repertoiries in transgenic mice," Curr Opin Biotechnol, Aug. 1997, 8(4):455-458.
Carter et al., "Humanization of an anti-p185HER2 antibody for human cancer therapy," Proc Natl Acad Sci USA, May 1992, 89:4285-4289.

(Continued)

*Primary Examiner* — Nora M Rooney

(57) ABSTRACT

The invention provides CCL14 antibodies.

15 Claims, 3 Drawing Sheets

Specification includes a Sequence Listing.

(56) References Cited

U.S. PATENT DOCUMENTS

| | | |
|---|---|---|
| 2017/0226228 A1 | 8/2017 | Desir et al. |
| 2018/0086846 A1 | 3/2018 | Wiltzius et al. |
| 2018/0209990 A1 | 7/2018 | Anderberg et al. |
| 2019/0339289 A1 | 11/2019 | Kampf et al. |
| 2021/0061900 A1 | 3/2021 | Vijayendran et al. |

FOREIGN PATENT DOCUMENTS

| | | |
|---|---|---|
| CN | 112041341 A | 12/2020 |
| WO | WO 1992/11018 | 7/1992 |
| WO | WO 1996/33735 | 10/1996 |
| WO | WO 1996/34096 | 10/1996 |
| WO | WO 1998/24893 | 6/1998 |
| WO | WO 2012/177595 | 12/2012 |
| WO | WO 2011/025962 | 1/2013 |
| WO | 2014/003744 A1 | 1/2014 |
| WO | 2015/164330 A1 | 10/2015 |
| WO | 2016/064877 A2 | 4/2016 |
| WO | 2017/004151 A1 | 1/2017 |
| WO | 2018/132702 A1 | 7/2018 |
| WO | 2019/133902 A2 | 7/2019 |

OTHER PUBLICATIONS

Crouse et al., "Expression and Amplification of Engineered Mouse Dihydrofolate Reductase Minigenes," Mol Cell Biol, Feb. 1983, 3:257-266.

Cwirla et al., "Peptides on phage: A vast library of peptides for identifying ligands," Proc Natl Acad Sci USA, Aug. 1990, 87:6378-6382.

De Pascalis et al., "Grafting of 'Abbreviated' Complementarity-Determining Regions Containing Specificity-Determining Residues Essential for Ligand Contact to Engineer a Less Immunogenic Humanized Monoclonal Antibody," J Immunol, 2002, 169(6):3076-3084.

Devlin et al., "Random Peptide Libraries: A Source of Specific Protein Binding Molecules," Science, 1990, 249:404-406.

Eton et al., "Active Immunotherapy with Ultraviolet B-Irradiated Autologous Whole Melanoma Cells plus Detox in Patients with Metastatic Melanoma," Clin Cancer Res, Mar. 1998, 4:619-627.

Fischer et al., "A readers' guide to the interpretation of diagnostic test properties: clinical example of sepsis," Intensive Care Med, 2003, 29:1043-1051.

Geysen et al., "Use of peptide synthesis to probe viral antigens for epitopes to a resoluton of a single amino acid," Proc Natl Acad Sci USA, Jul. 1984, 81:3998-4002.

Goel et al., "Plasticity within the Antigen-Combining Site May Manifest as Molecular Mimicry in the Humoral Immune Response," J Immunol, 2004, 173:7358-7367.

Gorman et al., "Reshaping a therapeutic CD4 antibody," Proc Natl Acad Sci USA, May 1991, 88:4181-4185.

Griffiths et al., "Strategies for selection of antibodies by phage display," Curr Opin Biotechnol. 1998, 9:102-108.

Gupta et al., "Adjuvants for human vaccines—current status, problems and future prospects," Vaccine, 1995, 13(14):1263-1276.

Inouye et al.,"Up-promoter mutations in the Ipp gene of Escherichia coli," Nucleic Acids Res, 1985, 13(9):3101-3110.

Johnson et al., "3-0-Desacyl Monophosphoryl Lipid A Derivatives: Synthesis and Immunostimulant Activities," J Med Chem, 1999, 42:4640-4649.

Jones et al., "Replacing the complementarity-determining regions in a human antibody with those from a mouse," Nature, May 29-Jun. 4, 1986, 321:522-525.

Kahn et al., "Adjustable Locks and Flexible Keys: Plasticity of Epitote-Paratope Interactions in Germline Antibodies," J Immunol, 2014, 192:5398-5405.

Kohler, "Immunoglobulin chain loss in hybridoma lines," Proc Natl Acad Sci USA, Apr. 1980, 77(4):2197-2199.

Krauss et al., "Specificity grafting of human antibody frameworks selected from a phage display library: generation of a highly stable humanized anti-CD22 single-chain Fv fragment," Protein Eng, 2003, 16(10):753-759.

Lodmell et al., "DNA vaccination of mice against rabies virus: effects of the route of vaccination and the adjuvant monophosphoryl lipid A (MPL)," Vaccine, 2000, 18:1059-1066.

Logan et al., "Adenovirus tripartite leader sequence enhances translation of mRNAs late after infection," Proc Natl Acad Sci USA, Jun. 1984, 81:3655-3659.

Lonberg et al., "Human Antibodies From Transgenic Mice," Intern Rev Immunol, 1995, 13:65-93.

Lowy et al., "Isolation of Transforming DNA: Cloning the Hamster aprt Gene," Cell, Dec. 1980, 22:817-823.

Maccallum et al., "Antibody-antigen Interactions: Contact Analysis and Binding Site Topography," J.Mol. Biol., 1996, 262:732-745.

Mariuzza et al., "The Structural Basis of Antigen-Antibody Recognition," Ann. Rev. Biophys. Biophys. Chem., 1987, 16:139-159.

Morgan et al., "Human Gene Therapy," Annu Rev Biochem, 1993, 62:191-217.

Mulligan, "The Basic Science of Gene Therapy," Science, May 14, 1993, 260:926-932.

Mulligan et al., "Selection for animal cells that express the Escherichia coli gene coding for xanthine-guanine phosphoribasyltransferase, Proc Natl Acad Sci USA," Apr. 1981, 78(4):2072-2076.

Nelson et al., "A computer program for calculating antibody affinity constants," Comput Methods Programs Biomed, 1988, 27:65-68.

O'Connor et al., "Humanization of an antibody against human protein C and calcium-dependence involving framework residues," Protein Eng, 1998, 11(4):321-328.

O'Hare et al., "Transformation of mouse fibroblasts to methotrexate resistance by a recombinant plasmid expressing a prokaryotic dihydrofolate reductase," Proc Natl Acad Sci USA, Mar. 1981, 78(3):1527-1531.

Piche-Nicholas et al., "Changes in complementarity-determining regions significantly alter IgG binding to the neonatal Fc receptor (FcRn) and pharmacokinetics," MABS, 2018, 10(1):81-94.

Poosarla et al., "Computational De Novo Design of Anitbodies Binding to a Peptide With High Affinity," Biotechnology and Bioengineering, 2017, 114(6):1331-1342.

Presta et al., "Humanization of an Anti-Vascular Endothelial Growth Factor Monoclonal Antibody for the Therapy of Solid Tumors and Other Disorders," Cancer Res, Oct. 15, 1997, 57:4593-4599.

Proudfoot, "Transcriptional interference and termination between duplicated alpha-globin gene constructs suggests a novel mechanism for gene regulation," Nature, 1986, 322:562-565.

Queen et al., "A humanized antibody that binds to the interleukin 2 receptor," Proc Natl Acad Sci USA, Dec. 1989, 86:10029-10033.

Rader et al., "A phage display approach for rapid antibody humanization: Designed combinatorial V gene libraries," Proc Natl Acad Sci USA, Jul. 1998, 95:8910-8915.

Riechmann et al., "Reshaping human antibodies for therapy," Nature, Mar. 1988, 332:323-327.

Roguska et al., "Humanization of murine monoclonal antibodies through variable domain resurfacing," Proc Natl Acad Sci USA, Feb. 1994, 91:969-973.

Roque et al., "Antibodies and Genetically Engineered Related Molecules: Production and Purification," Biotechnol Prog, 2004, 20:639-654.

Rosok et al., "A Combinatorial Library Strategy for the Rapid Humanization of Anticarcinoma BR96 Fab," J Biol Chem, Sep. 13, 1996, 271(37)22611-22618.

Rossi et al., "A Comparative Study Between a Novel Category of Immunoreagents and the Corresponding Mouse Monoclonal Antibodies," Am J Clin Pathol, 2005, 124:295-302.

Rudikoff et al., "Single amino acid substitution altering antigen-binding specificity," Proc. Natl. Acad. Sci. USA, 1982, 79:1979-1983.

Rump et al., "An initial investigation into endothelial CC chemokine expression in the human rheumatoid synovium," Cytokine, 2017, 97:133-140.

Ruther et al., "Easy identification of cDNA clones," Embo J, 1983, 2(10):1791-1794.

(56)                References Cited

OTHER PUBLICATIONS

Santerre et al., "Expression of prokaryotic genes for hygromycin B and G418 resistance as dominant-selection markers in mouse L cells," Gene, 1984, 30:147-156.

Scott et al., "Searching for Peptide Ligands with an Epitope Library," Science, 1990, 249:386-390.

Shinkawa et al., "The Absence of Fucose but Not the Presence of Galactose or Bisecting N-Acetylglucosamine of Human IgG1 Complex-type Oligosaccharides Shows the Critical Role of Enhancing Antibody-dependent Cellular Cytotoxicity," Jan. 31, 2003, J Biol Chem, 278(5):3466-3473.

Szybalska et al., "Genetics of Human Cell Lines, IV. DNA-Mediated Heritable Transformation of a Biochemical Trait," Proc Natl Acad Sci USA, 1962, 48:2026-2034.

Tachibana et al., "Altered reactivity of immunoglobulin produced by human-human hybridoma cells transfected by pSV2-neo gene," Cytotechnology, 1991, 6:219-226.

Tan et al., "Superhumanized Antibodies: Reduction of Immunogenic Potential by Complementarity-Determining Region Grafting with Human Germline Sequences: Application to an Anti-CD28," J Immunol, 2002, 169:1119-1125.

Tolstoshev, "Gene Therapy, Concepts, Current Trials and Future Directions," Annu Rev Pharmacol Toxicol, 1993, 33:573-596.

Tsurushita et al., "Humanization of Monoclonal Antibodies," Molecular Biology of B Cells, 2004:533-545.

UniProtKB Q16627, "(CCL14_Human)," Nov. 1, 1997.

Van Erp et al., "Application of a Sol Particle Immunoassay to the Determination of Affinity Constants of Monoclonal Antibodies," J Immunoassay, 1991, 12(3):425-443.

Van Heeke et al., "Expression of Human Asparagine Synthetase in *Escherichia coli*," J Biol Chem, Apr. 5, 1989, 264(10):5503-5509.

Verhoeyen et al., "Reshaping Human Antibodies: Grafting an Antilysozyme Activity," Science, 1988, 239:1534-1536.

Ward et al., "Binding activities of a repertoire of single immunoglobulin variable domains secreted from *Escherichia coli*," Nature, Oct. 12, 1989, 341:544-546.

Wigler et al., "Transfer of Purified Herpes Virus Thymidine Kinase Gene to Cultured Mouse Cells," Cell, May 1977, 11:223-232.

Wigler et al., "Transformation of mammalian cells with an amplifiable dominant-acting gene," Proc Natl Acad Sci USA, Jun. 1980, 77(6):3567-3570.

Wilson et al., "Simplified conjugation chemistry for coupling peptides to F(ab') fragments: autologous red cell agglutination assay for HIV-1 antibodies," J Immunol Methods, 1994, 175:267-273.

Wu et al., "Humanization of a Murine Monoclonal Antibody by Simultaneous Optimization of Framework and CDR Residues," J Mol Biol, 1999, 294:151-162.

Yarmush et al., "Coupling of antibody-binding fragments to solid-phase supports: site-directed binding of F(ab')2 fragments," J Biochem Biophys Methods, 1992, 25:285-297.

Official action issued Jun. 21, 2023, in Chinese Application No. 201880088190.3.

Extended European Search Report issued Dec. 6, 2021, in European Patent Application No. 18893753.6.

Official action issued Jul. 11, 2023, in European Application No. 18893753.6.

Official action issued Dec. 1, 2022, in European Application No. 18893753.6.

Partial Supplementary European Search Report issued Aug. 4, 2021, in European Patent Application No. 18893753.6.

International Search Report and Written Opinion issued Aug. 27, 2019, in PCT Application No. PCT/US2018/068000.

Official action issued Nov. 22, 2022, in Japanese Application No. 2022-555739.

Extended European Search Report issued Oct. 4, 2023 in European Patent Application No. 20834440.8.

GenBank: AAA31367.1, "immunoglobulin heavy chain, partial [Oryctolagus cuniculus]," Jun. 2, 1994.

International Preliminary Report on Patentability dated Dec. 28, 2021 issued in PCT/US2020/040520.

International Preliminary Report on Patentability received for PCT Patent Application No. PCT/US2018/068000, mailed on Jul. 9, 2020, 8 pages.

International Search Report and Written Opinion dated Oct. 14, 2020 issued in PCT/US2020/040520.

Li, "Chemokines CCL2, 3, 14 regulate macrophage bone marrow homing, proliferation and polarization in multiple myeloma," Zhejiang University School of Medicine, May 1, 2015, 10:1-106, English abstract.

Official action issued Dec. 14, 2023, in Chinese Patent Application No. 202080060781. 7.

Official action issued Feb. 5, 2024, in Canadian Patent Application No. 3145667.

Official action issued Jul. 11, 2023, in European Patent Application No. 20834440.8.

Official action issued Jun. 1, 2023, in Chinese Patent Application No. 202080060781. 7.

R&D Systems: "Human CCL 14/HCC-1 /HCC-3 Antibody MAB3241", Jul. 2, 2018, XP93059968, Retrieved from the Internet: URL:https://resources.rndsystems.com/pdfs/datasheets/mab3241.pdf?

* cited by examiner

```
2H3    METGLRWLLLVAVLKGVQCQEQLKESGGGLVQPGGSLKLSCKASGFAFSS-DYMSWVRQA
25H2   METGLRWLLLVAVLKGVQCQS-LEESGGDLVKPGASLTLTCTASRFDFSSAYYMCWVRQA
3H1    METGLRWLLLVAVLKGVQCQS-VRESEGGLFKPADTLTLTCTVSGFSLSS-DAISWVRQA
12H2   METGLRWLLLVAVLKGVQCQS-VRESEGGLFKPADTLTLTCTVSGFSLSS-DAISWVRQA
31H1   METGLRWLLLVAVLKGVQCQS-VRESEGGLFKPADTLTLTCTVSGFSLSS-DAISWVRQA
4H1    METGLRWLLLVAVLKGVQCQS-VKESEGGLFKPADTLTLTCTVSGFSLSS-FAINWVRQA
10H3   METGLRWLLLVAVLKGVQCQS-VKESEGGLFKPADTLTLTCTVSGFSLSS-YAINWVRQA
17H2   METGLRWLLLVAVLKGVQCQS-VKESEGGLFKPADTLTLTCTVSGFSLSS-YAINWVRQA
18H1   METGLRWLLLVAVLKGVQCQS-VKESEGGLFKPADTLTLTCTVSGFSLSS-YAINWVRQA
19H2   METGLRWLLLVAVLKGVQCQS-VKESEGGLFKPADTLTLTCTVSGFSLSS-FAINWVRQA
                                                          CDR1
```

```
2H3    PGKGLEWIGYIDPIF-GSTAYASWVNGRFTISSHNAQNTLYLHLNSLTAADTATYFCARD
25H2   PGKGLEWIACIYAGSSGGTYYATWAKGRFTISKT-SSTTVTLQLTSLTAADTATYFCAGS
3H1    PGNGLEWIGAID--FGGSAYYASWAKSRSTITRNTNENTVTLKMTSLTAADTATYFCARS
12H2   PGNGLEWIGAID--FGGSAYYASWAKSRSTITRNTNENTVTLKMTSLTAADTATYFCARS
31H1   PGNGLEWIGAID--FGGSAYYASWAKSRSTITRNTNENTVTLKMTSLTAADTATYFCARS
4H1    PGEGLEYIGWIS--DVGTAYYASWAKSRSTITRNTDENTATLKMTSLTAADTATYFCAGG
10H3   PGEGLEYIGWIS--DVGTAYYASWAKSRSTITRNTDENTVTLKMTSLTAADTATYFCAGG
17H2   PGEGLEYIGWIS--DVGTAYYASWAKSRSTITRNTDENTVTLKMTSLTAADTATYFCAGG
18H1   PGEGLEYIGWIS--DVGTAYYASWAKSRSTITRNTDENTVTLKMTSLTAADTATYFCAGG
19H2   PGEGLEYIGWIS--DVGTAYYASWAKSRSTITRNADENTVTLKMTSLTAADTATYFCAGG
                CDR2
```

```
2H3    DKDYSSGWGGYFNLWGQGTLVTVSSGQPK
25H2   STGNSRG--SYFNLWGQGTLVTVSSGQPK
3H1    SP-SFGI-VDRLDLWGQGTLVTVSSGQPK
12H2   SP-SFGI-VDRLDLWGQGTLVTVSSGQPK
31H1   SP-SFGI-VDRLDLWGQGTLVTVSSGQPK
4H1    GDGSYSN-YWVSDIWGQGTLVTVSSGQPK
10H3   GDGSYSN-YWVSDIWGQGTLVTVSSGQPK
17H2   GDGSYSN-YWVSDIWGQGTLVTVSSGQPK
18H1   GDGSYSN-YWVSDIWGQGTLVTVSSGQPK
19H2   GDGSYSN-YWVSDIWGQGTLVTVSSGQPK
       CDR3
```

FIG. 1

```
25K1   MDTRAPTQLLGLLLLWLPGATFAQ-VLTQTPSPVSAAVGGTVTINCQSS QSVYDNNWLAW
2K1    MDTRAPTQLLGLLLLWLPGARCGAIVMTQTPASVEAAVGGTVTIKCQAS QSI---NSYLAW
3K1    MDTRAPTQLLGLLLLWLPGARCAV-VLTQTASPVSAPVGGTVTIKCQAS EDI---DSYLAW
12K1   MDTRAPTQLLGLLLLWLPGARCAV-VLTQTASPVSAPVGGTVTIKCQAS EDI---DSYLAW
31K1   MDTRAPTQLLGLLLLWLPGAKCAV-VLTQTASPVSAPVGGTVTIKCQAS EDI---DSYLAW
4K3    MDTRAPTQLLGLLLLWLPGARCAV-VLTQTASPVSAPVGGTVTVKCQAS QTI---NNRLAW
19K3   MDTRAPTQLLGLLLLWLPGARCAV-VLTQTASPVSAPVGGTVTVKCQAS QTI---NNRLAW
17K1   MDTRAPTQLLGLLLLWLPGARCAV-VLTQTASPVSAPVGGTVTVKCQAS QTI---NSRLAW
18K1   MDTRAPTQLLGLLLLWLPGARCAV-VLTQTASPVSAPVGGTVTVKCQAS QTI---NSRLAW
10K1   MDTRAPTQLLGLLLLWLPGARCAV-VLTQTPSLVSAPVGGTVTVKCRAS QTI---NSRLAW
                                                          CDR1
```

```
25K1   YQQKLGQPPKLVIY DASKLASGVPSRFKGSGSGTHFTLTISELQCDDSATYYC QGEY---
2K1    YQQKPGQPPRLLIY EASTLASGVPSRFKGSGSGTQFTLTISDLECADAATYYC QTYYYSV
3K1    YQQKPGQPPKLLIY DVEDLSSGVPSRFKGSGSGTEFTLTISDLECADAATYYC QSYYYVL
12K1   YQQKPGQPPKLLIY DVEDLSSGVPSRFKGSGSGTEFTLTISDLECADAATYYC QSYYYVL
31K1   YQQKPGQPPKLLIY DVEDLSSGVPSRFKGSGSGTEFTLTISDLECADAATYYC QSYYYVL
4K3    YQQKQGQPPKLLIY EASKLASGVPSRFKGSGSGTEYTLTIRGVECADAATYSC QEY----
19K3   YQQKQGQPPKLLIY EASKLASGVPSRFKGSGSGTEYTLTIRGVECADAATYSC QEY----
17K1   YQQKQGQPPKLLIY EASTLASGVPSRFKGSGSGTEYTLTIRGVECADAATYSC QEY----
18K1   YQQKQGQPPKLLIY EASTLASGVPSRFKGSGSGTEYTLTIRGVECADAATYSC QEY----
10K1   YQQKQGQPPKLLIY EASKLASGVPSRFKGSGSGTEYTLTIRGVECADAATYSC QEY----
                    CDR2                                       CDR3
```

```
25K1   ----SDIWGFGGGTEVVVKGDPV
2K1    DSS-VGSNAFGGGTEVVVKGDPV
3K1    GTTSTDHNSFGGGTEVVVKGDPV
12K1   GTTSTDHNSFGGGTEVVVKGDPV
31K1   GTTSTDHNSFGGGTEVVVKGDPV
4K3    ----ADENIFGGGTEVVVKGDPV
19K3   ----ADENIFGGGTEVVVKGDPV
17K1   ----ADENIFGGGTEVVVKGDPV
18K1   ----ADENIFGGGTEVVVKGDPV
10K1   ----ADENIFGGGTEVVVKGDPV
       CDR3
       (continued)
```

FIG. 2

ANTIBODIES AND ASSAYS FOR CCL14

The present application is a divisional application of U.S. patent application Ser. No. 16/958,072, filed Jun. 25, 2020, which is a U.S. National Phase Entry of International Patent Application No. PCT/US2018/068000, filed Dec. 28, 2018, which claims the benefit of U.S. Provisional Application No. 62/611,510, filed Dec. 28, 2017, from which priority is claimed and which is hereby incorporated by reference in its entirety including all tables, figures, and claims.

SEQUENCE LISTING

This application contains a Sequence Listing which has been submitted in XML format and is hereby incorporated by reference in its entirety. Said XML copy, created on Dec. 19, 2023, is named AST_M_0006_PCT_Sequence_Listing.xml and is 42,177 bytes in size.

BACKGROUND

The following discussion of the background of the invention is merely provided to aid the reader in understanding the invention and is not admitted to describe or constitute prior art to the present invention.

C-C motif chemokine 14 (CCL14; SWISS-PROT Entry Q16627, also known as HCC-1, NCC-2, and SCYA14) is a small cytokine belonging to the CC chemokine family. It is also known as HCC-1. It is produced as a 93 residue protein precursor that is processed to generate a mature active protein containing 74 amino acids (residues 20-93) that and is 46% identical in amino acid composition to CCL3 and CCL4. This chemokine is expressed in various tissues including spleen, bone marrow, liver, muscle, and gut. CCL14 activates monocytes, but does not induce their chemotaxis. Human CCL14 is located on chromosome 17 within a cluster of other chemokines belonging to the CC family.

SUMMARY

It is an object of the invention to provide antibodies which bind CCL14. Such antibodies can find use in immunoassays with improved clinical performance, particularly when used in the evaluation of renal injuries, and in therapeutic methods in which CCL14 binding is desired.

In a first aspect, the present invention relates to antibodies or antigen binding fragments thereof that binds to human CCL14, wherein the antibody or antigen binding fragment comprises:

(i) a heavy chain variable region comprising
    a CDR1, CDR2, and CDR3 sequence from SEQ ID NO: 1,
    a CDR1, CDR2, and CDR3 sequence from SEQ ID NO: 3,
    a CDR1, CDR2, and CDR3 sequence from SEQ ID NO: 5,
    a CDR1, CDR2, and CDR3 sequence from SEQ ID NO: 7,
    a CDR1, CDR2, and CDR3 sequence from SEQ ID NO: 9,
    a CDR1, CDR2, and CDR3 sequence from SEQ ID NO: 11,
    a CDR1, CDR2, and CDR3 sequence from SEQ ID NO: 13, a CDR1, CDR2, and CDR3 sequence from SEQ ID NO: 15,
    a CDR1, CDR2, and CDR3 sequence from SEQ ID NO: 17, or
    a CDR1, CDR2, and CDR3 sequence from SEQ ID NO: 19; and
  (ii) a light chain variable region comprising
    a CDR1, CDR2, and CDR3 sequence from SEQ ID NO: 2,
    a CDR1, CDR2, and CDR3 sequence from SEQ ID NO: 4,
    a CDR1, CDR2, and CDR3 sequence from SEQ ID NO: 6,
    a CDR1, CDR2, and CDR3 sequence from SEQ ID NO: 8,
    a CDR1, CDR2, and CDR3 sequence from SEQ ID NO: 10,
    a CDR1, CDR2, and CDR3 sequence from SEQ ID NO: 12,
    a CDR1, CDR2, and CDR3 sequence from SEQ ID NO: 14,
    a CDR1, CDR2, and CDR3 sequence from SEQ ID NO: 16,
    a CDR1, CDR2, and CDR3 sequence from SEQ ID NO: 18, or
    a CDR1, CDR2, and CDR3 sequence from SEQ ID NO: 20.

In certain embodiments, the antibody or antigen binding fragment comprises one the following heavy chain CDR/light chain CDR pairs:

a heavy chain variable region comprising a CDR1, CDR2, and CDR3 sequence from SEQ ID NO: 1, and a light chain variable region comprising a CDR1, CDR2, and CDR3 sequence from SEQ ID NO: 2 (2H3/2K1), a heavy chain variable region comprising a CDR1, CDR2, and CDR3 sequence from SEQ ID NO: 3, and a light chain variable region comprising a CDR1, CDR2, and CDR3 sequence from SEQ ID NO: 4 (3H1/3K1), a heavy chain variable region comprising a CDR1, CDR2, and CDR3 sequence from SEQ ID NO: 5, and a light chain variable region comprising a CDR1, CDR2, and CDR3 sequence from SEQ ID NO: 6 (4H1/4K3), a heavy chain variable region comprising a CDR1, CDR2, and CDR3 sequence from SEQ ID NO: 7, and a light chain variable region comprising a CDR1, CDR2, and CDR3 sequence from SEQ ID NO: 8 (10H3/10K1), a heavy chain variable region comprising a CDR1, CDR2, and CDR3 sequence from SEQ ID NO: 9, and a light chain variable region comprising a CDR1, CDR2, and CDR3 sequence from SEQ ID NO: 10 (12H2/12K1), a heavy chain variable region comprising a CDR1, CDR2, and CDR3 sequence from SEQ ID NO: 11, and a light chain variable region comprising a CDR1, CDR2, and CDR3 sequence from SEQ ID NO: 12 (17H2/17K1), a heavy chain variable region comprising a CDR1, CDR2, and CDR3 sequence from SEQ ID NO: 13, and a light chain variable region comprising a CDR1, CDR2, and CDR3 sequence from SEQ ID NO: 14 (18H1/18K1), a heavy chain variable region comprising a CDR1, CDR2, and CDR3 sequence from SEQ ID NO: 15, and a light chain variable region comprising a CDR1, CDR2, and CDR3 sequence from SEQ ID NO: 16 (19H2/19K3), a heavy chain variable region comprising a CDR1, CDR2, and CDR3 sequence from SEQ ID NO: 17, and a light chain variable region comprising a CDR1, CDR2, and CDR3 sequence from SEQ ID NO: 18 (25H2/25K1), or a heavy chain variable region comprising a CDR1, CDR2, and CDR3 sequence from SEQ ID NO: 19, and a light chain variable region comprising a CDR1, CDR2, and CDR3 sequence from SEQ ID NO: 20 (31H1/31K1).

In certain embodiments, the antibody or antigen binding fragment comprises:

(i) a heavy chain variable region selected from the group consisting of SEQ ID NO: 1, 3, 5, 7, 9, 11, 13, 15, 17, and 19, or a corresponding heavy chain variable region having at least 90% sequence similarity to the framework region thereof; and (ii) a light chain variable region selected from the group consisting of SEQ ID NO: 2, 4, 6, 8, 10, 12, 14, 16, 18, and 20, or a corresponding light chain variable region having at least 90% sequence similarity to the framework region thereof.

In certain embodiments, the antibody or antigen binding fragment comprises one the following heavy chain/light chain pairs:

a heavy chain variable region of SEQ ID NO: 1 or a corresponding heavy chain variable region having at least 90% sequence similarity to the framework region thereof, and a light chain variable region of SEQ ID NO: 2 a corresponding light chain variable region having at least 90% sequence similarity to the framework region thereof (2H3/2K1).

a heavy chain variable region of SEQ ID NO: 3 or a corresponding heavy chain variable region having at least 90% sequence similarity to the framework region thereof, and a light chain variable region of SEQ ID NO: 4 a corresponding light chain variable region having at least 90% sequence similarity to the framework region thereof (3H1/3K1), a heavy chain variable region of SEQ ID NO: 5 or a corresponding heavy chain variable region having at least 90% sequence similarity to the framework region thereof, and a light chain variable region of SEQ ID NO: 6 a corresponding light chain variable region having at least 90% sequence similarity to the framework region thereof (4H1/4K3), a heavy chain variable region of SEQ ID NO: 7 or a corresponding heavy chain variable region having at least 90% sequence similarity to the framework region thereof, and a light chain variable region of SEQ ID NO: 8 a corresponding light chain variable region having at least 90% sequence similarity to the framework region thereof (10H3/10K1), a heavy chain variable region of SEQ ID NO: 9 or a corresponding heavy chain variable region having at least 90% sequence similarity to the framework region thereof, and a light chain variable region of SEQ ID NO: 10 a corresponding light chain variable region having at least 90% sequence similarity to the framework region thereof (12H2/12K1), a heavy chain variable region of SEQ ID NO: 11 or a corresponding heavy chain variable region having at least 90% sequence similarity to the framework region thereof, and a light chain variable region of SEQ ID NO: 12 a corresponding light chain variable region having at least 90% sequence similarity to the framework region thereof (17H2/17K1), a heavy chain variable region of SEQ ID NO: 13 or a corresponding heavy chain variable region having at least 90% sequence similarity to the framework region thereof, and a light chain variable region of SEQ ID NO: 14 a corresponding light chain variable region having at least 90% sequence similarity to the framework region thereof (18H1/18K1), a heavy chain variable region of SEQ ID NO: 15 or a corresponding heavy chain variable region having at least 90% sequence similarity to the framework region thereof, and a light chain variable region of SEQ ID NO: 16 a corresponding light chain variable region having at least 90% sequence similarity to the framework region thereof (19H2/19K3), a heavy chain variable region of SEQ ID NO: 17 or a corresponding heavy chain variable region having at least 90% sequence similarity to the framework region thereof, and a light chain variable region of SEQ ID NO: 18 a corresponding heavy chain variable region having at least 90% sequence similarity to the framework region thereof (25H2/25K1), or a heavy chain variable region of SEQ ID NO: 19 or a corresponding heavy chain variable region having at least 90% sequence similarity to the framework region thereof, and a light chain variable region of SEQ ID NO: 20 a corresponding light chain variable region having at least 90% sequence similarity to the framework region thereof (31H1/31K1).

Within the description of the present invention, at least 90% sequence similarity should be understood to include at least 95%, and more preferably at least 99% sequence similarity. In this context, "sequence similarity" is based on the extent of identity combined with the extent of conservative changes. The percentage of "sequence similarity" is the percentage of amino acids or nucleotides which is either identical or conservatively changed viz. "sequence similarity"=percent sequence identity)+percent conservative changes). Thus, for the purpose of this invention "conservative changes" and "identity" are considered to be species of the broader term "similarity". Thus, whenever the term sequence "similarity" is used it embraces sequence "identity" and "conservative changes". According to certain embodiments the conservative changes are disregarded and the percent sequence similarity refers to percent sequence identity. In certain embodiments, the changes in a sequence permitted by the referenced percent sequence identity are all or nearly all conservative changes; that is, when a sequence is 90% identical, the remaining 10% are all or nearly all conservative changes. The term "nearly all" in this context refers to at least 75% of the permitted sequence changes are conservative changes, more preferably at least 85%, still more preferably at least 90%, and most preferably at least 95%.

Antibodies for use in the claimed methods may be obtained from a variety of species. For example, the antibodies of the present invention may comprise immunoglobulin sequences which are rabbit, mouse, rat, guinea pig, chicken, goat, sheep, donkey, human, llama or camelid sequences, or combinations of such sequences (so-called chimeric antibodies). Such antibodies may also be monoclonal or polyclonal. Antibodies for use in the present invention may be identified by their performance in immunoassays, and then further characterized by epitope mapping in order to understand the epitopes which are relevant to that performance. Preferred are rabbit antibodies or humanized versions derived from rabbit antibodies.

Such antibodies may be conjugated to a signal development element or immobilized on a solid support. In addition, such antibodies may be used in a number of competitive and sandwich assay formats. In an example of a sandwich assay, a first antibody (detectably labeled) and a second antibody (immobilized at a predetermined zone of a test device) form sandwich complexes with CCL14 in the sample at a predetermined zone of a test device. In sandwich assays, the first and second antibodies can be the same (particularly when polyclonal antibodies are used) or different. Thus, the antibodies of the invention may be used in sandwich pairs, or may be used individually with another binding entity which is not a monoclonal antibody such as a polyclonal antibody or an aptamer.

The antibodies of the present invention can be used as reagents in test kits for detecting CCL14 in biological samples. Such a test kit may, for example, comprise a disposable test device configured to generate a detectable signal related to the present or amount of human CCL14 in a biological sample. Alternatively, such a test kit may be formulated for performing an assay in a clinical analyzer which does not utilize a disposable test device. Preferably, the test kit is an in vitro diagnostic. The term "in vitro diagnostic" as used herein refers to a medical device which is a reagent, reagent product, calibrator, control material, kit, instrument, apparatus, equipment, or system, whether used alone or in combination, intended by the manufacturer to be used in vitro for the examination of specimens, including blood and tissue donations, derived from the human body, solely or principally for the purpose of providing information concerning a physiological or pathological state, or concerning a congenital abnormality, or to determine the safety and compatibility with potential recipients, or to monitor therapeutic measures.

In certain embodiments, the immunoassay is performed in a lateral flow format. Lateral flow tests are a form of immunoassay in which the test sample flows in a chromatographic fashion along a bibulous or non-bibulous porous solid substrate. Lateral flow tests can operate as either competitive or sandwich format assays. Preferred lateral flow devices are disposable, single use test devices. A sample is applied to the test device at an application zone and transits the substrate, where it encounters lines or zones which have been pretreated with an antibody or antigen. The term "test zone" as used herein refers to a discrete location on a lateral flow test strip which is interrogated in order to generate a signal related to the presence or amount of an analyte of interest. The detectable signal may be read visually or obtained by inserting the disposable test device into an analytical instrument such as a reflectometer, a fluorometer, or a transmission photometer. This list is not meant to be limiting. Sample may be applied without pretreatment to the application zone, or may be premixed with one or more assay reagents prior to application. In the latter case, the antibody may be provided in a separate container from the disposable test device.

An antibody of the present invention may be diffusively immobilized to a surface within a disposable test device, such that the antibody dissolves into a sample when the sample contacts the surface. In a sandwich assay format, this diffusively bound antibody may bind to its cognate antigen in the sample, and then be immobilized at a detection zone when the antigen is bound by a second antibody non-diffusively bound at the detection zone. In a competitive format, its cognate antigen in the sample may compete for binding to the non-diffusively bound antibody with a labeled antigen provided as an assay reagent.

A kit of the invention can further comprise a calibration to relate the detectable signal to a concentration of CCL14. By way of example, a calibration curve may be provided on an electronic memory device which is read by the analytical instrument which receives the disposable test device, such as a ROM chip, a flash drive, an RFID tag, etc. Alternatively, the calibration curve may be provided on an encoded label which is read optically, such as a 2-D bar code, or transmitted via a network connection. The analytical instrument can then use this calibration curve to relate a detectable signal from an assay into a CCL14 concentration In certain embodiment, an assay method performed using one or more antibodies of the present invention provides a signal related to the present or amount of human CCL14 in a biological sample, wherein the minimum detectable concentration of CCL14 in the assay method is 10 ng/mL or less, more preferably 1 ng/mL or less, and most preferably 0.1 ng/mL or less.

In related aspects, the present invention provides methods for determining the presence or amount of human CCL14 in a biological sample, comprising:

performing an immunoassay on the biological sample with a first monoclonal antibody and a second monoclonal antibody which together form sandwich complexes with human CCL14, wherein the immunoassay provides a detectable signal that is related to the presence or amount of human CCL14 in the biological sample bound in the sandwich complexes; and relating the detectable signal to the presence or amount of human CCL14 in the biological sample. Preferably, the minimum detectable concentration of CCL14 in the immunoassay is 10 ng/mL or less, more preferably 1 ng/mL or less, and most preferably 0.1 ng/mL or less.

In particularly preferred embodiments, the immunoassay is a sandwich immunoassay, in which each of the first and second antibodies are an antibody (which may be an antigen binding fragment) of the present invention. By way of example, the first antibody in the sandwich pair comprises one the following heavy chain CDR/light chain CDR pairs, and the second antibody in the sandwich pair comprises a different one the following heavy chain CDR/light chain CDR pairs:

a heavy chain variable region comprising a CDR1, CDR2, and CDR3 sequence from SEQ ID NO: 1, and a light chain variable region comprising a CDR1, CDR2, and CDR3 sequence from SEQ ID NO: 2 (2H3/2K1), a heavy chain variable region comprising a CDR1, CDR2, and CDR3 sequence from SEQ ID NO: 3, and a light chain variable region comprising a CDR1, CDR2, and CDR3 sequence from SEQ ID NO: 4 (3H1/3K1), a heavy chain variable region comprising a CDR1, CDR2, and CDR3 sequence from SEQ ID NO: 5, and a light chain variable region comprising a CDR1, CDR2, and CDR3 sequence from SEQ ID NO: 6 (4H1/4K3), a heavy chain variable region comprising a CDR1, CDR2, and CDR3 sequence from SEQ ID NO: 7, and a light chain variable region comprising a CDR1, CDR2, and CDR3 sequence from SEQ ID NO: 8 (10H3/10K1), a heavy chain variable region comprising a CDR1, CDR2, and CDR3 sequence from SEQ ID NO: 9, and a light chain variable region comprising a CDR1, CDR2, and CDR3 sequence from SEQ ID NO: 10 (12H2/12K1), a heavy chain variable region comprising a CDR1, CDR2, and CDR3 sequence from SEQ ID NO: 11, and a light chain variable region comprising a CDR1, CDR2, and CDR3 sequence from SEQ ID NO: 12 (17H2/17K1), a heavy chain variable region comprising a CDR1, CDR2, and CDR3 sequence from SEQ ID NO: 13, and a light chain variable region comprising a CDR1, CDR2, and CDR3 sequence from SEQ ID NO: 14 (18H1/18K1), a heavy chain variable region comprising a CDR1, CDR2, and CDR3 sequence from SEQ ID NO: 15, and a light chain variable region comprising a CDR1, CDR2, and CDR3 sequence from SEQ ID NO: 16 (19H2/19K3), a heavy chain variable region comprising a CDR1, CDR2, and CDR3 sequence from SEQ ID NO: 17, and a light chain variable region comprising a CDR1, CDR2, and CDR3 sequence from SEQ ID NO: 18 (25H2/25K1), or a heavy chain variable region comprising a CDR1, CDR2, and CDR3 sequence from SEQ ID NO: 19, and a light chain variable region comprising a CDR1, CDR2, and CDR3 sequence from SEQ ID NO: 20 (31H1/31K1).

In certain embodiments, the first antibody in the sandwich pair comprises one the following heavy chain CDR/light chain CDR pairs, and the second antibody in the sandwich pair comprises a different one the following heavy chain/light chain pairs:

a heavy chain variable region of SEQ ID NO: 1 or a corresponding heavy chain variable region having at least 90% sequence similarity to the framework region thereof, and a light chain variable region of SEQ ID NO: 2 a corresponding light chain variable region having at least 90% sequence similarity to the framework region thereof (2H3/2K1).

a heavy chain variable region of SEQ ID NO: 3 or a corresponding heavy chain variable region having at least 90% sequence similarity to the framework region thereof, and a light chain variable region of SEQ ID NO: 4 a corresponding light chain variable region having at least 90% sequence similarity to the framework region thereof (3H1/3K1), a heavy chain variable region of SEQ ID NO: 5 or a corresponding heavy chain variable region having at least 90% sequence similarity to the framework region thereof, and a light chain variable region of SEQ ID NO: 6 a corresponding light chain variable region having at least 90% sequence similarity to the framework region thereof (4H1/4K3), a heavy chain variable region of SEQ ID NO: 7 or a corresponding heavy chain variable region having at least 90% sequence similarity to the framework region thereof, and a light chain variable region of SEQ ID NO: 8 a corresponding light chain variable region having at least 90% sequence similarity to the framework region thereof (10H3/10K1), a heavy chain variable region of SEQ ID NO: 9 or a corresponding heavy chain variable region having at least 90% sequence similarity to the framework region thereof, and a light chain variable region of SEQ ID NO: 10 a corresponding light chain variable region having at least 90% sequence similarity to the framework region thereof (12H2/12K1), a heavy chain variable region of SEQ ID NO: 11 or a corresponding heavy chain variable region having at least 90% sequence similarity to the framework region thereof, and a light chain variable region of SEQ ID NO: 12 a corresponding light chain variable region having at least 90% sequence similarity to the framework region thereof (17H2/17K1), a heavy chain variable region of SEQ ID NO: 13 or a corresponding heavy chain variable region having at least 90% sequence similarity to the framework region thereof, and a light chain variable region of SEQ ID NO: 14 a corresponding light chain variable region having at least 90% sequence similarity to the framework region thereof (18H1/18K1), a heavy chain variable region of SEQ ID NO: 15 or a corresponding heavy chain variable region having at least 90% sequence similarity to the framework region thereof, and a light chain variable region of SEQ ID NO: 16 a corresponding light chain variable region having at least 90% sequence similarity to the framework region thereof (19H2/19K3), a heavy chain variable region of SEQ ID NO: 17 or a corresponding heavy chain variable region having at least 90% sequence similarity to the framework region thereof, and a light chain variable region of SEQ ID NO: 18 a corresponding heavy chain variable region having at least 90% sequence similarity to the framework region thereof (25H2/25K1), or a heavy chain variable region of SEQ ID NO: 19 or a corresponding heavy chain variable region having at least 90% sequence similarity to the framework region thereof, and a light chain variable region of SEQ ID NO: 20 a corresponding light chain variable region having at least 90% sequence similarity to the framework region thereof (31H1/31K1)

Examples of preferred sandwich pairs include 2H3/2K1 paired with 31H1/31K1; 2H3/2K1 paired with 10H3/10K1; and 31H1/31K1 paired with 10H3/10K1. This list is exemplary only.

In related aspects, the present invention relates to antibodies that bind to epitopes of an antibody of the present invention, or that compete for binding to CCL14 with an antibody of the present invention. As described herein, such antibodies may find use in kits, in antibody pairs, in methods, and in assay devices.

In preferred embodiments, a monoclonal antibody of the present invention binds to an epitope on human CCL14 that comprises all or part of the sequence HSVCTNPSDKWVQDYI (SEQ ID NO: 23), CCFTYT-TYKIPRQR (SEQ ID NO: 24), DKWVQDYIKDMK (SEQ ID NO: 25), MDYYETNSQCSK (SEQ ID NO: 26), ECCFTYTTYKIPR (SEQ ID NO: 27), TNSQCSKPG (SEQ ID NO: 28), or ETNSQCSKP (SEQ ID NO: 29), and is most preferably a rabbit monoclonal antibody.

In certain embodiments, an antibody of the present invention further comprises a second monoclonal antibody or antigen binding fragment which specifically binds human CCL14 and that binds to an epitope on human CCL14 that comprises all or part of the sequence CCFTYTTYKIPRQR (SEQ ID NO: 24), DKWVQDYIKDMK (SEQ ID NO: 25), MDYYETNSQCSK (SEQ ID NO: 26), ECCFTYTTYKIPR (SEQ ID NO: 27), TNSQCSKPG (SEQ ID NO: 28), or ETNSQCSKP (SEQ ID NO: 29), wherein the monoclonal antibody and the second antibody form sandwich complexes with human CCL14.

Preferred assay methods comprise performing an immunoassay that detects human CCL14. Such immunoassays may comprise contacting said body fluid sample with an antibody that detects the marker, and detecting binding to that antibody. While the present invention is generally described in terms of immunoassays, other binding entities (e.g., aptamers) which are not based on an immunoglobulin scaffold may be used in lieu of antibodies in such methods. Preferably, the body fluid sample is selected from the group consisting of urine, saliva, blood, serum, and plasma, and most preferably urine.

The details of one or more embodiments of the disclosure are set forth in the accompanying drawings and the description below. Other features, objects, and advantages of the disclosure will be apparent from the description and drawings, and from the claims.

BRIEF DESCRIPTION OF THE FIGURES

FIG. 1 shows a variable region alignment of the protein sequence for 2H3, 3H1,4H1,10H3,12H2,17H2,18H1,19H2, 25H2 and 31H1 rabbit IgG heavy chains of the invention. The three complementarity determining regions (CDR) are indicated.

FIG. 2 shows a variable region alignment of the protein sequence for 2K1,3K1,4K3,10K1,12K1,17K1,18K1,19K3, 25K1 and 31K1 rabbit light chain. The three complementarity determining regions (CDR) are indicated.

DETAILED DESCRIPTION

Definitions

Figure 3:
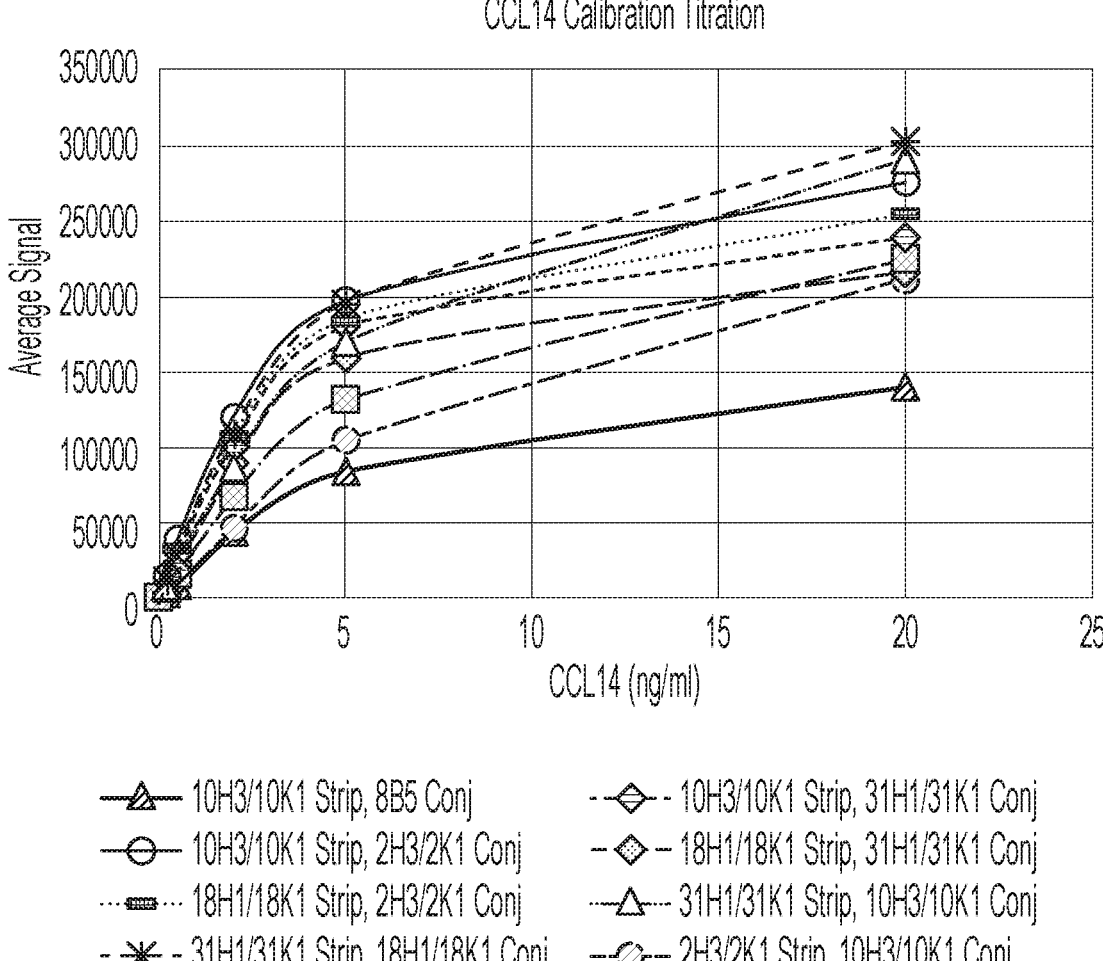
FIG. 3 shows results of sandwich assays using 2H3/2K1, 31H1/31K1, 18H1/18K1, and 10H3/10K1 antibodies.

The following is a list of sequences referred to in the present specification

TABLE 1

| Description | SEQ ID NO: | SEQUENCE |
|---|---|---|
| 2H3 heavy chain variable region sequence (amino acid sequence) | 1 | METGLRWLLLVAVLKGVQCQEQLKESGGGLVQPGGSL KLSCKASGFAFSSDYMSWVRQAPGKGLEWIGYIDPIF GSTAYASWVNGRFTISSHNAQNTLYLHLNSLTAADTA TYFCARDKDYSSGWGGYFNLWGQGTLVTVSS |
| 2K1 light chain variable region sequence (amino acid sequence) | 2 | MDTRAPTQLLGLLLLWLPGARCGAIVMTQTPASVEAA VGGTVTIKCQASQSINSYLAWYQQKPGQPPRLLIYEA STLASGVPSRFKGSGSGTQFTLTISDLECADAATYYC QTYYYSVDSSVGSNAFGGGTEVVVK |
| 3H1 heavy chain variable region sequence (amino acid sequence) | 3 | METGLRWLLLVAVLKGVQCQSVRESEGGGLFKPADTLT LTCTVSGFSLSSDAISWVRQAPGNGLEWIGAIDFGGS AYYASWAKSRSTITRNTNENTVTLKMTSLTAADTATY FCARSPSFGIVDRLDLWGQGTLVTVSS |
| 3K1 light chain variable region sequence (amino acid sequence) | 4 | MDTRAPTQLLGLLLLWLPGARCAVVLTQTASPVSAPV GGTVTIKCQASEDIDSYLAWYQQKPGQPPKLLIYDVF DLSSGVPSRFKGSGSGTEFTLTISDLECADAATYYCQ SYYYVLGTTSTDHNSFGGGTEVVVK |
| 4H1 heavy chain variable region sequence (amino acid sequence) | 5 | METGLRWLLLVAVLKGVQCQSVKESEGGLFKPADTLT LTCTVSGFSLSSFAINWVRQAPGEGLEYIGWISDVGT AYYASWAKSRSTITRNTDENTATLKMTSLTAADTATY FCAGGDGSYSNYWVSDIWGQGTLVTVSS |
| 4K3 light chain variable region sequence (amino acid sequence) | 6 | MDTRAPTQLLGLLLLWLPGARCAVVLTQTASPVSAPV GGTVTVKCQASQTINNRLAWYQQKQGQPPKLLIYEAS KLASGVPSRFKGSGSGTEYTLTIRGVECADAATYSCQ EYADENIFGGGTEVVVK |
| 10H3 heavy chain variable region sequence (amino acid sequence) | 7 | METGLRWLLLVAVLKGVQCQSVKESEGGLFKPADTLT LTCTVSGFSLSSYAINWVRQAPGEGLEYIGWISDVGT AYYASWAKSRSTITRNTDENTVTLKMTSLTAADTATY FCAGGDGSYSNYWVSDIWGQGTLVTVSS |
| 10K1 light chain variable region sequence (amino acid sequence) | 8 | MDTRAPTQLLGLLLLWLPGARCAVVLTQTPSLVSAPV GGTVTVKCRASQTINSRLAWYQQKQGQPPKLLIYEAS KLASGVPSRFKGSGSGTEYTLTIRGVECADAATYSCQ EYADENIFGGGTEVVVK |
| 12H2 heavy chain variable region sequence (amino acid sequence) | 9 | METGLRWLLLVAVLKGVQCQSVRESEGGLFKPADTLT LTCTVSGFSLSSDAISWVRQAPGNGLEWIGAIDFGGS AYYASWAKSRSTITRNTNENTVTLKMTSLTAADTATY FCARSPSFGIVDRLDLWGQGTLVTVSS |
| 12K1 light chain variable region sequence (amino acid sequence) | 10 | MDTRAPTQLLGLLLLWLPGARCAVVLTQTASPVSAPV GGTVTIKCQASEDIDSYLAWYQQKPGQPPKLLIYDVF DLSSGVPSRFKGSGSGTEFTLTISDLECADAATYYCQ SYYYVLGTTSTDHNSFGGGTEVVVK |
| 17H2 heavy chain variable region sequence (amino acid sequence) | 11 | METGLRWLLLVAVLKGVQCQSVKESEGGLFKPADTLT LTCTVSGFSLSSYAINWVRQAPGEGLEYIGWISDVGT AYYASWAKSRSTITRNTDENTVTLKMTSLTAADTATY FCAGGDGSYSNYWVSDIWGQGTLVTVSS |
| 17K1 light chain variable region sequence (amino acid sequence) | 12 | MDTRAPTQLLGLLLLWLPGARCAVVLTQTASPVSAPV GGTVTVKCQASQTINSRLAWYQQKQGQPPKLLIYEAS TLASGVPSRFKGSGSGTEYTLTIRGVECADAATYSCQ EYADENIFGGGTEVVVK |

TABLE 1 -continued

| Description | SEQ ID NO: | SEQUENCE |
|---|---|---|
| 18H1 heavy chain variable region sequence (amino acid sequence) | 13 | METGLRWLLLVAVLKGVQCQSVKESEGGGLFKPADTLT LTCTVSGFSLSSYAINWVRQAPGEGLEYIGWISDVGT AYYASWAKSRSTITRNTDENTVTLKMTSLTAADTATY FCAGGDGSYSNYWVSDIWGQGTLVTVSS |
| 18K1 light chain variable region sequence (amino acid sequence) | 14 | MDTRAPTQLLGLLLLWLPGARCAVVLTQTASPVSAPV GGTVTVKCQASQTINSRLAWYQQKQGQPPKLLIYEAS TLASGVPSRFKGSGSGTEYTLTIRGVECADAATYSCQ EYADENIFGGGTEVVVK |
| 19H2 heavy chain variable region sequence (amino acid sequence) | 15 | METGLRWLLLVAVLKGVQCQSVKESEGGGLFKPADTLT LTCTVSGFSLSSFAINWVRQAPGEGLEYIGWISDVGT AYYASWAKSRSTITRNADENTVTLKMTSLTAADTATY FCAGGDGSYSNYWVSDIWGQGTLVTVSS |
| 19K3 light chain variable region sequence (amino acid sequence) | 16 | MDTRAPTQLLGLLLLWLPGARCAVVLTQTASPVSAPV GGTVTVKCQASQTINNRLAWYQQKQGQPPKLLIYEAS KLASGVPSRFKGSGSGTEYTLTIRGVECADAATYSCQ EYADENIFGGGTEVVVK |
| 25H2 heavy chain variable region sequence (amino acid sequence) | 17 | METGLRWLLLVAVLKGVQCQSLEESGGDLVKPGASLT LTCTASRFDFSSAYYMCWVRQAPGKGLEWIACIYAGS SGGTYYATWAKGRFTISKTSSTTVTLQLTSLTAADTA TYFCAGSTGNSRGSYFNLWGQGTLVTVSS |
| 25K1 light chain variable region sequence (amino acid sequence) | 18 | MDTRAPTQLLGLLLLWLPGATFAQVLTQTPSPVSAAV GGTVTINCQSSQSVYDNNWLAWYQQKLGQPPKLVIYD ASKLASGVPSRFKGSGSGTHFTLTISELQCDDSATYY CQGEYSDIWGFGGGTEVVVK |
| 31H1 heavy chain variable region sequence (amino acid sequence) | 19 | METGLRWLLLVAVLKGVQCQSVRESEGGGLFKPADTLT LTCTVSGFSLSSDAISWVRQAPGNGLEWIGAIDFGGS AYYASWAKSRSTITRNTNENTVTLKMTSLTAADTATY FCARSPSFGIVDRLDLWGQGTLVTVSS |
| 31K1 light chain variable region sequence (amino acid sequence) | 20 | MDTRAPTQLLGLLLLWLPGAKCAVVLTQTASPVSAPV GGTVTIKCQASEDIDSYLAWYQQKPGQPPKLLIYDVF DLSSGVPSRFKGSGSGTEFTLTISDLECADAATYYCQ SYYYVLGTTSTDHNSFGGGTEVVVK |
| 10H3/10K1 epitope sequence | 23 | HSVCTNPSDKWVQDYI |
| 31H1/31K1 epitope sequence | 24 | CCFTYTTYKIPRQR |
| 25H2/25K1 epitope sequence 1 | 25 | DKWVQDYIKDMK |
| 25H2/25K1 epitope sequence 2 | 26 | MDYYETNSQCSK |
| 2H3/2K1 epitope 1 | 27 | ECCFTYTTYKIPR |
| 2H3/2K1 epitope 2 | 28 | TNSQCSKPG |
| 19H2/19K3 epitope | 29 | ETNSQCSKP |
| AF324 epitope sequence 1 | 30 | KTESSSRGPYHPSE |
| AF324 epitope sequence 2 | 31 | YTTYKIPRQRIM |
| MAB3241 | 24 | CCFTYTTYKIPRQR |

As used herein, the terms "C-C motif chemokine 14" and "CCL14" refer to one or more polypeptides present in a biological sample that are derived from the CCL14 precursor (human precursor: Swiss-Prot Q16627 (SEQ ID NO: 21)).

```
         10         20         30         40
MKISVAAIPF FLLITIALGT KTESSSRGPY HPSECCFTYT 50         60         70         80
TYKIPRQRIM DYYETNSQCS KPGIVFITKR GHSVCTNPSD

90
KWVQDYIKDM KEN
```

The following domains have been identified in CCL14:

| Residues | Length | Domain ID |
| --- | --- | --- |
| 1-19 | 19 | Signal peptide |
| 20-93 | 74 | CCL14 |
| 22-93 | 72 | HCC-1(3-74) |
| 23-93 | 71 | HCC-1(4-74) |
| 28-93 | 66 | HCC-1(9-74) |
| 27 | R → QTGGKPKVVKIQLKLVG (SEQ ID NO: 22) | HCC-3 |

Unless specifically noted otherwise herein, the definitions of the terms used are standard definitions used in the art of pharmaceutical sciences. As used in the specification and the appended claims, the singular forms "a," "an" and "the" include plural referents unless the context clearly dictates otherwise. Thus, for example, reference to "a pharmaceutical carrier" includes mixtures of two or more such carriers, and the like.

The term "subject" as used herein refers to a human or non-human organism. Thus, the methods and compositions described herein are applicable to both human and veterinary disease. Further, while a subject is preferably a living organism, the invention described herein may be used in post-mortem analysis as well. Preferred subjects are humans, and most preferably "patients," which as used herein refers to living humans that are receiving medical care for a disease or condition. This includes persons with no defined illness who are being investigated for signs of pathology.

Preferably, an analyte is measured in a sample. Such a sample may be obtained from a subject, or may be obtained from biological materials intended to be provided to the subject. For example, a sample may be obtained from a kidney being evaluated for possible transplantation into a subject, and an analyte measurement used to evaluate the kidney for preexisting damage. Preferred samples are body fluid samples.

The term "body fluid sample" as used herein refers to a sample of bodily fluid obtained for the purpose of diagnosis, prognosis, classification or evaluation of a subject of interest, such as a patient or transplant donor. In certain embodiments, such a sample may be obtained for the purpose of determining the outcome of an ongoing condition or the effect of a treatment regimen on a condition. Preferred body fluid samples include blood, serum, plasma, cerebrospinal fluid, urine, saliva, sputum, and pleural effusions. In addition, one of skill in the art would realize that certain body fluid samples would be more readily analyzed following a fractionation or purification procedure, for example, separation of whole blood into serum or plasma components.

The term "diagnosis" as used herein refers to methods by which the skilled artisan can estimate and/or determine the probability ("a likelihood") of whether or not a patient is suffering from a given disease or condition. In the case of the present invention, "diagnosis" includes using the results of an assay, most preferably an immunoassay, for a kidney injury marker of the present invention, optionally together with other clinical characteristics, to arrive at a diagnosis (that is, the occurrence or nonoccurrence) of an acute renal injury or ARF for the subject from which a sample was obtained and assayed. That such a diagnosis is "determined" is not meant to imply that the diagnosis is 100% accurate. Many biomarkers are indicative of multiple conditions. The skilled clinician does not use biomarker results in an informational vacuum, but rather test results are used together with other clinical indicia to arrive at a diagnosis. Thus, a measured biomarker level on one side of a predetermined diagnostic threshold indicates a greater likelihood of the occurrence of disease in the subject relative to a measured level on the other side of the predetermined diagnostic threshold.

Similarly, a prognostic risk signals a probability ("a likelihood") that a given course or outcome will occur. A level or a change in level of a prognostic indicator, which in turn is associated with an increased probability of morbidity (e.g., worsening renal function, future ARF, or death) is referred to as being "indicative of an increased likelihood" of an adverse outcome in a patient.

The term "lateral flow" as used herein refers to flow of reagents in a longitudinal direction through a substantially flat porous material. Such porous material is "substantially flat" if the thickness of the material is no more than 10% of the length and width dimensions.

The term "downstream region" as used herein relative to a first region of a device refers to which receives fluid flow after that fluid has already reached the first region.

The term "sample application region" as used herein refers to a portion of an assay device into which a fluid sample of interest is introduced for purposes of determining a component thereof.

Marker Assays

In general, immunoassays involve contacting a sample containing or suspected of containing a biomarker of interest with at least one antibody that specifically binds to the biomarker. A signal is then generated indicative of the presence or amount of complexes formed by the binding of polypeptides in the sample to the antibody. The signal is then related to the presence or amount of the biomarker in the sample. Numerous methods and devices are well known to the skilled artisan for the detection and analysis of biomarkers. See, e.g., U.S. Pat. Nos. 6,143,576; 6,113,855; 6,019,944; 5,985,579; 5,947,124; 5,939,272; 5,922,615; 5,885,527; 5,851,776; 5,824,799; 5,679,526; 5,525,524; and 5,480,792, and *The Immunoassay Handbook*, David Wild, ed. Stockton Press, New York, 1994, each of which is hereby incorporated by reference in its entirety, including all tables, figures and claims.

The assay devices and methods known in the art can utilize labeled molecules in various sandwich, competitive, or non-competitive assay formats, to generate a signal that is related to the presence or amount of the biomarker of interest. Suitable assay formats also include chromatographic, mass spectrographic, and protein "blotting" methods. Additionally, certain methods and devices, such as biosensors and optical immunoassays, may be employed to determine the presence or amount of analytes without the need for a labeled molecule. See, e.g., U.S. Pat. Nos. 5,631,171; and 5,955,377, each of which is hereby incorporated by reference in its entirety, including all tables, figures and claims. One skilled in the art also recognizes that robotic instrumentation including but not limited to Beckman ACCESS®, Abbott AXSYM®, Roche ELECSYS®, Dade Behring STRATUS® systems are among the immunoassay analyzers that are capable of performing immunoassays. But any suitable immunoassay may be utilized, for example, enzyme-linked immunoassays (ELISA), radioimmunoassays (RIAs), competitive binding assays, and the like.

Antibodies or other polypeptides may be immobilized onto a variety of solid supports for use in assays. Solid phases that may be used to immobilize specific binding members include those developed and/or used as solid phases in solid phase binding assays. Examples of suitable solid phases include membrane filters, cellulose-based papers, beads (including polymeric, latex and paramagnetic particles), glass, silicon wafers, microparticles, nanoparticles, TentaGels, AgroGels, PEGA gels, SPOCC gels, and multiple-well plates. An assay strip could be prepared by coating the antibody or a plurality of antibodies in an array on solid support. This strip could then be dipped into the test sample and then processed quickly through washes and detection steps to generate a measurable signal, such as a colored spot. Antibodies or other polypeptides may be bound to specific zones of assay devices either by conjugating directly to an assay device surface, or by indirect binding. In an example of the later case, antibodies or other polypeptides may be immobilized on particles or other solid supports, and that solid support immobilized to the device surface.

Biological assays require methods for detection, and one of the most common methods for quantitation of results is to conjugate a detectable label to a protein or nucleic acid that has affinity for one of the components in the biological system being studied. Detectable labels may include molecules that are themselves detectable (e.g., fluorescent moieties, electrochemical labels, metal chelates, etc.) as well as molecules that may be indirectly detected by production of a detectable reaction product (e.g., enzymes such as horseradish peroxidase, alkaline phosphatase, etc.) or by a specific binding molecule which itself may be detectable (e.g., biotin, digoxigenin, maltose, oligohistidine, 2,4-dintrobenzene, phenylarsenate, ssDNA, dsDNA, etc.).

Preparation of solid phases and detectable label conjugates often comprise the use of chemical cross-linkers. Cross-linking reagents contain at least two reactive groups, and are divided generally into homofunctional cross-linkers (containing identical reactive groups) and heterofunctional cross-linkers (containing non-identical reactive groups). Homobifunctional cross-linkers that couple through amines, sulfhydryls or react non-specifically are available from many commercial sources. Maleimides, alkyl and aryl halides, alpha-haloacyls and pyridyl disulfides are thiol reactive groups. Maleimides, alkyl and aryl halides, and alpha-haloacyls react with sulfhydryls to form thiol ether bonds, while pyridyl disulfides react with sulfhydryls to produce mixed disulfides. The pyridyl disulfide product is cleavable. Imidoesters are also very useful for protein-protein cross-links. A variety of heterobifunctional cross-linkers, each combining different attributes for successful conjugation, are commercially available.

In certain aspects, the present invention provides kits for the analysis of the described marker. The kit comprises reagents for the analysis of at least one test sample which comprise at least one antibody that specifically binds to the marker. The kit can also include devices and instructions for performing one or more of the diagnostic and/or prognostic correlations described herein. Preferred kits will comprise an antibody pair for performing a sandwich assay, or a labeled species for performing a competitive assay, for the analyte. Preferably, an antibody pair comprises a first antibody conjugated to a solid phase and a second antibody conjugated to a detectable label, wherein each of the first and second antibodies that bind a kidney injury marker. Most preferably each of the antibodies are monoclonal antibodies. The instructions for use of the kit and performing the correlations can be in the form of labeling, which refers to any written or recorded material that is attached to, or otherwise accompanies a kit at any time during its manufacture, transport, sale or use. For example, the term labeling encompasses advertising leaflets and brochures, packaging materials, instructions, audio or video cassettes, computer discs, as well as writing imprinted directly on kits.

In certain embodiments, the marker assay is performed using a single-use disposable test device. Such test devices often take the form of lateral flow devices which are now familiar from the common use of over-the-counter pregnancy tests. Generally, these assay devices have an extended base layer on which a differentiation can be made between a sample addition region and an evaluation region. In typical use, the sample is applied to the sample addition region, flows along a liquid transport path which runs parallel to the base layer, and then flows into the evaluation region. A capture reagent is present in the evaluation region, and the captured analyte can be detected by a variety of protocols to detect visible moieties associated with the captured analyte. For example, the assay may produce a visual signal, such as color change, fluorescence, luminescence, and the like, when indicating the presence or absence of an analyte in a biological sample.

A sample addition region can be provided, for example, in the form of an open chamber in a housing; in the form of an absorbent pad; etc. The sample addition region can be a port of various configurations, that is, round, oblong, square and the like or the region can be a trough in the device.

A filter element can be placed in, on, or adjacent to the sample addition region to filter particulates from the sample, such as to remove or retard blood cells from blood so that plasma can further travel through the device. Filtrate can then move into a porous member fluidly connected to the filter. Suitable filters for removing or retarding cellular material present in blood are well known in the art. See, e.g., U.S. Pat. Nos. 4,477,575; 5,166,051; 6,391,265; and 7,125, 493, each of which is hereby incorporated by reference in its entirety. Many suitable materials are known to skilled artisans, and can include glass fibers, synthetic resin fibers, membranes of various types including asymmetric membrane filters in which the pore size varies from about 65 to about 15 μm, and combinations of such materials. In addition, a filter element can comprise one or more chemical substances to facilitate separation of red blood cells from blood plasma. Examples of such chemical substances are thrombin, lectins, cationic polymers, antibodies against one or more red blood cell surface antigens and the like. Such chemical substance(s) which facilitate separation of red blood cells from plasma may be provided in the filter element by covalent means, nonspecific absorption, etc.

In certain embodiments, a label zone is located downstream of the sample receiving zone, and contains a diffusively located labeled reagent that binds to the analyte of interest or that competes with the analyte of interest for binding to a binding species. Alternatively, the label zone can be eliminated if the labeled reagent is premixed with the sample prior to application to the sample receiving zone. A detection zone is disposed downstream of from the label zone, and contains an immobilized capture reagent that binds to the analyte of interest.

The optimum pore diameter for the membrane for use in the invention is about 10 to about 50 μm. The membranes typically are from about 1 mil to about 15 mils in thickness, typically in the range of from 5 or 10 mils, but may be up to 200 mils and thicker. The membrane may be backed by a generally water impervious layer, such as a Mylar® polyester film (DuPont Teijin Films). When employed, the backing is generally fastened to the membrane by an adhesive, such as 3M 444 double-sided adhesive tape. Typically, a water impervious backing is used for membranes of low thickness. A wide variety of polymers may be used provided that they do not bind nonspecifically to the assay components and do not interfere with flow of the sample. Illustrative polymers include polyethylene, polypropylene, polystyrene and the like. Alternatively, the membrane may be self supporting. Other non-bibulous membranes, such as polyvinyl chloride, polyvinyl acetate, copolymers of vinyl acetate and vinyl chloride, polyamide, polycarbonate, polystyrene, and the like, can also be used. In various embodiments, the label zone material may be pretreated with a solution that includes blocking and stabilizing agents. Blocking agents include bovine serum albumin (BSA), methylated BSA, casein, nonfat dry milk. The device can also comprise additional components, including for example buffering agents, HAMA inhibitors, detergents, salts (e.g., chloride and/or sulfate salts of calcium, magnesium, potassium, etc.), and proteinaceous components (e.g., serum albumin, gelatin, milk proteins, etc.). This list is not meant to be limiting.

The device may further comprise various control locations which are read to determine that the test device has been run properly. By way of example, a procedural control zone may be provided separate from the assay detection zone to verify that the sample flow is as expected. The control zone is preferably a spatially distinct region at which a signal may be generated that is indicative of the proper flow of reagents. The procedural control zone may contain the analyte of interest, or a fragment thereof, to which excess labeled antibody used in the analyte assay can bind. In operation, a labeled reagent binds to the control zone, even when the analyte of interest is absent from the test sample. The use of a control line is helpful in that appearance of a signal in the control line indicates the time at which the test result can be read, even for a negative result. Thus, when the expected signal appears in the control line, the presence or absence of a signal in the capture zone can be noted. The device may further comprise a negative control area. The purpose of this control area is to alert the user that the test device is not working properly. When working properly, no signal or mark should be visible in the negative control area.

The outer casing or housing of such an assay device may take various forms. Typically, it will include an elongate casing and may have a plurality of interfitting parts. In a particularly preferred embodiment, the housing includes a top cover and a bottom support. The top cover contains an application aperture and an observation port. In a preferred embodiment, the housing is made of moisture impervious solid material, for example, a plastic material. It is contemplated that a variety of commercially available plastics, including, but not limited to, vinyl, nylon, polyvinyl chloride, polypropylene, polystyrene, polyethylene, polycarbonates, polysulfanes, polyesters, urethanes, and epoxies may be used to construct a housing. The housing may be prepared by conventional methodologies, such as standard molding technologies that are well known and used in the art. The housing may be produced by molding technologies which include, but are not limited to, injection molding, compression molding, transfer molding, blow molding, extrusion molding, foam molding, and thermoform molding. The aforementioned molding technologies are well known in the art and so are not discussed in detail herein. See for example, Processes And Materials Of Manufacture, Third Edition, R. A. Lindsberg (1983) Allyn and Baron pp. 393-431.

If necessary, the colorimetric, luminescent, or fluorescent intensity of the detectable label being employed may be then evaluated with an instrument that is appropriate to the label. By way of example, a fluorometer can be used to detect fluorescent labels; a reflectometer can be used to detect labels which absorb light, etc. The concentration of the analyte of interest in the samples may be determined by correlating the measured response to the amount of analyte in the sample fluid.

Assay Correlations

The terms "correlating" and "relating" as used herein in reference to the measurement of biomarkers in an assay refers to determining the presence, or more preferably the amount, of the biomarker in a sample based on the signal obtained from the assay. Often, this takes the form of comparing a signal generated from a detectable label on one species participating in the assay to a predetermined standard curve which can be used to convert the signal to a concentration or threshold amount of the biomarker.

The terms "correlating" and "relating" as used herein in reference to the use of biomarkers for diagnosis or prognosis refers to comparing the presence or amount of the biomarker(s) in a patient to its presence or amount in persons known to suffer from, or known to be at risk of, a given condition; or in persons known to be free of a given condition. Often, this takes the form of comparing an assay result in the form of a biomarker concentration to a predetermined threshold selected to be indicative of the occurrence or nonoccurrence of a disease or the likelihood of some future outcome.

Selecting a diagnostic threshold involves, among other things, consideration of the probability of disease, distribution of true and false diagnoses at different test thresholds, and estimates of the consequences of treatment (or a failure to treat) based on the diagnosis. For example, when considering administering a specific therapy which is highly efficacious and has a low level of risk, few tests are needed because clinicians can accept substantial diagnostic uncertainty. On the other hand, in situations where treatment options are less effective and more risky, clinicians often need a higher degree of diagnostic certainty. Thus, cost/benefit analysis is involved in selecting a diagnostic threshold.

Suitable thresholds may be determined in a variety of ways. For example, one recommended diagnostic threshold for the diagnosis of acute myocardial infarction using cardiac troponin is the 97.5th percentile of the concentration seen in a normal population. Another method may be to look at serial samples from the same_patient, where a prior "baseline" result is used to monitor for temporal changes in a biomarker level.

Population studies may also be used to select a decision threshold. Receiver Operating Characteristic ("ROC") arose from the field of signal detection theory developed during World War II for the analysis of radar images, and ROC analysis is often used to select a threshold able to best distinguish a "diseased" subpopulation from a "nondiseased" subpopulation. A false positive in this case occurs when the person tests positive, but actually does not have the disease. A false negative, on the other hand, occurs when the person tests negative, suggesting they are healthy, when they actually do have the disease. To draw a ROC curve, the true positive rate (TPR) and false positive rate (FPR) are determined as the decision threshold is varied continuously. Since TPR is equivalent with sensitivity and FPR is equal to 1–specificity, the ROC graph is sometimes called the sensitivity vs (1–specificity) plot. A perfect test will have an area under the ROC curve of 1.0; a random test will have an area of 0.5. A threshold is selected to provide an acceptable level of specificity and sensitivity.

In this context, "diseased" is meant to refer to a population having one characteristic (the presence of a disease or condition or the occurrence of some outcome) and "nondiseased" is meant to refer to a population lacking the characteristic. While a single decision threshold is the simplest application of such a method, multiple decision thresholds may be used. For example, below a first threshold, the absence of disease may be assigned with relatively high confidence, and above a second threshold the presence of disease may also be assigned with relatively high confidence. Between the two thresholds may be considered indeterminate. This is meant to be exemplary in nature only.

In addition to threshold comparisons, other methods for correlating assay results to a patient classification (occurrence or nonoccurrence of disease, likelihood of an outcome, etc.) include decision trees, rule sets, Bayesian methods, and neural_network methods. These methods can produce probability values representing the degree to which a subject belongs to one classification out of a plurality of classifications.

Measures of test accuracy may be obtained as described in Fischer et al., Intensive Care Med. 29: 1043-51, 2003, and used to determine the effectiveness of a given biomarker. These measures include sensitivity and specificity, predictive values, likelihood ratios, diagnostic odds ratios, and ROC curve areas. The area under the curve ("AUC") of a ROC plot is equal to the probability that a classifier will rank a randomly chosen positive instance higher than a randomly chosen negative one. The area under the ROC curve may be thought of as equivalent to the Mann-Whitney U test, which tests for the median difference between scores obtained in the two groups considered if the groups are of continuous data, or to the Wilcoxon test of ranks.

As discussed above, suitable tests may exhibit one or more of the following results on these various measures: a specificity of greater than 0.5, preferably at least 0.6, more preferably at least 0.7, still more preferably at least 0.8, even more preferably at least 0.9 and most preferably at least 0.95, with a corresponding sensitivity greater than 0.2, preferably greater than 0.3, more preferably greater than 0.4, still more preferably at least 0.5, even more preferably 0.6, yet more preferably greater than 0.7, still more preferably greater than 0.8, more preferably greater than 0.9, and most preferably greater than 0.95; a sensitivity of greater than 0.5, preferably at least 0.6, more preferably at least 0.7, still more preferably at least 0.8, even more preferably at least 0.9 and most preferably at least 0.95, with a corresponding specificity greater than 0.2, preferably greater than 0.3, more preferably greater than 0.4, still more preferably at least 0.5, even more preferably 0.6, yet more preferably greater than 0.7, still more preferably greater than 0.8, more preferably greater than 0.9, and most preferably greater than 0.95; at least 75% sensitivity, combined with at least 75% specificity; a ROC curve area of greater than 0.5, preferably at least 0.6, more preferably 0.7, still more preferably at least 0.8, even more preferably at least 0.9, and most preferably at least 0.95; an odds ratio different from 1, preferably at least about 2 or more or about 0.5 or less, more preferably at least about 3 or more or about 0.33 or less, still more preferably at least about 4 or more or about 0.25 or less, even more preferably at least about 5 or more or about 0.2 or less, and most preferably at least about 10 or more or about 0.1 or less; a positive likelihood ratio (calculated as sensitivity/(1–specificity)) of greater than 1, at least 2, more preferably at least 3, still more preferably at least 5, and most preferably at least 10; and or a negative likelihood ratio (calculated as (1–sensitivity)/specificity) of less than 1, less than or equal to 0.5, more preferably less than or equal to 0.3, and most preferably less than or equal to 0.1

Antibodies

The term "antibody" as used herein refers to a peptide or polypeptide derived from, modeled after or substantially encoded by an immunoglobulin gene or immunoglobulin genes, or fragments thereof, capable of specifically binding an antigen or epitope. See, e.g. Fundamental Immunology, 3rd Edition, W. E. Paul, ed., Raven Press, N.Y. (1993); Wilson (1994; J. Immunol. Methods 175:267-273; Yarmush (1992) J. Biochem. Biophys. Methods 25:85-97. The term antibody includes antigen-binding portions, i.e., "antigen binding sites," (e.g., fragments, subsequences, complementarity determining regions (CDRs)) that retain capacity to bind antigen, including (i) a Fab fragment, a monovalent fragment consisting of the VL, VH, CL and CH1 domains; (ii) a F(ab')2 fragment, a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody, (v) a dAb fragment (Ward et al., (1989) Nature 341:544-546), which consists of a VH domain; and (vi) an isolated complementarity determining region (CDR). Single chain antibodies are also included by reference in the term "antibody."

Preferred therapeutic antibodies are IgG antibodies. The term "IgG" as used herein is meant a polypeptide belonging to the class of antibodies that are substantially encoded by a recognized immunoglobulin gamma gene. In humans this class comprises IgG1, IgG2, IgG3, and IgG4. In mice this class comprises IgG1, IgG2a, IgG2b, IgG3. The known Ig domains in the IgG class of antibodies are VH, Cγ1, Cγ2, Cγ3, VL, and CL. IgG is the preferred class for therapeutic antibodies for several practical reasons. IgG antibodies are stable, easily purified, and able to be stored under conditions that are practical for pharmaceutical supply chains. In vivo they have a long biological half-life that is not just a function of their size but is also a result of their interaction with the so-called Fc receptor (or FcRn). This receptor seems to protect IgG from catabolism within cells and recycles it back to the plasma.

Antibodies are immunological proteins that bind a specific antigen. In most mammals, including humans and mice, antibodies are constructed from paired heavy and light polypeptide chains. The light and heavy chain variable regions show significant sequence diversity between antibodies, and are responsible for binding the target antigen. Each chain is made up of individual immunoglobulin (Ig) domains, and thus the generic term immunoglobulin is used for such proteins.

The term "specifically binds" is not intended to indicate that an antibody binds exclusively to its intended target since, as noted above, an antibody binds to any polypeptide displaying the epitope(s) to which the antibody binds. Rather, an antibody "specifically binds" if its affinity for its intended target is about 5-fold greater when compared to its affinity for a non-target molecule which does not display the appropriate epitope(s). Preferably the affinity of the antibody will be at least about 5 fold, preferably 10 fold, more preferably 25-fold, even more preferably 50-fold, and most preferably 100-fold or more, greater for a target molecule than its affinity for a non-target molecule. In preferred embodiments, Preferred antibodies bind with affinities of at least about $10^7$ $M^{-1}$, and preferably between about $10^8$ $M^{-1}$ to about $10^9$ $M^{-1}$, about $10^9$ $M^{-1}$ to about $10^{10}$ $M^{-1}$, or about $10^{10}$ $M^{-1}$ to about $10^{12}$ $M^{-1}$.

Affinity is calculated as $K_d = k_{off}/k_{on}$ ($k_{off}$ is the dissociation rate constant, $K_{on}$ is the association rate constant and $K_d$ is the equilibrium constant). Affinity can be determined at equilibrium by measuring the fraction bound (r) of labeled ligand at various concentrations (c). The data are graphed using the Scatchard equation: $r/c = K(n-r)$: where r=moles of bound ligand/mole of receptor at equilibrium; c=free ligand concentration at equilibrium; K=equilibrium association constant; and n=number of ligand binding sites per receptor molecule. By graphical analysis, r/c is plotted on the Y-axis versus r on the X-axis, thus producing a Scatchard plot. Antibody affinity measurement by Scatchard analysis is well known in the art. See, e.g., van Erp et al., *J. Immunoassay* 12: 425-43, 1991; Nelson and Griswold, *Comput. Methods Programs Biomed.* 27: 65-8, 1988.

Antibodies of the invention may be further characterized by epitope mapping, so that antibodies and epitopes may be selected that have the greatest clinical utility in the immunoassays described herein. The term "epitope" refers to an antigenic determinant capable of specific binding to an antibody. Epitopes usually consist of chemically active surface groupings of molecules such as amino acids or sugar side chains and usually have specific three dimensional structural characteristics, as well as specific charge characteristics. Conformational and nonconformational epitopes are distinguished in that the binding to the former but not the latter is lost in the presence of denaturing solvents. Preferably, an epitope is targeted which is present on the target molecule, but is partially or totally absent on non-target molecules.

In some embodiments, the antibody scaffold can be a mixture of sequences from different species. As such, if the antibody is an antibody, such antibody may be a chimeric antibody and/or a humanized antibody. In general, both "chimeric antibodies" and "humanized antibodies" refer to antibodies that combine regions from more than one species. For example, "chimeric antibodies" traditionally comprise variable region(s) from a mouse (or rat, in some cases) and the constant region(s) from a human. "Humanized antibodies" generally refer to non-human antibodies that have had the variable-domain framework regions swapped for sequences found in human antibodies. Generally, in a humanized antibody, the entire antibody, except the CDRs, is encoded by a polynucleotide of human origin or is identical to such an antibody except within its CDRs. The CDRs, some or all of which are encoded by nucleic acids originating in a non-human organism, are grafted into the beta-sheet framework of a human antibody variable region to create an antibody, the specificity of which is determined by the engrafted CDRs. The creation of such antibodies is described in, e.g., WO 92/11018, Jones, 1986, Nature 321: 522-525, Verhoeyen et al., 1988, Science 239:1534-1536. "Backmutation" of selected acceptor framework residues to the corresponding donor residues is often required to regain affinity that is lost in the initial grafted construct (U.S. Pat. Nos. 5,530,101; 5,585,089; 5,693,761; 5,693,762; 6,180, 370; 5,859,205; 5,821,337; 6,054,297; 6,407,213). The humanized antibody optimally also will comprise at least a portion of an immunoglobulin constant region, typically that of a human immunoglobulin, and thus will typically comprise a human Fc region. Humanized antibodies can also be generated using mice with a genetically engineered immune system. Roque et al., 2004, Biotechnol. Prog. 20:639-654. A variety of techniques and methods for humanizing and reshaping non-human antibodies are well known in the art (See Tsurushita & Vasquez, 2004, Humanization of Monoclonal Antibodies, Molecular Biology of B Cells, 533-545, Elsevier Science (USA), and references cited therein). Humanization methods include but are not limited to methods described in Jones et al., 1986, Nature 321:522-525; Riechmann et al., 1988; Nature 332:323-329; Verhoeyen et al., 1988, Science, 239:1534-1536; Queen et al., 1989, Proc Natl Acad Sci, USA 86:10029-33; He et al., 1998, J. Immunol. 160: 1029-1035; Carter et al., 1992, Proc Natl Acad Sci USA 89:4285-9, Presta et al., 1997, Cancer Res.57 (20):4593-9; Gorman et al., 1991, Proc. Natl. Acad. Sci. USA 88:4181-4185; O'Connor et al., 1998, Protein Eng 11:321-8. Humanization or other methods of reducing the immunogenicity of nonhuman antibody variable regions may include resurfacing methods, as described for example in Roguska et al., 1994, Proc. Natl. Acad. Sci. USA 91:969-973. In one embodiment, the parent antibody has been affinity matured, as is known in the art. Structure-based methods may be employed for humanization and affinity maturation, for example as described in U.S. Ser. No. 11/004,590. Selection based methods may be employed to humanize and/or affinity mature antibody variable regions, including but not limited to methods described in Wu et al., 1999, J. Mol. Biol. 294:151-162; Baca et al., 1997, J. Biol. Chem. 272(16):10678-10684; Rosok et al., 1996, J. Biol. Chem. 271(37): 22611-22618; Rader et al., 1998, Proc. Natl. Acad. Sci. USA 95: 8910-8915; Krauss et al., 2003, Protein Engineering 16(10):753-759. Other humanization methods may involve the grafting of only parts of the CDRs, including but not limited to methods described in U.S. Ser. No. 09/810,502; Tan et al., 2002, J. Immunol. 169:1119-1125; De Pascalis et al., 2002, J. Immunol. 169:3076-3084.

In one embodiment, the antibody is a fully human antibody. "Fully human antibody" or "complete human antibody" refers to a human antibody having the gene sequence of an antibody derived from a human chromosome. Fully human antibodies may be obtained, for example, using transgenic mice (Bruggemann et al., 1997, Curr Opin Biotechnol 8:455-458) or human antibody libraries coupled with selection methods (Griffiths et al., 1998, Curr Opin Biotechnol 9:102-108).

Production of Antibodies

Monoclonal antibody preparations can be produced using a wide variety of techniques known in the art including the use of hybridoma, recombinant, and phage display technologies, or a combination thereof. For example, monoclonal antibodies can be produced using hybridoma techniques including those known in the art and taught, for example, in Harlow et al., ANTIBODIES: A LABORATORY MANUAL, (Cold Spring Harbor Laboratory Press, 2nd ed. 1988); Hammerling, et al., in: MONOCLONAL ANTIBODIES AND T-CELL HYBRIDOMAS, pp. 563-681 (Elsevier, N.Y., 1981) (both of which are incorporated by reference in their entireties). The term "monoclonal antibody" as used herein is not limited to antibodies produced through hybridoma technology. The term "monoclonal antibody" refers to an antibody that is derived from a single clone, including any eukaryotic, prokaryotic, or phage clone, and not the method by which it is produced.

Monoclonal antibodies derived from animals other than rats and mice offer unique advantages. Many protein targets relevant to signal transduction and disease are highly conserved between mice, rats and humans, and can therefore be recognized as self-antigens by a mouse or rat host, making them less immunogenic. This problem may be avoided when using rabbit as a host animal. See, e.g., Rossi et al., *Am. J. Clin. Pathol.*, 124, 295-302, 2005.

Methods for producing and screening for specific antibodies using hybridoma technology are routine and well known in the art. In a non-limiting example, mice can be immunized with an antigen of interest or a cell expressing such an antigen. Once an immune response is detected, e.g., antibodies specific for the antigen are detected in the mouse serum, the mouse spleen is harvested and splenocytes isolated. The splenocytes are then fused by well known techniques to any suitable myeloma cells. Hybridomas are selected and cloned by limiting dilution. The hybridoma clones are then assayed by methods known in the art for cells that secrete antibodies capable of binding the antigen. Ascites fluid, which generally contains high levels of antibodies, can be generated by inoculating mice intraperitoneally with positive hybridoma clones.

Adjuvants that can be used in the methods of antibody generation include, but are not limited to, protein adjuvants; bacterial adjuvants, e.g., whole bacteria (BCG, *Corynebacterium parvum, Salmonella minnesota*) and bacterial components including cell wall skeleton, trehalose dimycolate, monophosphoryl lipid A, methanol extractable residue (MER) of tubercle bacillus, complete or incomplete Freund's adjuvant; viral adjuvants; chemical adjuvants, e.g., aluminum hydroxide, iodoacetate and cholesteryl hemisuccinateor; naked DNA adjuvants. Other adjuvants that can be used in the methods of the invention include, Cholera toxin, paropox proteins, MF-59 (Chiron Corporation; See also Bieg et al. (1999) "GAD65 And Insulin B Chain Peptide (9-23) Are Not Primary Autoantigens In The Type 1 Diabetes Syndrome Of The BB Rat," Autoimmunity, 31(1):15-24, which is incorporated herein by reference), MPL® (Corixa Corporation; See also Lodmell et al. (2000) "DNA Vaccination Of Mice Against Rabies Virus: Effects Of The Route Of Vaccination And The Adjuvant Monophosphoryl Lipid A (MPL)," Vaccine, 18: 1059-1066; Johnson et al. (1999) "3-O-Desacyl Monophosphoryl Lipid A Derivatives: Synthesis And Immunostimulant Activities," Journal of Medicinal Chemistry, 42: 4640-4649; Baldridge et al. (1999) "Monophosphoryl Lipid A (MPL) Formulations For The Next Generation Of Vaccines," Methods, 19: 103-107, all of which are incorporated herein by reference), RC-529 adjuvant (Corixa Corporation; the lead compound from Corixa's aminoalkyl glucosaminide 4-phosphate (AGP) chemical library, see also www.corixa.com), and DETOX™ adjuvant (Corixa Corporation; DETOX™ adjuvant includes MPL® adjuvant (monophosphoryl lipid A) and mycobacterial cell wall skeleton; See also Eton et al. (1998) "Active Immunotherapy With Ultraviolet B-Irradiated Autologous Whole Melanoma Cells Plus DETOX In Patients With Metastatic Melanoma," Clin. Cancer Res. 4(3):619-627; and Gupta et al. (1995) "Adjuvants For Human Vaccines—Current Status, Problems And Future Prospects," Vaccine, 13(14): 1263-1276, both of which are incorporated herein by reference).

Numerous publications discuss the use of phage display technology to produce and screen libraries of polypeptides for binding to a selected analyte. See, e.g, Cwirla et al., Proc. Natl. Acad. Sci. USA 87, 6378-82, 1990; Devlin et al., Science 249, 404-6, 1990, Scott and Smith, Science 249, 386-88, 1990; and Ladner et al., U.S. Pat. No. 5,571,698. A basic concept of phage display methods is the establishment of a physical association between DNA encoding a polypeptide to be screened and the polypeptide. This physical association is provided by the phage particle, which displays a polypeptide as part of a capsid enclosing the phage genome which encodes the polypeptide. The establishment of a physical association between polypeptides and their genetic material allows simultaneous mass screening of very large numbers of phage bearing different polypeptides. Phage displaying a polypeptide with affinity to a target bind to the target and these phage are enriched by affinity screening to the target. The identity of polypeptides displayed from these phage can be determined from their respective genomes. Using these methods a polypeptide identified as having a binding affinity for a desired target can then be synthesized in bulk by conventional means. See, e.g., U.S. Pat. No. 6,057,098, which is hereby incorporated in its entirety, including all tables, figures, and claims.

The antibodies that are generated by these methods may then be selected by first screening for affinity and specificity with the purified polypeptide of interest and, if required, comparing the results to the affinity and specificity of the antibodies with polypeptides that are desired to be excluded from binding. The screening procedure can involve immobilization of the purified polypeptides in separate wells of microtiter plates. The solution containing a potential antibody or groups of antibodies is then placed into the respective microtiter wells and incubated for about 30 min to 2 h. The microtiter wells are then washed and a labeled secondary antibody (for example, an anti-mouse antibody conjugated to alkaline phosphatase if the raised antibodies are mouse antibodies) is added to the wells and incubated for about 30 min and then washed. Substrate is added to the wells and a color reaction will appear where antibody to the immobilized polypeptide(s) are present.

The antibodies so identified may then be further analyzed for affinity and specificity in the assay design selected. In the development of immunoassays for a target protein, the purified target protein acts as a standard with which to judge the sensitivity and specificity of the immunoassay using the antibodies that have been selected. Because the binding affinity of various antibodies may differ; certain antibody pairs (e.g., in sandwich assays) may interfere with one another sterically, etc., assay performance of an antibody may be a more important measure than absolute affinity and specificity of an antibody.

Antibodies can also be produced using transgenic mice which are incapable of expressing functional endogenous immunoglobulins, but which can express human immunoglobulin genes. For example, the human heavy and light chain immunoglobulin gene complexes may be introduced randomly or by homologous recombination into mouse embryonic stem cells. Alternatively, the human variable region, constant region, and diversity region may be introduced into mouse embryonic stem cells in addition to the human heavy and light chain genes. The mouse heavy and light chain immunoglobulin genes may be rendered nonfunctional separately or simultaneously with the introduction of human immunoglobulin loci by homologous recombination. In particular, homozygous deletion of the JH region prevents endogenous antibody production. The modified embryonic stem cells are expanded and microinjected into blastocysts to produce chimeric mice. The chimeric mice are then bred to produce homozygous offspring which express human antibodies. The transgenic mice are immunized using conventional methodologies with a selected antigen, e.g., all or a portion of a polypeptide of the invention. Monoclonal antibodies directed against the antigen can be obtained from the immunized, transgenic mice using conventional hybridoma technology. The human immunoglobulin transgenes harbored by the transgenic mice rearrange during B cell differentiation, and subsequently undergo class switching and somatic mutation. Thus, using such a technique, it is possible to produce therapeutically useful IgG, IgA, IgM and IgE antibodies. For an overview of this technology for producing human antibodies, see Lonberg et al. (1995) "Human Antibodies From Transgenic Mice," Int. Rev. Immunol. 13:65-93, which is incorporated herein by reference in its entirety). For a detailed discussion of this technology for producing human antibodies and human monoclonal antibodies and protocols for producing such antibodies, see, e.g., International Publication Nos. WO 98/24893, WO 96/34096, and WO 96/33735; and U.S. Pat. Nos. 5,413,923, 5,625,126, 5,633,425, 5,569,825, 5,661, 016, 5,545,806, 5,814,318, and 5,939,598, which are incorporated by reference herein in their entirety. In addition, companies such as Abgenix, Inc. (Freemont, Calif.) and Medarex (Princeton, N.J.) can be engaged to provide human antibodies directed against a selected antigen using technology similar to that described above.

Recombinant Expression of Antibodies

Once a nucleic acid sequence encoding an antibody of the invention has been obtained, the vector for the production of the antibody may be produced by recombinant DNA technology using techniques well known in the art. Methods which are well known to those skilled in the art can be used to construct expression vectors containing the antibody coding sequences and appropriate transcriptional and translational control signals. These methods include, for example, in vitro recombinant DNA techniques, synthetic techniques, and in vivo genetic recombination. (See, for example, the techniques described in Sambrook et al, 1990, MOLECULAR CLONING, A LABORATORY MANUAL, 2d Ed., Cold Spring Harbor Laboratory, Cold Spring Harbor, N.Y. and Ausubel et al. eds., 1998, CURRENT PROTOCOLS IN MOLECULAR BIOLOGY, John Wiley & Sons, NY).

An expression vector comprising the nucleotide sequence of an antibody can be transferred to a host cell by conventional techniques (e.g., electroporation, liposomal transfection, and calcium phosphate precipitation) and the transfected cells are then cultured by conventional techniques to produce the antibody of the invention. In specific embodiments, the expression of the antibody is regulated by a constitutive, an inducible or a tissue, specific promoter.

The anti-CCL14 antibodies disclosed herein may also be produced recombinantly (e.g., in an E. coli/T7 expression system, a mammalian cell expression system or a lower eukaryote expression system). In this embodiment, nucleic acids encoding the antibody immunoglobulin molecules of the invention (e.g., VH or VL) may be inserted into a pET-based plasmid and expressed in the E. coli/T7 system. For example, the present invention includes methods for expressing an antibody or antigen-binding fragment thereof or immunoglobulin chain thereof in a host cell (e.g., bacterial host cell such as E. coli such as BL21 or BL21DE3) comprising expressing T7 RNA polymerase in the cell which also includes a polynucleotide encoding an immunoglobulin chain that is operably linked to a T7 promoter. For example, in an embodiment of the invention, a bacterial host cell, such as a E. coli, includes a polynucleotide encoding the T7 RNA polymerase gene operably linked to a lac promoter and expression of the polymerase and the chain is induced by incubation of the host cell with IPTG (isopropyl-beta-D-thiogalactopyranoside).

Thus, the present invention includes recombinant methods for making an anti-CCL14 antibody or antigen-binding fragment thereof of the present invention, or an immunoglobulin chain thereof, comprising introducing a polynucleotide encoding one or more immunoglobulin chains of the antibody or fragment (e.g., heavy and/or light immunoglobulin chain); culturing the host cell (e.g., CHO or Pichia or Pichia pastoris) under condition favorable to such expression and, optionally, isolating the antibody or fragment or chain from the host cell and/or medium in which the host cell is grown.

Anti-CCL14 antibodies can also be synthesized by any of the methods set forth in U.S. Pat. No. 6,331,415.

Eukaryotic and prokaryotic host cells, including mammalian cells as hosts for expression of the antibodies or fragments or immunoglobulin chains disclosed herein are well known in the art and include many immortalized cell lines available from the American Type Culture Collection (ATCC). These include, inter alia, Chinese hamster ovary (CHO) cells, NSO, SP2 cells, HeLa cells, baby hamster kidney (BHK) cells, monkey kidney cells (COS), human hepatocellular carcinoma cells (e.g., Hep G2), A549 cells, 3T3 cells, HEK-293 cells and a number of other cell lines. Mammalian host cells include human, mouse, rat, dog, monkey, pig, goat, bovine, horse and hamster cells. Cell lines of particular preference are selected through determining which cell lines have high expression levels. Other cell lines that may be used are insect cell lines, such as Sf9 cells, amphibian cells, bacterial cells, plant cells and fungal cells. Fungal cells include yeast and filamentous fungus cells including, for example, Pichia pastoris, Pichia finlandica, Pichia trehalophila, Pichia koclamae, Pichia membranaefaciens, Pichia minuta (Ogataea minuta, Pichia lindneri), Pichia opuntiae, Pichia thermotolerans, Pichia salictaria, Pichia guercuum, Pichia pijperi, Pichia stiptis, Pichia methanolica, Pichia sp., Saccharomyces cerevisiae, Saccharomyces sp., Hansenula polymorpha, Kluyveromyces sp., Kluyveromyces lactis, Candida albicans, Aspergillus nidulans, Aspergillus niger, Aspergillus oryzae, Trichoderma reesei, Chrysosporium lucknowense, Fusarium sp., Fusarium gramineum, Fusarium venenatum, Physcomitrella patens and Neurospora crassa. Pichia sp., any Saccharomyces sp., Hansenula polymorpha, any Kluyveromyces sp., Candida albicans, any Aspergillus sp., Trichoderma reesei, Chrysosporium lucknowense, any Fusarium sp., Yarrowia lipolytica, and Neurospora crassa. When recombinant expression vectors encoding the heavy chain or antigen-binding portion or fragment thereof, the light chain and/or antigen-binding fragment thereof are introduced into mammalian host cells, the antibodies are produced by culturing the host cells for a period of time sufficient to allow for expression of the antibody or fragment or chain in the host cells or secretion of the into the culture medium in which the host cells are grown.

A variety of host-expression vector systems may be utilized to express the antibodies of the invention. Such host-expression systems represent vehicles by which the coding sequences of the antibodies may be produced and subsequently purified, but also represent cells which may, when transformed or transfected with the appropriate nucleotide coding sequences, express the antibodies of the invention in situ. These include, but are not limited to, microorganisms such as bacteria (e.g., *E. coli* and *B. subtilis*) transformed with recombinant bacteriophage DNA, plasmid DNA or cosmid DNA expression vectors containing immunoglobulin coding sequences; yeast (e.g., *Saccharomyces pichia*) transformed with recombinant yeast expression vectors containing immunoglobulin coding sequences; insect cell systems infected with recombinant virus expression vectors (e.g., baculovirus) containing the immunoglobulin coding sequences; plant cell systems infected with recombinant virus expression vectors (e.g., cauliflower mosaic virus (CaMV) and tobacco mosaic virus (TMV)) or transformed with recombinant plasmid expression vectors (e.g., Ti plasmid) containing immunoglobulin coding sequences; or mammalian cell systems (e.g., COS, CHO, BHK, 293, 293T, 3T3 cells, lymphotic cells (see U.S. Pat. No. 5,807, 715), Per C.6 cells (rat retinal cells developed by Crucell)) harboring recombinant expression constructs containing promoters derived from the genome of mammalian cells (e.g., metallothionein promoter) or from mammalian viruses (e.g., the adenovirus late promoter; the vaccinia virus 7.5K promoter).

In bacterial systems, a number of expression vectors may be advantageously selected depending upon the use intended for the antibody being expressed. For example, when a large quantity of such a protein is to be produced, for the generation of pharmaceutical compositions of an antibody, vectors which direct the expression of high levels of fusion protein products that are readily purified may be desirable. Such vectors include, but are not limited to, the *E. coli* expression vector pUR278 (Ruther et al. (1983) "Easy Identification Of cDNA Clones," EMBO J. 2:1791-1794), in which the antibody coding sequence may be ligated individually into the vector in frame with the lac Z coding region so that a fusion protein is produced; pIN vectors (Inouye et al. (1985) "Up-Promoter Mutations In The Lpp Gene Of *Escherichia coli*," Nucleic Acids Res. 13:3101-3110; Van Heeke et al. (1989) "Expression Of Human Asparagine Synthetase In *Escherichia coli*," J. Biol. Chem. 24:5503-5509); and the like. pGEX vectors may also be used to express foreign polypeptides as fusion proteins with glutathione S-transferase (GST). In general, such fusion proteins are soluble and can easily be purified from lysed cells by adsorption and binding to a matrix glutathione-agarose beads followed by elution in the presence of free glutathione. The pGEX vectors are designed to include thrombin or factor Xa protease cleavage sites so that the cloned target gene product can be released from the GST moiety.

In an insect system, Autographa californica nuclear polyhedrosis virus (AcNPV) is used as a vector to express foreign genes. The virus grows in *Spodoptera frugiperda* cells. The antibody coding sequence may be cloned individually into non-essential regions (e.g., the polyhedrin gene) of the virus and placed under control of an AcNPV promoter (e.g., the polyhedrin promoter).

In mammalian host cells, a number of viral-based expression systems may be utilized. In cases where an adenovirus is used as an expression vector, the antibody coding sequence of interest may be ligated to an adenovirus transcription/translation control complex, e.g., the late promoter and tripartite leader sequence. This chimeric gene may then be inserted in the adenovirus genome by in vitro or in vivo recombination. Insertion in a non-essential region of the viral genome (e.g., region E1 or E3) will result in a recombinant virus that is viable and capable of expressing the immunoglobulin molecule in infected hosts. (see e.g., see Logan et al. (1984) "Adenovirus Tripartite Leader Sequence Enhances Translation Of mRNAs Late After Infection," Proc. Natl. Acad. Sci. (U.S.A.) 81:3655-3659). Specific initiation signals may also be required for efficient translation of inserted antibody coding sequences. These signals include the ATG initiation codon and adjacent sequences. Furthermore, the initiation codon must be in phase with the reading frame of the desired coding sequence to ensure translation of the entire insert. These exogenous translational control signals and initiation codons can be of a variety of origins, both natural and synthetic. The efficiency of expression may be enhanced by the inclusion of appropriate transcription enhancer elements, transcription terminators, etc. (see Bitter et al. (1987) "Expression And Secretion Vectors For Yeast," Methods in Enzymol. 153:516-544).

In addition, a host cell strain may be chosen which modulates the expression of the inserted sequences, or modifies and processes the gene product in the specific fashion desired. Such modifications (e.g., glycosylation) and processing (e.g., cleavage) of protein products may be important for the function of the protein. Different host cells have characteristic and specific mechanisms for the post-translational processing and modification of proteins and gene products. Appropriate cell lines or host systems can be chosen to ensure the correct modification and processing of the foreign protein expressed. To this end, eukaryotic host cells which possess the cellular machinery for proper processing of the primary transcript, glycosylation, and phosphorylation of the gene product may be used. Such mammalian host cells include but are not limited to CHO, VERY, BHK, Hela, COS, MDCK, 293, 293T, 3T3, WI38, BT483, Hs578T, HTB2, BT20 and T47D, CRL7030 and Hs578Bst.

For long-term, high-yield production of recombinant proteins, stable expression is preferred. For example, cell lines which stably express an antibody of the invention may be engineered. Rather than using expression vectors which contain viral origins of replication, host cells can be transformed with DNA controlled by appropriate expression control elements (e.g., promoter, enhancer, sequences, transcription terminators, polyadenylation sites, etc.), and a selectable marker. Following the introduction of the foreign DNA, engineered cells may be allowed to grow for 1-2 days in an enriched media, and then are switched to a selective media. The selectable marker in the recombinant plasmid confers resistance to the selection and allows cells to stably integrate the plasmid into their chromosomes and grow to form foci which in turn can be cloned and expanded into cell lines. This method may advantageously be used to engineer cell lines which express the antibodies of the invention. Such engineered cell lines may be particularly useful in screening and evaluation of compounds that interact directly or indirectly with the antibodies of the invention.

A number of selection systems may be used, including but not limited to the herpes simplex virus thymidine kinase (Wigler et al. (1977) "Transfer Of Purified Herpes Virus Thymidine Kinase Gene To Cultured Mouse Cells," Cell 11:223-232), hypoxanthine-guanine phosphoribosyltransferase (Szybalska et al. (1962) "Genetics Of Human Cess Line. IV. DNA-Mediated Heritable Transformation Of A Biochemical Trait," Proc. Natl. Acad. Sci. (U.S.A.) 48:2026-2034), and adenine phosphoribosyltransferase (Lowy et al. (1980) "Isolation Of Transforming DNA: Cloning The Hamster Aprt Gene," Cell 22:817-823) genes can be employed in tk-, hgprt- or aprt-cells, respectively. Also, antimetabolite resistance can be used as the basis of selection for the following genes: dhfr, which confers resistance to methotrexate (Wigler et al. (1980) "Transformation Of Mammalian Cells With An Amplfiable Dominant-Acting Gene," Proc. Natl. Acad. Sci. (U.S.A.) 77:3567-3570; O'Hare et al. (1981) "Transformation Of Mouse Fibroblasts To Methotrexate Resistance By A Recombinant Plasmid Expressing A Prokaryotic Dihydrofolate Reductase," Proc. Natl. Acad. Sci. (U.S.A.) 78:1527-1531); gpt, which confers resistance to mycophenolic acid (Mulligan et al. (1981) "Selection For Animal Cells That Express The Escherichia coli Gene Coding For Xanthine-Guanine Phosphoribosyltransferase," Proc. Natl. Acad. Sci. (U.S.A.) 78:2072-2076); neo, which confers resistance to the aminoglycoside G-418 (Tachibana et al. (1991) "Altered Reactivity Of Immunoglobutin Produced By Human-Human Hybridoma Cells Transfected By pSV2-Neo Gene," Cytotechnology 6(3):219-226; Tolstoshev (1993) "Gene Therapy, Concepts, Current Trials And Future Directions," Ann. Rev. Pharmacol. Toxicol. 32:573-596; Mulligan (1993) "The Basic Science Of Gene Therapy," Science 260:926-932; and Morgan et al. (1993) "Human gene therapy," Ann. Rev. Biochem. 62:191-217). Methods commonly known in the art of recombinant DNA technology which can be used are described in Ausubel et al. (eds.), 1993, CURRENT PROTOCOLS IN MOLECULAR BIOLOGY, John Wiley & Sons, NY; Kriegler, 1990, GENE TRANSFER AND EXPRESSION, A LABORATORY MANUAL, Stockton Press, NY; and in Chapters 12 and 13, Dracopoli et al. (eds), 1994, CURRENT PROTOCOLS IN HUMAN GENETICS, John Wiley & Sons, NY; Colbere-Garapin et al. (1981) "A New Dominant Hybrid Selective Marker For Higher Eukaryotic Cells," J. Mol. Biol. 150:1-14; and hygro, which confers resistance to hygromycin (Santerre et al. (1984) "Expression Of Prokaryotic Genes For Hygromycin B And G418 Resistance As Dominant-Selection Markers In Mouse L Cells," Gene 30:147-156).

The expression levels of an antibody of the invention can be increased by vector amplification (for a review, see Bebbington and Hentschel, "The Use Of Vectors Based On Gene Amplification For The Expression Of Cloned Genes In Mammaian Cells," in DNA CLONING, Vol. 3. (Academic Press, New York, 1987)). When a marker in the vector system expressing an antibody is amplifiable, increase in the level of inhibitor present in culture of host cell will increase the number of copies of the marker gene. Since the amplified region is associated with the nucleotide sequence of the antibody, production of the antibody will also increase (Crouse et al. (1983) "Expression And Amplification Of Engineered Mouse Dihydrofolate Reductase Minigenes," Mol. Cell. Biol. 3:257-266).

The host cell may be co-transfected with two expression vectors of the invention, the first vector encoding a heavy chain derived polypeptide and the second vector encoding a light chain derived polypeptide. The two vectors may contain identical selectable markers which enable equal expression of heavy and light chain polypeptides. Alternatively, a single vector may be used which encodes both heavy and light chain polypeptides. In such situations, the light chain should be placed before the heavy chain to avoid an excess of toxic free heavy chain (Proudfoot (1986) "Expression And Amplification Of Engineered Mouse Dihydrofolate Reductase Minigenes," Nature 322:562-565; Kohler (1980) "Immunoglobulin Chain Loss In Hybridoma Lines," Proc. Natl. Acad. Sci. (U.S.A.) 77:2197-2199). The coding sequences for the heavy and light chains may comprise cDNA or genomic DNA.

In general, glycoproteins produced in a particular cell line or transgenic animal will have a glycosylation pattern that is characteristic for glycoproteins produced in the cell line or transgenic animal. Therefore, the particular glycosylation pattern of an antibody will depend on the particular cell line or transgenic animal used to produce the antibody. However, all antibodies encoded by the nucleic acid molecules provided herein, or comprising the amino acid sequences provided herein, comprise the instant invention, independent of the glycosylation pattern the antibodies may have. Similarly, in particular embodiments, antibodies with a glycosylation pattern comprising only non-fucosylated N-glycans may be advantageous, because these antibodies have been shown to typically exhibit more potent efficacy than their fucosylated counterparts both in vitro and in vivo (See for example, Shinkawa et al., *J. Biol. Chem.* 278: 3466-3473 (2003); U.S. Pat. Nos. 6,946,292 and 7,214,775). These antibodies with non-fucosylated N-glycans are not likely to be immunogenic because their carbohydrate structures are a normal component of the population that exists in human serum IgG.

Once the antibody of the invention has been recombinantly expressed, it may be purified by any method known in the art for purification of an antibody, for example, by chromatography (e.g., ion exchange, affinity, particularly by affinity for the specific antigen after Protein A, and sizing column chromatography), centrifugation, differential solubility, or by any other standard technique for the purification of proteins.

Antibody Conjugates

The anti-CCL14 antibodies and antigen-binding fragments thereof disclosed herein may also be conjugated to a chemical moiety. The chemical moiety may be, inter alia, a polymer, a radionuclide or a cytotoxic factor. In particular embodiments, the chemical moiety is a polymer which increases the half-life of the antibody or fragment in the body of a subject. Suitable polymers include, but are not limited to, hydrophilic polymers which include but are not limited to polyethylene glycol (PEG) (e.g., PEG with a molecular weight of 2kDa, 5 kDa, 10 kDa, 12 kDa, 20 kDa, 30 kDa or 40 kDa), dextran and monomethoxypolyethylene glycol (mPEG). Lee, et al., (1999) (*Bioconj. Chem.* 10:973-981) discloses PEG conjugated single-chain antibodies. Wen, et al., (2001) (*Bioconj. Chem.* 12:545-553) disclose conjugating antibodies with PEG which is attached to a radiometal chelator (diethylenetriaminpentaacetic acid (DTPA)).

The antibodies and antigen-binding fragments thereof disclosed herein may also be conjugated with labels such as $^{99}Tc$, $^{90}Y$, $^{111}In$, $^{32}P$, $^{14}C$, $^{125}I$, $^{3}H$, $^{131}I$, $^{15}O$, $^{13}N$, $^{18}F$, $^{35}S$, $^{51}Cr$, $^{57}To$, $^{226}Ra$, $^{60}Co$, $^{59}Fe$, $^{57}Se$, $^{152}Eu$, $^{67}CU$, $^{217}Ci$, $^{211}At$, $^{212}Pb$, $^{47}Sc$, $^{109}Pd$, $^{234}Th$, and $^{40}K$, $^{157}Gd$, $^{55}Mn$, $^{52}Tr$, and $^{56}Fe$.

The antibodies and antigen-binding fragments disclosed herein may also be PEGylated, for example to increase its biological (e.g., serum) half-life. To PEGylate an antibody or fragment, the antibody or fragment, typically is reacted with a reactive form of polyethylene glycol (PEG), such as a reactive ester or aldehyde derivative of PEG, under conditions in which one or more PEG groups become attached to the antibody or antibody fragment. In particular embodiments, the PEGylation is carried out via an acylation reaction or an alkylation reaction with a reactive PEG molecule (or an analogous reactive water-soluble polymer). As used herein, the term "polyethylene glycol" is intended to encompass any of the forms of PEG that have been used to derivatize other proteins, such as mono (C1-C10) alkoxy- or aryloxy-polyethylene glycol or polyethylene glycol-maleimide. In certain embodiments, the antibody or fragment to be PEGylated is an aglycosylated antibody or fragment. Methods for PEGylating proteins are known in the art and can be applied to the antibodies of the invention. See, e.g., EP 0 154 316 and EP 0 401 384.

The antibodies and antigen-binding fragments disclosed herein may also be conjugated with fluorescent or chemilluminescent labels, including fluorophores such as rare earth chelates, fluorescein and its derivatives, rhodamine and its derivatives, isothiocyanate, phycoerythrin, phycocyanin, allophycocyanin, o-phthaladehyde, fluorescamine, $^{152}$Eu, dansyl, umbelliferone, luciferin, luminal label, isoluminal label, an aromatic acridinium ester label, an imidazole label, an acridimium salt label, an oxalate ester label, an aequorin label, 2,3-dihydrophthalazinediones, biotin/avidin, spin labels and stable free radicals.

The antibodies and antigen-binding fragments thereof of the invention may also be conjugated to a cytotoxic factor such as diptheria toxin, *Pseudomonas aeruginosa* exotoxin A chain, ricin A chain, abrin A chain, modeccin A chain, alpha-sarcin, *Aleurites fordii* proteins and compounds (e.g., fatty acids), dianthin proteins, *Phytoiacca americana* proteins PAPI, PAPII, and PAP-S, *Momordica charantia* inhibitor, curcin, crotin, *Saponaria officinalis* inhibitor, mitogellin, restrictocin, phenomycin, and enomycin.

Any method known in the art for conjugating the antibodies and antigen-binding fragments thereof of the invention to the various moieties may be employed, including those methods described by Hunter, et al., (1962) Nature 144:945; David, et al., (1974) *Biochemistry* 13:1014; Pain, et al., (1981) J. Immunol. Meth. 40:219; and Nygren, J., (1982) *Histochem. and Cytochem.* 30:407. Methods for conjugating antibodies and fragments are conventional and very well known in the art.

Therapeutic Uses of Anti-CCL14 Antibodies

Further provided are methods for treating subjects, including human subjects, in need of treatment with the isolated antibodies or antigen-binding fragments thereof disclosed herein.

To prepare pharmaceutical or sterile compositions of the anti-CCL14 antibodies and antigen-binding fragments of the invention (e.g., antibody 131A and humanized versions thereof), the antibody or antigen-binding fragment thereof is admixed with a pharmaceutically acceptable carrier or excipient. See, e.g., *Remington's Pharmaceutical Sciences* and *U.S. Pharmacopeia: National Formulary*, Mack Publishing Company, Easton, PA (1984).

Formulations of therapeutic and diagnostic agents may be prepared by mixing with acceptable carriers, excipients, or stabilizers in the form of, e.g., lyophilized powders, slurries, aqueous solutions or suspensions (see, e.g., Hardman, et al. (2001) Goodman and Gilman's *The Pharmacological Basis of Therapeutics*, McGraw-Hill, New York, NY; Gennaro (2000) Remington: *The Science and Practice of Pharmacy*, Lippincott, Williams, and Wilkins, New York, NY; Avis, et al. (eds.) (1993) *Pharmaceutical Dosage Forms: Parenteral Medications*, Marcel Dekker, NY; Lieberman, et al. (eds.) (1990) *Pharmaceutical Dosage Forms: Tablets*, Marcel Dekker, NY; Lieberman, et al. (eds.) (1990) *Pharmaceutical Dosage Forms: Disperse Systems*, Marcel Dekker, NY; Weiner and Kotkoskie (2000) *Excipient Toxicity and Safety*, Marcel Dekker, Inc., New York, NY).

Toxicity and therapeutic efficacy of the antibodies of the invention, administered alone or in combination with another therapeutic agent, can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index ($LD_{50}/ED_{50}$). The data obtained from these cell culture assays and animal studies can be used in formulating a range of dosage for use in human. The dosage of such compounds lies preferably within a range of circulating concentrations that include the $ED_{50}$ with little or no toxicity. The dosage may vary within this range depending upon the dosage form employed and the route of administration.

In a further embodiment, a further therapeutic agent that is administered to a subject in association with an anti-CCL14 antibody or antigen-binding fragment thereof of the invention (e.g., antibody 131A or humanized versions thereof) in accordance with the Physicians' Desk Reference 2003 (Thomson Healthcare; 57th edition (Nov. 1, 2002)).

The mode of administration can vary. Routes of administration include oral, rectal, transmucosal, intestinal, parenteral; intramuscular, subcutaneous, intradermal, intramedullary, intrathecal, direct intraventricular, intravenous, intraperitoneal, intranasal, intraocular, inhalation, insufflation, topical, cutaneous, transdermal, or intra-arterial.

In particular embodiments, the anti-CCL14 antibodies or antigen-binding fragments thereof of the invention (e.g., antibody 131A and humanized versions thereof) can be administered by an invasive route such as by injection. In further embodiments of the invention, an anti-CCL14 antibody or antigen-binding fragment thereof, or pharmaceutical composition thereof, is administered intravenously, subcutaneously, intramuscularly, intraarterially, intratumorally, or by inhalation, aerosol delivery. Administration by non-invasive routes (e.g., orally; for example, in a pill, capsule or tablet) is also within the scope of the present invention.

The present invention provides a vessel (e.g., a plastic or glass vial, e.g., with a cap or a chromatography column, hollow bore needle or a syringe cylinder) comprising any of the antibodies or antigen-binding fragments of the invention (e.g., antibody 131A and humanized versions thereof) or a pharmaceutical composition thereof. The present invention also provides an injection device comprising any of the antibodies or antigen-binding fragments of the invention (e.g., antibody 131A and humanized versions thereof) or a pharmaceutical composition thereof. An injection device is a device that introduces a substance into the body of a patient via a parenteral route, e.g., intramuscular, subcutaneous or intravenous. For example, an injection device may be a syringe (e.g., pre-filled with the pharmaceutical composition, such as an auto-injector) which, for example, includes a cylinder or barrel for holding fluid to be injected (e.g., antibody or fragment or a pharmaceutical composition thereof), a needle for piecing skin and/or blood vessels for injection of the fluid; and a plunger for pushing the fluid out of the cylinder and through the needle bore. In an embodiment of the invention, an injection device that comprises an antibody or antigen-binding fragment thereof of the present invention or a pharmaceutical composition thereof is an intravenous (IV) injection device. Such a device includes the antibody or fragment or a pharmaceutical composition thereof in a cannula or trocar/needle which may be attached to a tube which may be attached to a bag or reservoir for holding fluid (e.g., saline; or lactated ringer solution comprising NaCl, sodium lactate, KCl, $CaCl_2$ and optionally including glucose) introduced into the body of the patient through the cannula or trocar/needle. The antibody or fragment or a pharmaceutical composition thereof may, in an embodiment of the invention, be introduced into the device once the trocar and cannula are inserted into the vein of a subject and the trocar is removed from the inserted cannula. The IV device may, for example, be inserted into a peripheral vein (e.g., in the hand or arm); the superior vena cava or inferior vena cava, or within the right atrium of the heart (e.g., a central IV); or into a subclavian, internal jugular, or a femoral vein and, for example, advanced toward the heart until it reaches the superior vena cava or right atrium (e.g., a central venous line). In an embodiment of the invention, an injection device is an autoinjector; a jet injector or an external infusion pump. A jet injector uses a high-pressure narrow jet of liquid which penetrate the epidermis to introduce the antibody or fragment or a pharmaceutical composition thereof to a patient's body. External infusion pumps are medical devices that deliver the antibody or fragment or a pharmaceutical composition thereof into a patient's body in controlled amounts. External infusion pumps may be powered electrically or mechanically. Different pumps operate in different ways, for example, a syringe pump holds fluid in the reservoir of a syringe, and a moveable piston controls fluid delivery, an elastomeric pump holds fluid in a stretchable balloon reservoir, and pressure from the elastic walls of the balloon drives fluid delivery. In a peristaltic pump, a set of rollers pinches down on a length of flexible tubing, pushing fluid forward. In a multi-channel pump, fluids can be delivered from multiple reservoirs at multiple rates.

The pharmaceutical compositions disclosed herein may also be administered with a needleless hypodermic injection device; such as the devices disclosed in U.S. Pat. Nos. 6,620,135; 6,096,002; 5,399,163; 5,383,851; 5,312,335; 5,064,413; 4,941,880; 4,790,824 or 4,596,556. Such needleless devices comprising the pharmaceutical composition are also part of the present invention. The pharmaceutical compositions disclosed herein may also be administered by infusion. Examples of well-known implants and modules for administering the pharmaceutical compositions include those disclosed in: U.S. Pat. No. 4,487,603, which discloses an implantable micro-infusion pump for dispensing medication at a controlled rate; U.S. Pat. No. 4,447,233, which discloses a medication infusion pump for delivering medication at a precise infusion rate; U.S. Pat. No. 4,447,224, which discloses a variable flow implantable infusion apparatus for continuous drug delivery; U.S. Pat. No. 4,439,196, which discloses an osmotic drug delivery system having multi-chamber compartments. Many other such implants, delivery systems, and modules are well known to those skilled in the art and those comprising the pharmaceutical compositions of the present invention are within the scope of the present invention.

Alternately, one may administer the anti-CCL14 antibody or antigen-binding fragment of the invention (e.g., antibody 131A and humanized versions thereof) in a local rather than systemic manner, for example, via injection of the antibody or fragment directly into a tumor, e.g., a $CCL14^+$ tumor.

Furthermore, one may administer the antibody or fragment in a targeted drug delivery system, for example, in a liposome coated with a tissue-specific antibody, targeting, for example, a tumor e.g., a $CCL14^+$ tumor, e.g., characterized by immunopathology. The liposomes will be targeted to and taken up selectively by the afflicted tissue. Such methods and liposomes are part of the present invention.

The administration regimen depends on several factors, including the serum or tissue turnover rate of the therapeutic antibody or antigen-binding fragment, the level of symptoms, the immunogenicity of the therapeutic antibody, and the accessibility of the target cells in the biological matrix. Preferably, the administration regimen delivers sufficient therapeutic antibody or fragment to effect improvement in the target disease state, while simultaneously minimizing undesired side effects. Accordingly, the amount of biologic delivered depends in part on the particular therapeutic antibody and the severity of the condition being treated. Guidance in selecting appropriate doses of therapeutic antibodies or fragments is available (see, e.g., Wawrzynczak (1996) *Antibody Therapy*, Bios Scientific Pub. Ltd, Oxfordshire, UK; Kresina (ed.) (1991) *Monoclonal Antibodies, Cytokines and Arthritis*, Marcel Dekker, New York, NY; Bach (ed.) (1993) *Monoclonal Antibodies and Peptide Therapy in Autoimmune Diseases*, Marcel Dekker, New York, NY; Baert, et al. (2003) *New Engl. J. Med.* 348:601-608; Milgrom et al. (1999) *New Engl. J. Med.* 341:1966-1973; Slamon et al. (2001) *New Engl. J. Med.* 344:783-792; Beniaminovitz et al. (2000) *New Engl. J. Med.* 342:613-619; Ghosh et al. (2003) *New Engl. J. Med.* 348:24-32; Lipsky et al. (2000) *New Engl. J. Med.* 343:1594-1602).

Determination of the appropriate dose is made by the clinician, e.g., using parameters or factors known or suspected in the art to affect treatment. Generally, the dose begins with an amount somewhat less than the optimum dose and it is increased by small increments thereafter until the desired or optimum effect is achieved relative to any negative side effects. Important diagnostic measures include those of symptoms of, e.g., the inflammation or level of inflammatory cytokines produced. In general, it is desirable that a biologic that will be used is derived from the same species as the animal targeted for treatment, thereby minimizing any immune response to the reagent. In the case of human subjects, for example, humanized and fully human antibodies may be desirable.

Antibodies or antigen-binding fragments thereof disclosed herein (e.g., antibody 131A and humanized versions thereof) may be provided by continuous infusion, or by doses administered, e.g., daily, 1-7 times per week, weekly, bi-weekly, monthly, bimonthly, quarterly, semiannually, annually etc. Doses may be provided, e.g., intravenously, subcutaneously, topically, orally, nasally, rectally, intramuscular, intracerebrally, intraspinally, or by inhalation. A total weekly dose is generally at least 0.05 μg/kg body weight, more generally at least 0.2 μg/kg, 0.5 μg/kg, 1 μg/kg, 10 μg/kg, 100 μg/kg, 0.25 mg/kg, 1.0 mg/kg, 2.0 mg/kg, 5.0 mg/ml, 10 mg/kg, 25 mg/kg, 50 mg/kg or more (see, e.g., Yang, et al. (2003) *New Engl. J. Med.* 349:427-434; Herold, et al. (2002) *New Engl. J. Med.* 346:1692-1698; Liu, et al. (1999) *J. Neurol. Neurosurg. Psych.* 67:451-456; Portielji, et al. (20003) *Cancer Immunol. Immunother.* 52:151-144). Doses may also be provided to achieve a pre-determined target concentration of anti-CCL14 antibody in the subject's serum, such as 0.1, 0.3, 1, 3, 10, 30, 100, 300 μg/ml or more. In other embodiments, An anti-CCL14 antibody of the present invention is administered, e.g., subcutaneously or intravenously, on a weekly, biweekly, "every 4 weeks,"

monthly, bimonthly, or quarterly basis at 10, 20, 50, 80, 100, 200, 500, 1000 or 2500 mg/subject.

As used herein, the term "effective amount" refer to an amount of an anti-CCL14 or antigen-binding fragment thereof of the invention (e.g., antibody 131A and humanized versions thereof) that, when administered alone or in combination with an additional therapeutic agent to a cell, tissue, or subject, is effective to cause a measurable improvement in one or more symptoms of disease, for example cancer or the progression of cancer. An effective dose further refers to that amount of the antibody or fragment sufficient to result in at least partial amelioration of symptoms, e.g., tumor shrinkage or elimination, lack of tumor growth, increased survival time. When applied to an individual active ingredient administered alone, an effective dose refers to that ingredient alone. When applied to a combination, an effective dose refers to combined amounts of the active ingredients that result in the therapeutic effect, whether administered in combination, serially or simultaneously. An effective amount of a therapeutic will result in an improvement of a diagnostic measure or parameter by at least 10%; usually by at least 20%; preferably at least about 30%; more preferably at least 40%, and most preferably by at least 50%. An effective amount can also result in an improvement in a subjective measure in cases where subjective measures are used to assess disease severity.

Experimental and Diagnostic Uses

The anti-CCL14 antibodies and antigen-binding fragments thereof disclosed herein may be used as affinity purification agents. In this process, the anti-CCL14 antibodies and antigen-binding fragments thereof are immobilized on a solid phase such a Sephadex, glass or agarose resin or filter paper, using methods well known in the art. The immobilized antibody or fragment is contacted with a sample containing the CCL14 protein (or a fragment thereof) to be purified, and thereafter the support is washed with a suitable solvent that will remove substantially all the material in the sample except the CCL14 protein, which is bound to the immobilized antibody or fragment. Finally, the support is washed with a solvent which elutes the bound CCL14 (e.g., protein A). Such immobilized antibodies and fragments form part of the present invention.

Further provided are antigens for generating secondary antibodies which are useful for example for performing Western blots and other immunoassays discussed herein.

Anti-CCL14 antibodies (e.g., humanized antibodies) and antigen-binding fragments thereof may also be useful in diagnostic assays for CCL14 protein, e.g., detecting its expression in specific cells, tissues, or serum, e.g., tumor cells such as melanoma cells. Such diagnostic methods may be useful in various disease diagnoses.

The present invention includes ELISA assays (enzyme-linked immunosorbent assay) incorporating the use of an anti-CCL14 antibody or antigen-binding fragment thereof disclosed herein (e.g., antibody 131A or a humanized version thereof).

For example, such a method comprises the following steps:

(a) coat a substrate (e.g., surface of a microtiter plate well, e.g., a plastic plate) with anti-CCL14 antibody or antigen-binding fragment thereof;

(b) apply a sample to be tested for the presence of CCL14 to the substrate;

(c) wash the plate, so that unbound material in the sample is removed;

(d) apply detectably labeled antibodies (e.g., enzyme-linked antibodies) which are also specific to the CCL14 antigen;

(e) wash the substrate, so that the unbound, labeled antibodies are removed;

(f) if the labeled antibodies are enzyme linked, apply a chemical which is converted by the enzyme into a fluorescent signal; and (g) detect the presence of the labeled antibody.

Detection of the label associated with the substrate indicates the presence of the CCL14 protein.

In a further embodiment, the labeled antibody or antigen-binding fragment thereof is labeled with peroxidase which react with ABTS (e.g., 2,2'-azino-bis(3-ethylbenzthiazoline-6-sulphonic acid)) or 3,3',5,5'-Tetramethylbenzidine to produce a color change which is detectable. Alternatively, the labeled antibody or fragment is labeled with a detectable radioisotope (e.g., $^3H$) which can be detected by scintillation counter in the presence of a scintillant.

An anti-CCL14 antibody or antigen-binding fragment thereof of the invention may be used in a Western blot or immune-protein blot procedure. Such a procedure forms part of the present invention and includes e.g., optionally transferring proteins from a sample to be tested for the presence of CCL14 (e.g., from a PAGE or SDS-PAGE electrophoretic separation of the proteins in the sample) onto a membrane or other solid substrate using a method known in the art (e.g., semi-dry blotting or tank blotting); contacting the membrane or other solid substrate to be tested for the presence of bound CCL14 or a fragment thereof with an anti-CCL14 antibody or antigen-binding fragment thereof of the invention; washing the membrane one or more times to remove unbound anti-CCL14 antibody or fragment and other unbound substances; and detecting the bound anti-CCL14 antibody or fragment.

Such a membrane may take the form of a nitrocellulose or vinyl-based (e.g., polyvinylidene fluoride (PVDF)) membrane to which the proteins to be tested for the presence of CCL14 in a non-denaturing PAGE (polyacrylamide gel electrophoresis) gel or SDS-PAGE (sodium dodecyl sulfate polyacrylamide gel electrophoresis) gel have been transferred (e.g., following electrophoretic separation in the gel). Before contacting the membrane with the anti-CCL14 antibody or fragment, the membrane is optionally blocked, e.g., with non-fat dry milk or the like so as to bind non-specific protein binding sites on the membrane.

Detection of the bound antibody or fragment indicates that the CCL14 protein is present on the membrane or substrate and in the sample. Detection of the bound antibody or fragment may be by binding the antibody or fragment with a secondary antibody (an anti-immunoglobulin antibody) which is detectably labeled and, then, detecting the presence of the secondary antibody.

The anti-CCL14 antibodies and antigen-binding fragments thereof disclosed herein may also be used for immunohistochemistry. Such a method forms part of the present invention and comprises, e.g., contacting a cell (e.g., a tumor cell such as a melanoma cell) to be tested for the presence of CCL14 protein with an anti-CCL14 antibody or antigen-binding fragment thereof of the invention; and detecting the antibody or fragment on or in the cell.

If the antibody or fragment itself is detectably labeled, it can be detected directly. Alternatively, the antibody or fragment may be bound by a detectably labeled secondary antibody which is detected.

Certain anti-CCL14 antibodies and antigen-binding fragments thereof disclosed herein may also be used for in vivo tumor imaging. Such a method may include injection of a radiolabeled anti-CCL14 antibody or antigen-binding fragment thereof into the body of a patient to be tested for the presence of a tumor associated with CCL14 expression (e.g., which expresses CCL14, for example, on the tumor cell surface) followed by nuclear imaging of the body of the patient to detect the presence of the labeled antibody or fragment e.g., at loci comprising a high concentration of the antibody or fragment which are bound to the tumor. The detection of the loci indicates the presence of the CCL14$^+$ tumor and tumor cells.

Imaging techniques include SPECT imaging (single photon emission computed tomography) or PET imaging (positron emission tomography). Labels include e.g., iodine-123 ($^{123}$I) and technetium-99m($^{99m}$Tc), e.g., in conjunction with SPECT imaging or $^{11}$C, $^{13}$N, $^{15}$O or $^{18}$F, e.g., in conjunction with PET imaging or Indium-111 (See e.g., Gordon et al., (2005) International Rev. Neurobiol. 67:385-440).

Pharmaceutical Compositions and Administration

To prepare pharmaceutical or sterile compositions of the anti-CCL14 antibodies and antigen-binding fragments of the invention, the antibody or antigen-binding fragment thereof is admixed with a pharmaceutically acceptable carrier or excipient. See, e.g., Remington's *Pharmaceutical Sciences and U.S. Pharmacopeia: National Formulary*, Mack Publishing Company, Easton, PA (1984).

Formulations of therapeutic and diagnostic agents may be prepared by mixing with acceptable carriers, excipients, or stabilizers in the form of, e.g., lyophilized powders, slurries, aqueous solutions or suspensions (see, e.g., Hardman, et al. (2001) Goodman and Gilman's *The Pharmacological Basis of Therapeutics*, McGraw-Hill, New York, NY; Gennaro (2000) Remington: *The Science and Practice of Pharmacy*, Lippincott, Williams, and Wilkins, New York, NY; Avis, et al. (eds.) (1993) *Pharmaceutical Dosage Forms: Parenteral Medications*, Marcel Dekker, NY; Lieberman, et al. (eds.) (1990) *Pharmaceutical Dosage Forms*: Tablets, Marcel Dekker, NY; Lieberman, et al. (eds.) (1990) *Pharmaceutical Dosage Forms: Disperse Systems*, Marcel Dekker, NY; Weiner and Kotkoskie (2000) *Excipient Toxicity and Safety*, Marcel Dekker, Inc., New York, NY).

Toxicity and therapeutic efficacy of the antibodies of the invention, administered alone or in combination with another therapeutic agent, can be determined by standard pharmaceutical procedures in cell cultures or experimental animals, e.g., for determining the LD$_{50}$ (the dose lethal to 50% of the population) and the E$_{50}$ (the dose therapeutically effective in 50% of the population). The dose ratio between toxic and therapeutic effects is the therapeutic index (LD$_{50}$/ED$_{50}$). The data obtained from these cell culture assays and animal studies can be used in formulating a range of dosage for use in human. The dosage of such compounds lies preferably within a range of circulating concentrations that include the ED$_{50}$ with little or no toxicity. The dosage may vary within this range depending upon the dosage form employed and the route of administration.

In a further embodiment, a further therapeutic agent that is administered to a subject in association with an anti-CCL14 antibody or antigen-binding fragment thereof of the invention in accordance with the Physicians' Desk Reference 2003 (Thomson Healthcare; 57th edition (Nov. 1, 2002)).

The mode of administration can vary. Routes of administration include oral, rectal, transmucosal, intestinal, parenteral; intramuscular, subcutaneous, intradermal, intramedullary, intrathecal, direct intraventricular, intravenous, intraperitoneal, intranasal, intraocular, inhalation, insufflation, topical, cutaneous, transdermal, intratumoral, or intra-arterial.

In particular embodiments, the anti-CCL14 antibodies or antigen-binding fragments thereof of the invention can be administered by an invasive route such as by injection. In further embodiments of the invention, an anti-CCL14 antibody or antigen-binding fragment thereof, or pharmaceutical composition thereof, is administered intravenously, subcutaneously, intramuscularly, intraarterially, intratumorally, or by inhalation, aerosol delivery. Administration by non-invasive routes (e.g., orally; for example, in a pill, capsule or tablet) is also within the scope of the present invention.

The present invention provides a vessel (e.g., a plastic or glass vial, e.g., with a cap or a chromatography column, hollow bore needle or a syringe cylinder) comprising any of the antibodies or antigen-binding fragments of the invention or a pharmaceutical composition thereof. The present invention also provides an injection device comprising any of the antibodies or antigen-binding fragments of the invention or a pharmaceutical composition thereof. An injection device is a device that introduces a substance into the body of a patient via a parenteral route, e.g., intramuscular, subcutaneous or intravenous. For example, an injection device may be a syringe (e.g., pre-filled with the pharmaceutical composition, such as an auto-injector) which, for example, includes a cylinder or barrel for holding fluid to be injected (e.g., antibody or fragment or a pharmaceutical composition thereof), a needle for piecing skin and/or blood vessels for injection of the fluid; and a plunger for pushing the fluid out of the cylinder and through the needle bore. In an embodiment of the invention, an injection device that comprises an antibody or antigen-binding fragment thereof of the present invention or a pharmaceutical composition thereof is an intravenous (IV) injection device. Such a device includes the antibody or fragment or a pharmaceutical composition thereof in a cannula or trocar/needle which may be attached to a tube which may be attached to a bag or reservoir for holding fluid (e.g., saline; or lactated ringer solution comprising NaCl, sodium lactate, KCl, CaCl$_2$ and optionally including glucose) introduced into the body of the patient through the cannula or trocar/needle. The antibody or fragment or a pharmaceutical composition thereof may, in an embodiment of the invention, be introduced into the device once the trocar and cannula are inserted into the vein of a subject and the trocar is removed from the inserted cannula. The IV device may, for example, be inserted into a peripheral vein (e.g., in the hand or arm); the superior vena cava or inferior vena cava, or within the right atrium of the heart (e.g., a central IV); or into a subclavian, internal jugular, or a femoral vein and, for example, advanced toward the heart until it reaches the superior vena cava or right atrium (e.g., a central venous line). In an embodiment of the invention, an injection device is an autoinjector; a jet injector or an external infusion pump. A jet injector uses a high-pressure narrow jet of liquid which penetrate the epidermis to introduce the antibody or fragment or a pharmaceutical composition thereof to a patient's body. External infusion pumps are medical devices that deliver the antibody or fragment or a pharmaceutical composition thereof into a patient's body in controlled amounts. External infusion pumps may be powered electrically or mechanically. Different pumps operate in different ways, for example, a syringe pump holds fluid in the reservoir of a syringe, and a moveable piston controls fluid delivery, an elastomeric pump holds fluid in a stretchable balloon reservoir, and pressure from the elastic walls of the balloon drives fluid delivery. In a peristaltic pump, a set of rollers pinches down on a length of flexible tubing, pushing fluid forward. In a multi-channel pump, fluids can be delivered from multiple reservoirs at multiple rates.

The pharmaceutical compositions disclosed herein may also be administered with a needleless hypodermic injection device; such as the devices disclosed in U.S. Pat. Nos. 6,620,135; 6,096,002; 5,399,163; 5,383,851; 5,312,335; 5,064,413; 4,941,880; 4,790,824 or 4,596,556. Such needleless devices comprising the pharmaceutical composition are also part of the present invention. The pharmaceutical compositions disclosed herein may also be administered by infusion. Examples of well-known implants and modules for administering the pharmaceutical compositions include those disclosed in: U.S. Pat. No. 4,487,603, which discloses an implantable micro-infusion pump for dispensing medication at a controlled rate; U.S. Pat. No. 4,447,233, which discloses a medication infusion pump for delivering medication at a precise infusion rate; U.S. Pat. No. 4,447,224, which discloses a variable flow implantable infusion apparatus for continuous drug delivery; U.S. Pat. No. 4,439,196, which discloses an osmotic drug delivery system having multi-chamber compartments. Many other such implants, delivery systems, and modules are well known to those skilled in the art and those comprising the pharmaceutical compositions of the present invention are within the scope of the present invention.

Alternately, one may administer the anti-CCL14 antibody or antigen-binding fragment of the invention in a local rather than systemic manner, for example, via injection of the antibody or fragment directly into a tumor, e.g., a CCL14$^+$ tumor. Furthermore, one may administer the antibody or fragment in a targeted drug delivery system, for example, in a liposome coated with a tissue-specific antibody, targeting, for example, a tumor e.g., a CCL14$^+$ tumor, e.g., characterized by immunopathology. The liposomes will be targeted to and taken up selectively by the afflicted tissue. Such methods and liposomes are part of the present invention.

The administration regimen depends on several factors, including the serum or tissue turnover rate of the therapeutic antibody or antigen-binding fragment, the level of symptoms, the immunogenicity of the therapeutic antibody, and the accessibility of the target cells in the biological matrix. Preferably, the administration regimen delivers sufficient therapeutic antibody or fragment to effect improvement in the target disease state, while simultaneously minimizing undesired side effects. Accordingly, the amount of biologic delivered depends in part on the particular therapeutic antibody and the severity of the condition being treated. Guidance in selecting appropriate doses of therapeutic antibodies or fragments is available (see, e.g., Wawrzynczak (1996) *Antibody Therapy*, Bio s Scientific Pub. Ltd, Oxfordshire, UK; Kresina (ed.) (1991) *Monoclonal Antibodies, Cytokines and Arthritis*, Marcel Dekker, New York, NY; Bach (ed.) (1993) *Monoclonal Antibodies and Peptide Therapy in Autoimmune Diseases*, Marcel Dekker, New York, NY; Baert, et al. (2003) *New Engl. J. Med.* 348:601-608; Milgrom et al. (1999) *New Engl. J. Med.* 341:1966-1973; Slamon et al. (2001) *New Engl. J. Med.* 344:783-792; Beniaminovitz et al. (2000) *New Engl. J. Med.* 342:613-619; Ghosh et al. (2003) *New Engl. J. Med.* 348:24-32; Lipsky et al. (2000) *New Engl. J. Med.* 343:1594-1602).

Determination of the appropriate dose is made by the clinician, e.g., using parameters or factors known or suspected in the art to affect treatment. Generally, the dose begins with an amount somewhat less than the optimum dose and it is increased by small increments thereafter until the desired or optimum effect is achieved relative to any negative side effects. Important diagnostic measures include those of symptoms of, e.g., the inflammation or level of inflammatory cytokines produced. In general, it is desirable that a biologic that will be used is derived from the same species as the animal targeted for treatment, thereby minimizing any immune response to the reagent. In the case of human subjects, for example, humanized and fully human antibodies are may be desirable.

Antibodies or antigen-binding fragments thereof disclosed herein may be provided by continuous infusion, or by doses administered, e.g., daily, 1-7 times per week, weekly, bi-weekly, monthly, bimonthly, quarterly, semiannually, annually etc. Doses may be provided, e.g., intravenously, subcutaneously, topically, orally, nasally, rectally, intramuscular, intracerebrally, intraspinally, or by inhalation. A total weekly dose is generally at least 0.05 µg/kg body weight, more generally at least 0.2 µg/kg, 0.5 µg/kg, 1 µg/kg, 10 µg/kg, 100 µg/kg, 0.25 mg/kg, 1.0 mg/kg, 2.0 mg/kg, 5.0 mg/ml, 10 mg/kg, 25 mg/kg, 50 mg/kg or more (see, e.g., Yang, et al. (2003) *New Engl. J. Med.* 349:427-434; Herold, et al. (2002) *New Engl. J. Med.* 346:1692-1698; Liu, et al. (1999) *J. Neurol. Neurosurg. Psych.* 67:451-456; Portielji, et al. (20003) *Cancer Immunol. Immunother.* 52:151-144). Doses may also be provided to achieve a pre-determined target concentration of anti-CCL14 antibody in the subject's serum, such as 0.1, 0.3, 1, 3, 10, 30, 100, 300 µg/ml or more. In other embodiments, An anti-CCL14 antibody of the present invention is administered, e.g., subcutaneously or intravenously, on a weekly, biweekly, "every 4 weeks," monthly, bimonthly, or quarterly basis at 10, 20, 50, 80, 100, 200, 500, 1000 or 2500 mg/subject.

As used herein, the term "effective amount" refer to an amount of an anti-CCL14 or antigen-binding fragment thereof of the invention that, when administered alone or in combination with an additional therapeutic agent to a cell, tissue, or subject, is effective to cause a measurable improvement in one or more symptoms of disease, for example cancer or the progression of cancer. An effective dose further refers to that amount of the antibody or fragment sufficient to result in at least partial amelioration of symptoms, e.g., tumor shrinkage or elimination, lack of tumor growth, increased survival time. When applied to an individual active ingredient administered alone, an effective dose refers to that ingredient alone. When applied to a combination, an effective dose refers to combined amounts of the active ingredients that result in the therapeutic effect, whether administered in combination, serially or simultaneously. An effective amount of a therapeutic will result in an improvement of a diagnostic measure or parameter by at least 10%; usually by at least 20%; preferably at least about 30%; more preferably at least 40%, and most preferably by at least 50%. An effective amount can also result in an improvement in a subjective measure in cases where subjective measures are used to assess disease severity.

Kits

Further provided are kits comprising one or more components that include, but are not limited to, an anti-CCL14 antibody or antigen-binding fragment, as discussed herein in association with one or more additional components including, but not limited to a pharmaceutically acceptable carrier and/or a therapeutic agent, as discussed herein. The antibody or fragment and/or the therapeutic agent can be formulated as a pure composition or in combination with a pharmaceutically acceptable carrier, in a pharmaceutical composition.

In one embodiment, the kit includes an anti-CCL14 antibody or antigen-binding fragment thereof of the invention or a pharmaceutical composition thereof in one container (e.g., in a sterile glass or plastic vial) and a pharmaceutical composition thereof and/or a therapeutic agent in another container (e.g., in a sterile glass or plastic vial).

In another embodiment, the kit comprises a combination of the invention, including an anti-CCL14 antibody or antigen-binding fragment thereof of the invention along with a pharmaceutically acceptable carrier, optionally in combination with one or more therapeutic agents formulated together, optionally, in a pharmaceutical composition, in a single, common container.

If the kit includes a pharmaceutical composition for parenteral administration to a subject, the kit can include a device for performing such administration. For example, the kit can include one or more hypodermic needles or other injection devices as discussed above.

The kit can include a package insert including information concerning the pharmaceutical compositions and dosage forms in the kit. Generally, such information aids patients and physicians in using the enclosed pharmaceutical compositions and dosage forms effectively and safely. For example, the following information regarding a combination of the invention may be supplied in the insert: pharmacokinetics, pharmacodynamics, clinical studies, efficacy parameters, indications and usage, contraindications, warnings, precautions, adverse reactions, overdosage, proper dosage and administration, how supplied, proper storage conditions, references, manufacturer/distributor information and patent information.

As a matter of convenience, an anti-CCL14 antibody or antigen-binding fragment thereof of the invention can be provided in a kit, i.e., a packaged combination of reagents in predetermined amounts with instructions for performing the diagnostic or detection assay. Where the antibody or fragment is labeled with an enzyme, the kit will include substrates and cofactors required by the enzyme (e.g., a substrate precursor which provides the detectable chromophore or fluorophore). In addition, other additives may be included such as stabilizers, buffers (e.g., a block buffer or lysis buffer) and the like. The relative amounts of the various reagents may be varied widely to provide for concentrations in solution of the reagents which substantially optimize the sensitivity of the assay. Particularly, the reagents may be provided as dry powders, usually lyophilized, including excipients which on dissolution will provide a reagent solution having the appropriate concentration.

Also provided are diagnostic or detection reagents and kits comprising one or more such reagents for use in a variety of detection assays, including for example, immunoassays such as ELISA (sandwich-type or competitive format). The kit's components may be pre-attached to a solid support, or may be applied to the surface of a solid support when the kit is used. In some embodiments of the invention, the signal generating means may come pre-associated with an antibody or fragment of the invention or may require combination with one or more components, e.g., buffers, antibody-enzyme conjugates, enzyme substrates, or the like, prior to use. Kits may also include additional reagents, e.g., blocking reagents for reducing nonspecific binding to the solid phase surface, washing reagents, enzyme substrates, and the like. The solid phase surface may be in the form of a tube, a bead, a microtiter plate, a microsphere, or other materials suitable for immobilizing proteins, peptides, or polypeptides. In particular aspects, an enzyme that catalyzes the formation of a chemilluminescent or chromogenic product or the reduction of a chemilluminescent or chromogenic substrate is a component of the signal generating means. Such enzymes are well known in the art. Kits may comprise any of the capture agents and detection reagents described herein. Optionally the kit may also comprise instructions for carrying out the methods of the invention.

Also provided is a kit comprising an anti-CCL14 antibody (e.g., humanized antibody) or antigen-binding fragment thereof packaged in a container, such as a vial or bottle, and further comprising a label attached to or packaged with the container, the label describing the contents of the container and providing indications and/or instructions regarding use of the contents of the container to treat one or more disease states as described herein.

In one aspect, the kit is for treating cancer and comprises an anti-CCL14 antibody (e.g., humanized antibody) or antigen-binding fragment thereof and a further therapeutic agent or a vaccine. The kit may optionally further include a syringe for parenteral, e.g., intravenous, administration. In another aspect, the kit comprises an anti-CCL14 antibody (e.g., humanized antibody) or antigen-binding fragment thereof and a label attached to or packaged with the container describing use of the antibody or fragment with the vaccine or further therapeutic agent. In yet another aspect, the kit comprises the vaccine or further therapeutic agent and a label attached to or packaged with the container describing use of the vaccine or further therapeutic agent with the anti-CCL14 antibody or fragment. In certain embodiments, an anti-CCL14 antibody and vaccine or further therapeutic agent are in separate vials or are combined together in the same pharmaceutical composition.

As discussed above in the combination therapy section, concurrent administration of two therapeutic agents does not require that the agents be administered at the same time or by the same route, as long as there is an overlap in the time period during which the agents are exerting their therapeutic effect. Simultaneous or sequential administration is contemplated, as is administration on different days or weeks.

The therapeutic and detection kits disclosed herein may also be prepared that comprise at least one of the antibody, peptide, antigen-binding fragment, or polynucleotide disclosed herein and instructions for using the composition as a detection reagent or therapeutic agent. Containers for use in such kits may typically comprise at least one vial, test tube, flask, bottle, syringe or other suitable container, into which one or more of the detection and/or therapeutic composition(s) may be placed, and preferably suitably aliquoted. Where a second therapeutic agent is also provided, the kit may also contain a second distinct container into which this second detection and/or therapeutic composition may be placed. Alternatively, a plurality of compounds may be prepared in a single pharmaceutical composition, and may be packaged in a single container means, such as a vial, flask, syringe, bottle, or other suitable single container. The kits disclosed herein will also typically include a means for containing the vial(s) in close confinement for commercial sale, such as, e.g., injection or blow-molded plastic containers into which the desired vial(s) are retained. Where a radiolabel, chromogenic, fluorigenic, or other type of detectable label or detecting means is included within the kit, the labeling agent may be provided either in the same container as the detection or therapeutic composition itself, or may alternatively be placed in a second distinct container means into which this second composition may be placed and suitably aliquoted. Alternatively, the detection reagent and the label may be prepared in a single container means, and in most cases, the kit will also typically include a means for containing the vial(s) in close confinement for commercial sale and/or convenient packaging and delivery.

A device or apparatus for carrying out the detection or monitoring methods described herein is also provided. Such an apparatus may include a chamber or tube into which sample can be input, a fluid handling system optionally including valves or pumps to direct flow of the sample through the device, optionally filters to separate plasma or serum from blood, mixing chambers for the addition of capture agents or detection reagents, and optionally a detection device for detecting the amount of detectable label bound to the capture agent immunocomplex. The flow of sample may be passive (e.g., by capillary, hydrostatic, or other forces that do not require further manipulation of the device once sample is applied) or active (e.g., by application of force generated via mechanical pumps, electroosmotic pumps, centrifugal force, or increased air pressure), or by a combination of active and passive forces.

In further embodiments, also provided is a processor, a computer readable memory, and a routine stored on the computer readable memory and adapted to be executed on the processor to perform any of the methods described herein. Examples of suitable computing systems, environments, and/or configurations include personal computers, server computers, hand-held or laptop devices, multiprocessor systems, microprocessor-based systems, set top boxes, programmable consumer electronics, network PCs, minicomputers, mainframe computers, distributed computing environments that include any of the above systems or devices, or any other systems known in the art.

General Methods

Standard methods in molecular biology are described Sambrook, Fritsch and Maniatis (1982 & 1989 $2^{nd}$ Edition, 2001 $3^{rd}$ Edition) *Molecular Cloning, A Laboratory Manual*, Cold Spring Harbor Laboratory Press, Cold Spring Harbor, NY; Sambrook and Russell (2001) *Molecular Cloning, $3^{rd}$* ed., Cold Spring Harbor Laboratory Press, Cold Spring Harbor, NY; Wu (1993) *Recombinant DNA*, Vol. 217, Academic Press, San Diego, CA). Standard methods also appear in Ausbel, et al. (2001) *Current Protocols in Molecular Biology*, Vols. 1-4, John Wiley and Sons, Inc. New York, NY, which describes cloning in bacterial cells and DNA mutagenesis (Vol. 1), cloning in mammalian cells and yeast (Vol. 2), glycoconjugates and protein expression (Vol. 3), and bioinformatics (Vol. 4).

Methods for protein purification including immunoprecipitation, chromatography, electrophoresis, centrifugation, and crystallization are described (Coligan, et al. (2000) *Current Protocols in Protein Science*, Vol. 1, John Wiley and Sons, Inc., New York). Chemical analysis, chemical modification, post-translational modification, production of fusion proteins, glycosylation of proteins are described (see, e.g., Coligan, et al. (2000) *Current Protocols in Protein Science*, Vol. 2, John Wiley and Sons, Inc., New York; Ausubel, et al. (2001) *Current Protocols in Molecular Biology*, Vol. 3, John Wiley and Sons, Inc., NY, NY, pp. 16.0.5-16.22.17; Sigma-Aldrich, Co. (2001) *Products for Life Science Research*, St. Louis, MO; pp. 45-89; Amersham Pharmacia Biotech (2001) *BioDirectory*, Piscataway, N.J., pp. 384-391). Production, purification, and fragmentation of polyclonal and monoclonal antibodies are described (Coligan, et al. (2001) *Current Protcols in Immunology*, Vol. 1, John Wiley and Sons, Inc., New York; Harlow and Lane (1999) *Using Antibodies*, Cold Spring Harbor Laboratory Press, Cold Spring Harbor, NY; Harlow and Lane, supra). Standard techniques for characterizing ligand/receptor interactions are available (see, e.g., Coligan, et al. (2001) *Current Protocols in Immunology*, Vol. 4, John Wiley, Inc., New York).

Monoclonal, polyclonal, and humanized antibodies can be prepared (see, e.g., Sheperd and Dean (eds.) (2000) *Monoclonal Antibodies*, Oxford Univ. Press, New York, NY; Kontermann and Dubel (eds.) (2001) *Antibody Engineering*, Springer-Verlag, New York; Harlow and Lane (1988) *Antibodies A Laboratory Manual*, Cold Spring Harbor Laboratory Press, Cold Spring Harbor, NY, pp. 139-243; Carpenter, et al. (2000) *J. Immunol.* 165:6205; He, et al. (1998) *J. Immunol.* 160:1029; Tang et al. (1999) J. Biol. Chem. 274:27371-27378; Baca et al. (1997) *J. Biol. Chem.* 272: 10678-10684; Chothia et al. (1989) *Nature* 342:877-883; Foote and Winter (1992) *J. Mol. Biol.* 224:487-499; U.S. Pat. No. 6,329,511).

An alternative to humanization is to use human antibody libraries displayed on phage or human antibody libraries in transgenic mice (Vaughan et al. (1996) *Nature* Biotechnol. 14:309-314; Barbas (1995) *Nature Medicine* 1:837-839; Mendez et al. (1997) *Nature Genetics* 15:146-156; Hoogenboom and Chames (2000) *Immunol. Today* 21:371-377; Barbas et al. (2001) *Phage Display: A Laboratory Manual*, Cold Spring Harbor Laboratory Press, Cold Spring Harbor, New York; Kay et al. (1996) *Phage Display of Peptides and Proteins: A Laboratory Manual*, Academic Press, San Diego, CA; de Bruin et al. (1999) *Nature Biotechnol.* 17:397-399).

Single chain antibodies and diabodies are described (see, e.g., Malecki et al. (2002) *Proc. Natl. Acad. Sci. USA* 99:213-218; Conrath et al. (2001) *J. Biol. Chem.* 276:7346-7350; Desmyter et al. (2001) *J. Biol. Chem.* 276:26285-26290; Hudson and Kortt (1999) *J. Immunol. Methods* 231:177-189; and U.S. Pat. No. 4,946,778). Bifunctional antibodies are provided (see, e.g., Mack, et al. (1995) *Proc. Natl. Acad. Sci. USA* 92:7021-7025; Carter (2001) *J. Immunol. Methods* 248:7-15; Volkel, et al. (2001) *Protein Engineering* 14:815-823; Segal, et al. (2001) *J. Immunol. Methods* 248:1-6; Brennan, et al. (1985) *Science* 229:81-83; Raso, et al. (1997) *J. Biol. Chem.* 272:27623; Morrison (1985) *Science* 229:1202-1207; Traunecker, et al. (1991) *EMBO J.* 10:3655-3659; and U.S. Pat. Nos. 5,932,448, 5,532,210, and 6,129,914).

Multispecific antibodies are also provided (see, e.g., Azzoni et al. (1998) *J. Immunol.* 161:3493; Kita et al. (1999) *J. Immunol.* 162:6901; Merchant et al. (2000) *J. Biol. Chem.* 74:9115; Pandey et al. (2000) *J. Biol. Chem.* 275:38633; Zheng et al. (2001) *J. Biol Chem.* 276:12999; Propst et al. (2000) *J. Immunol.* 165:2214; Long (1999) *Ann. Rev. Immunol.* 17:875); Labrijin et al., Proc. Natl. Acad. Sci. USA 110: 5145-50, 2013; de Jong et al., PLOS Biol 14(1): e1002344, 2016 (doi:10.1371/journal.pbio.1002344). Purification of antigen is not necessary for the generation of antibodies. Animals can be immunized with cells bearing the antigen of interest. Splenocytes can then be isolated from the immunized animals, and the splenocytes can fused with a myeloma cell line to produce a hybridoma (see, e.g., Meyaard et al. (1997) *Immunity* 7:283-290; Wright et al. (2000) *Immunity* 13:233-242; Preston et al., supra; Kaithamana et al. (1999) *J. Immunol.* 163:5157-5164).

Antibodies can be conjugated, e.g., to small drug molecules, enzymes, liposomes, polyethylene glycol (PEG). Antibodies are useful for therapeutic, diagnostic, kit or other purposes, and include antibodies coupled, e.g., to dyes, radioisotopes, enzymes, or metals, e.g., colloidal gold (see, e.g., Le Doussal et al. (1991) *J. Immunol.* 146:169-175; Gibellini et al. (1998) *J. Immunol.* 160:3891-3898; Hsing and Bishop (1999) *J. Immunol.* 162:2804-2811; Everts et al. (2002) *J. Immunol.* 168:883-889).

Methods for flow cytometry, including fluorescence activated cell sorting (FACS), are available (see, e.g., Owens, et al. (1994) *Flow Cytometry Principles for Clinical Laboratory Practice*, John Wiley and Sons, Hoboken, NJ; Givan (2001) *Flow Cytometry,* 2$^{nd}$ed.; Wiley-Liss, Hoboken, NJ; Shapiro (2003) *Practical Flow Cytometry*, John Wiley and Sons, Hoboken, NJ). Fluorescent reagents suitable for modifying nucleic acids, including nucleic acid primers and probes, polypeptides, and antibodies, for use, e.g., as diagnostic reagents, are available (Molecular Probes (2003) *Catalogue*, Molecular Probes, Inc., Eugene, OR; Sigma-Aldrich (2003) *Catalogue*, St. Louis, MO).

Standard methods of histology of the immune system are described (see, e.g., Muller-Harmelink (ed.) (1986) *Human Thymus: Histopathology and Pathology*, Springer Verlag, New York, NY; Hiatt, et al. (2000) *Colo Atlas of Histology*, Lippincott, Williams, and Wilkins, Phila, PA; Louis, et al. (2002) *Basic Histology: Text and Atlas*, McGraw-Hill, New York, NY).

Software packages and databases for determining, e.g., antigenic fragments, leader sequences, protein folding, functional domains, glycosylation sites, and sequence alignments, are available (see, e.g., GenBank, Vector NTI® Suite (Informax, Inc, Bethesda, MD); GCG Wisconsin Package (Accelrys, Inc., San Diego, CA); DeCypher® (TimeLogic Corp., Crystal Bay, Nevada); Menne, et al. (2000) *Bioinformatics* 16: 741-742; Menne, et al. (2000) *Bioinformatics Applications Note* 16:741-742; Wren, et al. (2002) *Comput. Methods Programs Biomed.* 68:177-181; von Heijne (1983) *Eur. J. Biochem.* 133:17-21; von Heijne (1986) *Nucleic Acids Res.* 14:4683-4690).

The following are preferred embodiments of the invention:

1. A monoclonal antibody or antigen binding fragment thereof which specifically binds human CCL14, wherein the monoclonal antibody or antigen binding fragment wherein the antibody or antigen binding fragment comprises:

(i) a heavy chain variable region comprising
   a CDR1, CDR2, and CDR3 sequence from SEQ ID NO: 1,
   a CDR1, CDR2, and CDR3 sequence from SEQ ID NO: 3,
   a CDR1, CDR2, and CDR3 sequence from SEQ ID NO: 5,
   a CDR1, CDR2, and CDR3 sequence from SEQ ID NO: 7,
   a CDR1, CDR2, and CDR3 sequence from SEQ ID NO: 9,
   a CDR1, CDR2, and CDR3 sequence from SEQ ID NO: 11,
   a CDR1, CDR2, and CDR3 sequence from SEQ ID NO: 13,
   a CDR1, CDR2, and CDR3 sequence from SEQ ID NO: 15,
   a CDR1, CDR2, and CDR3 sequence from SEQ ID NO: 17, or
   a CDR1, CDR2, and CDR3 sequence from SEQ ID NO: 19; and (ii) a light chain variable region comprising
   a CDR1, CDR2, and CDR3 sequence from SEQ ID NO: 2, a CDR1, CDR2, and CDR3 sequence from SEQ ID NO: 4,
   a CDR1, CDR2, and CDR3 sequence from SEQ ID NO: 6,
   a CDR1, CDR2, and CDR3 sequence from SEQ ID NO: 8,
   a CDR1, CDR2, and CDR3 sequence from SEQ ID NO: 10,
   a CDR1, CDR2, and CDR3 sequence from SEQ ID NO: 12,
   a CDR1, CDR2, and CDR3 sequence from SEQ ID NO: 14,
   a CDR1, CDR2, and CDR3 sequence from SEQ ID NO: 16,
   a CDR1, CDR2, and CDR3 sequence from SEQ ID NO: 18, or
   a CDR1, CDR2, and CDR3 sequence from SEQ ID NO: 20.

2. A monoclonal antibody or antigen binding fragment according to embodiment 1, wherein the antibody comprises
   a heavy chain variable region comprising a CDR1, CDR2, and CDR3 sequence from SEQ ID NO: 1, and a light chain variable region comprising a CDR1, CDR2, and CDR3 sequence from SEQ ID NO: 2 (2H3/2K1),
   a heavy chain variable region comprising a CDR1, CDR2, and CDR3 sequence from SEQ ID NO: 3, and a light chain variable region comprising a CDR1, CDR2, and CDR3 sequence from SEQ ID NO: 4 (3H1/3K1),
   a heavy chain variable region comprising a CDR1, CDR2, and CDR3 sequence from SEQ ID NO: 5, and a light chain variable region comprising a CDR1, CDR2, and CDR3 sequence from SEQ ID NO: 6 (4H1/4K3),
   a heavy chain variable region comprising a CDR1, CDR2, and CDR3 sequence from SEQ ID NO: 7, and a light chain variable region comprising a CDR1, CDR2, and CDR3 sequence from SEQ ID NO: 8 (10H3/10K1),
   a heavy chain variable region comprising a CDR1, CDR2, and CDR3 sequence from SEQ ID NO: 9, and a light chain variable region comprising a CDR1, CDR2, and CDR3 sequence from SEQ ID NO: 10 (12H2/12K1),
   a heavy chain variable region comprising a CDR1, CDR2, and CDR3 sequence from SEQ ID NO: 11, and a light chain variable region comprising a CDR1, CDR2, and CDR3 sequence from SEQ ID NO: 12 (17H2/17K1),
   a heavy chain variable region comprising a CDR1, CDR2, and CDR3 sequence from SEQ ID NO: 13, and a light chain variable region comprising a CDR1, CDR2, and CDR3 sequence from SEQ ID NO: 14 (18H1/18K1),
   a heavy chain variable region comprising a CDR1, CDR2, and CDR3 sequence from SEQ ID NO: 15, and a light chain variable region comprising a CDR1, CDR2, and CDR3 sequence from SEQ ID NO: 16 (19H2/19K3),
   a heavy chain variable region comprising a CDR1, CDR2, and CDR3 sequence from SEQ ID NO: 17, and a light chain variable region comprising a CDR1, CDR2, and CDR3 sequence from SEQ ID NO: 18 (25H2/25K1), or a heavy chain variable region comprising a CDR1, CDR2, and CDR3 sequence from SEQ ID NO: 19, and a light chain variable region comprising a CDR1, CDR2, and CDR3 sequence from SEQ ID NO: 20 (31H1/31K1).

3. A monoclonal antibody or antigen binding fragment according to embodiment 1, wherein the antibody comprises a heavy chain variable region of SEQ ID NO: 1 or a corresponding heavy chain variable region having at least 90% sequence similarity to the framework region thereof, and a light chain variable region of SEQ ID NO: 2 or a corresponding light chain variable region having at least 90% sequence similarity to the framework region thereof (2H3/2K1).

a heavy chain variable region of SEQ ID NO: 3 or a corresponding heavy chain variable region having at least 90% sequence similarity to the framework region thereof, and a light chain variable region of SEQ ID NO: 4 or a corresponding light chain variable region having at least 90% sequence similarity to the framework region thereof (3H1/3K1), a heavy chain variable region of SEQ ID NO: 5 or a corresponding heavy chain variable region having at least 90% sequence similarity to the framework region thereof, and a light chain variable region of SEQ ID NO: 6 a corresponding light chain variable region having at least 90% sequence similarity to the framework region thereof (4H1/4K3), a heavy chain variable region of SEQ ID NO: 7 or a corresponding heavy chain variable region having at least 90% sequence similarity to the framework region thereof, and a light chain variable region of SEQ ID NO: 8 a corresponding light chain variable region having at least 90% sequence similarity to the framework region thereof (10H3/10K1), a heavy chain variable region of SEQ ID NO: 9 or a corresponding heavy chain variable region having at least 90% sequence similarity to the framework region thereof, and a light chain variable region of SEQ ID NO: 10 a corresponding light chain variable region having at least 90% sequence similarity to the framework region thereof (12H2/12K1), a heavy chain variable region of SEQ ID NO: 11 or a corresponding heavy chain variable region having at least 90% sequence similarity to the framework region thereof, and a light chain variable region of SEQ ID NO: 12 a corresponding light chain variable region having at least 90% sequence similarity to the framework region thereof (17H2/17K1), a heavy chain variable region of SEQ ID NO: 13 or a corresponding heavy chain variable region having at least 90% sequence similarity to the framework region thereof, and a light chain variable region of SEQ ID NO: 14 a corresponding light chain variable region having at least 90% sequence similarity to the framework region thereof (18H1/18K1), a heavy chain variable region of SEQ ID NO: 15 or a corresponding heavy chain variable region having at least 90% sequence similarity to the framework region thereof, and a light chain variable region of SEQ ID NO: 16 a corresponding light chain variable region having at least 90% sequence similarity to the framework region thereof (19H2/19K3), a heavy chain variable region of SEQ ID NO: 17 or a corresponding heavy chain variable region having at least 90% sequence similarity to the framework region thereof, and a light chain variable region of SEQ ID NO: 18 a corresponding heavy chain variable region having at least 90% sequence similarity to the framework region thereof (25H2/25K1), or a heavy chain variable region of SEQ ID NO: 19 or a corresponding heavy chain variable region having at least 90% sequence similarity to the framework region thereof, and a light chain variable region of SEQ ID NO: 20 a corresponding light chain variable region having at least 90% sequence similarity to the framework region thereof (31H1/31K1).

4. A monoclonal antibody or antigen binding fragment according to one of embodiments 1-3, wherein the antibody is conjugated to a signal development element.

5. A monoclonal antibody or antigen binding fragment according to one of embodiments 1-3, wherein the antibody is immobilized on a solid support.

6. A monoclonal antibody or antigen binding fragment according to one of embodiments 1-5 which is an F(ab) and F(ab')2 fragment.

7. A kit comprising:

a first monoclonal antibody or antigen binding fragment according to one of embodiments 1-5, and a second monoclonal antibody or antigen binding fragment which specifically binds human CCL14, wherein the first antibody or antigen binding fragment and the second antibody or antigen binding fragment form sandwich complexes with human CCL14.

8. A kit according to embodiment 7, wherein the second antibody or antigen binding fragment is an isolated monoclonal antibody or antigen binding fragment according to one of embodiments 1-5 that is different from the first monoclonal antibody or antigen binding fragment.

9. A kit according to one of embodiments 7 or 8, further comprising a disposable test device configured to generate a detectable signal related to the presence or amount of human CCL14 in a biological sample, wherein the first antibody or antigen binding fragment or the second antibody or antigen binding fragment is immobilized on a surface within the disposable test device.

10. A kit according to embodiment 9, wherein the disposable test device is a lateral flow test device.

11. A kit according to one of embodiments 9 or 10, wherein the first antibody or antigen binding fragment is immobilized to a surface within the disposable test device, and the second antibody or antigen binding fragment is conjugated to a detectable label.

12. A kit according to one of embodiments 7 or 8, wherein the first antibody or antigen binding fragment is immobilized to a surface within the disposable test device, and the second antibody or antigen binding fragment is conjugated to a detectable label and is provided in a separate container from the disposable test device.

13. A kit according to one of embodiments 7-10, wherein the kit further comprises a calibration to relate the detectable signal to a concentration of CCL14.

14. A kit according to embodiment 13, wherein the calibration is a calibration curve provided on an electronic memory device.

15. A kit according to one of embodiments 7-14, wherein the kit is configured to perform an assay method which provides a signal related to the presence or amount of human CCL14 in a biological sample, and wherein the minimum detectable concentration of CCL14 in the assay method is 10 ng/mL or less.

16. A kit according to one of embodiments 7-15, wherein the first and second monoclonal antibodies or antigen binding fragments thereof in the kit are a pair selected from the group consisting of a 10H3/10K1-2H3/2K1 pair, a 10H3/10K1-31H1/31K1 pair, an 18H1/18K1-31H1/31K1 pair, and an 18H1/18K1-2H3/2K1 pair, which in each case the antibody may be the corresponding antigen binding fragment thereof.

17. A kit according to one of embodiments 7-16, wherein one of the first or second monoclonal antibodies or antigen binding fragment thereof binds to an epitope on human CCL14 that comprises all or part of the sequence HSVCTNPSDKWVQDYI (SEQ ID NO: 23); and wherein the other of the first or second monoclonal antibodies or antigen binding fragment thereof binds to an epitope on human CCL14 that comprises all or part of the sequence ECCFTYTTYKIPR (SEQ ID NO: 27), TNSQCSKPG (SEQ ID NO: 28) or CCFTYT-TYKIPRQR (SEQ ID NO: 24).

18. A kit according to one of embodiments 6-17, wherein one of the first or second monoclonal antibodies or antigen binding fragment thereof is 10H3/10K1 or antigen binding fragment thereof; and wherein the other of the first or second monoclonal antibodies or antigen binding fragment thereof is 31H1/31K1 or 2H3/2K1 or antigen binding fragment thereof.

19. A kit according to one of embodiments 6-18, wherein one or both of the first or second monoclonal antibodies or antigen binding fragment thereof is an F(ab) and F(ab')2 fragment.

20. A kit according to one of embodiments 6-19, wherein one or both of the first or second monoclonal antibodies or antigen binding fragment thereof is a rabbit antibody or an antigen binding fragment thereof.

21. A monoclonal antibody or antigen binding fragment according to embodiment 1-6, wherein the monoclonal antibody or antigen binding fragment is a rabbit antibody or an antigen binding fragment thereof.

22. A method for determining the presence or amount of human CCL14 in a biological sample, comprising: performing an immunoassay on the biological sample with a first monoclonal antibody or antigen binding fragment thereof and a second monoclonal antibody or antigen binding fragment thereof which together form sandwich complexes with human CCL14, wherein the immunoassay provides a detectable signal that is related to the presence or amount of human CCL14 in the biological sample bound in the sandwich complexes; and relating the detectable signal to the presence or amount of human CCL14 in the biological sample, wherein the first monoclonal antibody or antigen binding fragment, and optionally the second monoclonal antibody or antigen binding fragment, is an antibody according to one of embodiments 1-6 or 21.

23. A method according to embodiment 22, wherein the minimum detectable concentration of CCL14 in the immunoassay is 10 ng/mL or less.

24. A method according to one of embodiments 22 or 23, wherein the immunoassay is performed in a lateral flow format.

25. A method according to one of embodiments 22-24, wherein the immunoassay is an in vitro diagnostic.

26. A method according to one of embodiments 22-25, wherein the immunoassay is performed by applying the human patient sample to a disposable test device, and the detectable signal is obtained by inserting the disposable test device into an analytical instrument, wherein the sandwich complexes comprising the first and second antibodies or antigen binding fragments are immobilized for detection in a predetermined zone of the disposable test device, and wherein the analytical instrument detects the immobilized sandwich complexes to provide the detectable signal.

27. A method according to one of embodiments 22-26, wherein the first antibody or antigen binding fragment is conjugated to a signal development element.

28. A method according to embodiment 27, wherein the first antibody or antigen binding fragment forms a reaction mixture with the human patient sample, and the human patient sample is applied to the disposable test device by applying the reaction mixture to the disposable test device.

29. A method according to embodiment 27 or 28, wherein the second antibody or antigen binding fragment is immobilized at the predetermined zone of a solid support.

30. A method according to one of embodiments 22-29, wherein each of the first and second antibodies or antigen binding fragments is a rabbit, mouse, chicken, goat, sheep, donkey, human, llama or camelid antibody or antigen binding fragment thereof.

31. A method according to embodiment 30, wherein at least one of the first and second antibodies or antigen binding fragments is a rabbit antibody or antibody fragment.

32. A method according to one of embodiments 22-31, wherein one or both of the first or second monoclonal antibodies or antigen binding fragment thereof is an F(ab) and F(ab')2 fragment.

33. A method according to one of embodiments 22-32, wherein the first monoclonal antibody or antigen binding fragment thereof binds to an epitope on human CCL14 that comprises all or part of the sequence HSVCTNPSDKWVQDYI (SEQ ID NO: 23), CCFTYTTYKIPRQR (SEQ ID NO: 24), DKWVQDYIKDMK (SEQ ID NO: 25), MDYY-ETNSQCSK (SEQ ID NO: 26), ECCFTYTTYKIPR (SEQ ID NO: 27), TNSQCSKPG (SEQ ID NO: 28), or ETNSQCSKP (SEQ ID NO: 29); and wherein the second monoclonal antibody or antigen binding fragment thereof binds to an epitope on human CCL14 that comprises all or part of the sequence HSVCTNPSDKWVQDYI (SEQ ID NO: 23), CCFTYTTYKIPRQR (SEQ ID NO: 24), DKWVQDYIKDMK (SEQ ID NO: 25), MDYY-ETNSQCSK (SEQ ID NO: 26), ECCFTYTTYKIPR (SEQ ID NO: 27), TNSQCSKPG (SEQ ID NO: 28), or ETNSQCSKP (SEQ ID NO: 29) and forms a sandwich complex with CCL14 and the first monoclonal antibody or antigen binding fragment thereof.

34. A method according to one of embodiments 22-33, wherein the first monoclonal antibody or antigen binding fragment thereof binds to an epitope on human CCL14 that comprises all or part of the sequence HSVCTNPSDKWVQDYI (SEQ ID NO: 23); and wherein the second monoclonal antibody or antigen binding fragment thereof binds to an epitope on human CCL14 that comprises all or part of the sequence ECCFTYTTYKIPR (SEQ ID NO: 27), TNSQCSKPG (SEQ ID NO: 28) or CCFTYTTYKIPRQR (SEQ ID NO: 24).

35. A method according to one of embodiments 22-34, wherein the first and second monoclonal antibodies or antigen binding fragments thereof are a pair selected from the group consisting of a 10H3/10K1-2H3/2K1 pair, a 10H3/10K1-31H1/31K1 pair, an 18H1/18K1-31H1/31K1 pair, and an 18H1/18K1-2H3/2K1 pair, which in each case the antibody may be the corresponding antigen binding fragment thereof.

36. A method according to one of embodiments 22-35, wherein one of the first or second monoclonal antibodies or antigen binding fragment thereof is 10H3/10K1 or antigen binding fragment thereof; and wherein the other of the first or second monoclonal antibodies or antigen binding fragment thereof is 31H1/31K1 or antigen binding fragment thereof or 2H3/2K1 or antigen binding fragment thereof.

37. A method for determining the presence or amount of human CCL14 in a biological sample, comprising:
performing an immunoassay on the biological sample with a monoclonal antibody or antigen binding fragment thereof which binds human CCL14, wherein the immunoassay provides a detectable signal that is related to the presence or amount of human CCL14 in the biological sample; and
relating the detectable signal to the presence or amount of human CCL14 in the biological sample, wherein the assay is a competitive assay and the monoclonal antibody or antigen
binding fragment is an antibody according to one of embodiments 1-6 or 21 or an antigen binding fragment thereof.

38. A monoclonal antibody or antigen binding fragment comprising:
a heavy chain variable region comprising a CDR1, CDR2, and CDR3 sequence from SEQ ID NO: 1, and a light chain variable region comprising a CDR1, CDR2, and CDR3 sequence from SEQ ID NO: 2 (2H3/2K1), wherein the heavy chain variable region has at least 90% sequence similarity within the framework sequences to the framework sequences of SEQ ID NO: 1, and the light chain variable region has at least 90% sequence similarity within the framework sequences to the framework sequences of SEQ ID NO: 2.

39. A monoclonal antibody or antigen binding fragment comprising:
a heavy chain variable region comprising a CDR1, CDR2, and CDR3 sequence from SEQ ID NO: 3, and a light chain variable region comprising a CDR1, CDR2, and CDR3 sequence from SEQ ID NO: 4 (3H1/3K1), wherein the heavy chain variable region has at least 90% sequence similarity within the framework sequences to the framework sequences of SEQ ID NO: 3, and the light chain variable region has at least 90% sequence similarity within the framework sequences to the framework sequences of SEQ ID NO: 4.

40. A monoclonal antibody or antigen binding fragment comprising:
a heavy chain variable region comprising a CDR1, CDR2, and CDR3 sequence from SEQ ID NO: 5, and a light chain variable region comprising a CDR1, CDR2, and CDR3 sequence from SEQ ID NO: 6 (4H1/4K3), wherein the heavy chain variable region has at least 90% sequence similarity within the framework sequences to the framework sequences of SEQ ID NO: 5, and the light chain variable region has at least 90% sequence similarity within the framework sequences to the framework sequences of SEQ ID NO: 6.

41. A monoclonal antibody or antigen binding fragment comprising:
a heavy chain variable region comprising a CDR1, CDR2, and CDR3 sequence from SEQ ID NO: 7, and a light chain variable region comprising a CDR1, CDR2, and CDR3 sequence from SEQ ID NO: 8 (10H3/10K1), wherein the heavy chain variable region has at least 90% sequence similarity within the framework sequences to the framework sequences of SEQ ID NO: 7, and the light chain variable region has at least 90% sequence similarity within the framework sequences to the framework sequences of SEQ ID NO: 8.

42. A monoclonal antibody or antigen binding fragment comprising:
a heavy chain variable region comprising a CDR1, CDR2, and CDR3 sequence from SEQ ID NO: 9, and a light chain variable region comprising a CDR1, CDR2, and CDR3 sequence from SEQ ID NO: 10 (12H2/12K1), wherein the heavy chain variable region has at least 90% sequence similarity within the framework sequences to the framework sequences of SEQ ID NO: 9, and the light chain variable region has at least 90% sequence similarity within the framework sequences to the framework sequences of SEQ ID NO: 10.

43. A monoclonal antibody or antigen binding fragment comprising:
a heavy chain variable region comprising a CDR1, CDR2, and CDR3 sequence from SEQ ID NO: 11, and a light chain variable region comprising a CDR1, CDR2, and CDR3 sequence from SEQ ID NO: 12 (17H2/17K1), wherein the heavy chain variable region has at least 90% sequence similarity within the framework sequences to the framework sequences of SEQ ID NO: 11, and the light chain variable region has at least 90% sequence similarity within the framework sequences to the framework sequences of SEQ ID NO: 12.

44. A monoclonal antibody or antigen binding fragment comprising:
a heavy chain variable region comprising a CDR1, CDR2, and CDR3 sequence from SEQ ID NO: 13, and a light chain variable region comprising a CDR1, CDR2, and CDR3 sequence from SEQ ID NO: 14 (18H1/18K1), wherein the heavy chain variable region has at least 90% sequence similarity within the framework sequences to the framework sequences of SEQ ID NO: 13, and the light chain variable region has at least 90% sequence similarity within the framework sequences to the framework sequences of SEQ ID NO: 14.

45. A monoclonal antibody or antigen binding fragment comprising:
a heavy chain variable region comprising a CDR1, CDR2, and CDR3 sequence from SEQ ID NO: 15, and a light chain variable region comprising a CDR1, CDR2, and CDR3 sequence from SEQ ID NO: 16 (19H2/19K3), wherein the heavy chain variable region has at least 90% sequence similarity within the framework sequences to the framework sequences of SEQ ID NO: 15, and the light chain variable region has at least 90% sequence similarity within the framework sequences to the framework sequences of SEQ ID NO: 16.

46. A monoclonal antibody or antigen binding fragment comprising:

a heavy chain variable region comprising a CDR1, CDR2, and CDR3 sequence from SEQ ID NO: 17, and a light chain variable region comprising a CDR1, CDR2, and CDR3 sequence from SEQ ID NO: 18 (25H2/25K1), wherein the heavy chain variable region has at least 90% sequence similarity within the framework sequences to the framework sequences of SEQ ID NO: 17, and the light chain variable region has at least 90% sequence similarity within the framework sequences to the framework sequences of SEQ ID NO: 18.

47. A monoclonal antibody or antigen binding fragment comprising:

a heavy chain variable region comprising a CDR1, CDR2, and CDR3 sequence from SEQ ID NO: 19, and a light chain variable region comprising a CDR1, CDR2, and CDR3 sequence from SEQ ID NO: 20 (31H1/31K1), wherein the heavy chain variable region has at least 90% sequence similarity within the framework sequences to the framework sequences of SEQ ID NO: 19, and the light chain variable region has at least 90% sequence similarity within the framework sequences to the framework sequences of SEQ ID NO: 20.

48. A pair of monoclonal antibodies or antigen binding fragments comprising:

a first monoclonal antibody or antigen binding fragment according to one of embodiments 38-47; and a second monoclonal antibody or antigen binding fragment according to one of embodiments 38-47 that differs from the first monoclonal antibody or antigen binding fragment.

49. A monoclonal antibody or antigen binding fragment pair selected from the group consisting of a 10H3/10K1-2H3/2K1 pair, a 10H3/10K1-31H1/31K1 pair, an 18H1/18K1-31H1/31K1 pair, and an 18H1/18K1-2H3/2K1 pair, which in each case the antibody may be the corresponding antigen binding fragment thereof.

50. A monoclonal antibody or antigen binding fragment which specifically binds human CCL14 and that binds to an epitope on human CCL14 that comprises all or part of the sequence HSVCTNPSDKWVQDYI (SEQ ID NO: 23).

51. A monoclonal antibody or antigen binding fragment according to embodiment 50, wherein the monoclonal antibody or antigen binding fragment comprises a heavy chain variable region of SEQ ID NO: 7 or a corresponding heavy chain variable region having at least 90% sequence similarity to the framework region thereof, and a light chain variable region of SEQ ID NO: 8 a corresponding light chain variable region having at least 90% sequence similarity to the framework region thereof (10H3/10K1).

52. A monoclonal antibody or antigen binding fragment according to embodiment 51, wherein the monoclonal antibody is 10H3/10K1, an antigen binding fragment thereof, an F(ab) fragment thereof, or an F(ab')2 fragment thereof.

53. A kit comprising the monoclonal antibody or antigen binding fragment thereof of one of embodiments 50-52, and a second monoclonal antibody or antigen binding fragment which specifically binds h40man CCL14 and that binds to an epitope on human CCL14 that comprises all or part of the sequence CCFTYTTYKIPRQR (SEQ ID NO: 24), DKWVQDYIKDMK (SEQ ID NO: 25), MDYYETNSQCSK (SEQ ID NO: 26), ECCFTYTTYKIPR (SEQ ID NO: 27), TNSQCSKPG (SEQ ID NO: 28), or ETNSQCSKP (SEQ ID NO: 29), wherein the monoclonal antibody or antigen binding fragment thereof and the second antibody or antigen binding fragment thereof form sandwich complexes with human CCL14.

54. A kit according to one of embodiments 50-53, wherein the monoclonal antibody or antigen binding fragment thereof binds to an epitope on human CCL14 that comprises all or part of the sequence HSVCTNPSDKWVQDYI (SEQ ID NO: 23); and wherein the second monoclonal antibody or antigen binding fragment thereof binds to an epitope on human CCL14 that comprises all or part of the sequence ECCFTYTTYKIPR (SEQ ID NO: 27), TNSQCSKPG (SEQ ID NO: 28) or CCFTYTTYKIPRQR (SEQ ID NO: 24).

55. A kit according to one of embodiments 50-54, wherein the first and second monoclonal antibodies or antigen binding fragment thereof are a pair of antibodies selected from the group consisting of a 10H3/10K1-2H3/2K1 pair, a 10H3/10K1-31H1/31K1 pair, an 18H1/18K1-31H1/31K1 pair, and an 18H1/18K1-2H3/2K1 pair, which in each case the antibody may be the corresponding antigen binding fragment thereof.

56. A kit according to embodiment 55, wherein one of the first or second monoclonal antibodies or antigen binding fragment thereof is 10H3/10K1 or antigen binding fragment thereof; and wherein the other of the first or second monoclonal antibodies is 31H1/31K1 or 2H3/2K1 or an antigen binding fragment thereof.

57. A kit according to embodiment 53, wherein the second monoclonal antibody or antigen binding fragment thereof comprises a heavy chain variable region of SEQ ID NO: 19 or a corresponding heavy chain variable region having at least 90% sequence similarity to the framework region thereof, and a light chain variable region of SEQ ID NO: 20 a corresponding light chain variable region having at least 90% sequence similarity to the framework region thereof (31H1/31K1).

58. A kit according to embodiment 58, wherein the monoclonal antibody or antigen binding fragment thereof is 10H3/10K1 or antigen binding fragment thereof; and wherein the second monoclonal antibody or antigen binding fragment thereof is 31H1/31K1 or antigen binding fragment thereof.

59. A kit according to embodiment 53, wherein the second monoclonal antibody or antigen binding fragment thereof comprises a heavy chain variable region of SEQ ID NO: 1 or a corresponding heavy chain variable region having at least 90% sequence similarity to the framework region thereof, and a light chain variable region of SEQ ID NO: 2 a corresponding light chain variable region having at least 90% sequence similarity to the framework region thereof (2H3/2K1).

60. A kit according to embodiment 59, wherein the monoclonal antibody or antigen binding fragment thereof is 10H3/10K1 or antigen binding fragment thereof; and wherein the second monoclonal antibody or antigen binding fragment thereof is 2H3/2K1 or antigen binding fragment thereof.

61. A kit according to one of embodiments 53-60, wherein one or both of the first or second monoclonal antibodies or antigen binding fragment thereof is an F(ab) or F(ab')2 fragment.

EXAMPLES

Example 1: Monoclonal Antibody Development in Rabbits

Female New Zealand Rabbits were immunized by subcutaneous injections (SQ) with antigen/adjuvant emulsions. Primary immunization was done with Complete Freund's Adjuvant and Incomplete Freund's Adjuvant was used for all subsequent boosts. Rabbits were injected SQ every three weeks at 250 µg CCL14 antigen per rabbit (alternating two sites, hips and scapulas). A test bleed was taken from the marginal ear vein seven days after the second boost. This test bleed (immune sera) was tested by indirect ELISA assay to determine if immune response of the rabbit was adequate for monoclonal antibody development. Responding rabbits were given a final SQ boost and four days later was euthanized via exsanguination. The whole blood was collected via cardiac puncture. B cells producing antibody of interest were identified by indirect ELISA on target antigen and immunoglobulin genes were isolated. Heavy and light chains were cloned into separate mammalian expression vectors, transfected into HEK cells (transient transfection), and tissue culture supernatant containing rabbit monoclonal antibodies were harvested. Heavy and light chain sequences were obtained by DNA sequencing.

Example 2: Epitope Mapping of Monoclonal Antibodies to CCL14

The epitopes of various monoclonal antibodies of the invention, and commercially available antibodies AF324 and MAB3241 (R&D Systems), were mapped using linear, conformational, and discontinuous mapping methods. AF324 is a polyclonal goat antibody, and MAB3241 is a mouse monoclonal antibody.

The concept of mapping linear epitopes using libraries of overlapping synthetic peptides was pioneered by Geysen and Meloen (PNAS 81: 3998-4002, 1984). Linear peptides were synthesized directly on a solid support covered with a proprietary hydrogel formulation.

To generate a first peptide library, the amino acid sequence of the CCL14 protein was first split int overlapping 15 residue fragments in silico with an offset of one residue, which were then synthesized on a solid support.

In a second library of peptides derived from the first library, each residue in a fragment at positions 10 and 11 were replaced by alanine (unless the native residue was alanine, in which case it is replaced by glycine).

In a third library of peptides derived from the first library, each cysteine is replaced by a Cys-acetamidomethyl residue.

For a fourth library of peptides, the amino acid sequence of the CCL14 protein was first split int overlapping 25 residue fragments in silico with an offset of one residue, which were then synthesized on a solid support.

For a fifth library, constrained peptides of length 17 were generated. On positions 2-16 are 15-mer peptides derived from the target sequence of CCL14 with an offset of one residue. Cys residues were inserted on positions 1 and 17 and joined by mP2 CLIPS in order to create a loop mimic. Native Cys are replaced by a Cys-acetamidomethyl residue.

For a sixth library, constrained peptides of length 21 were generated. On positions 2-16 are 19-mer peptides derived from the target sequence of CCL14 with an offset of one residue. Cys residues were inserted on positions 1 and 21 and joined by mP2 CLIPS in order to create a loop mimic. Native Cys are replaced by a Cys-acetamidomethyl residue.

For a seventh library, constrained peptides of length 27 were generated. On positions 2-26 are 25-mer peptides derived from the target sequence of CCL14 with an offset of one residue. Cys residues were inserted on positions 1 and 27 and joined by mP2 CLIPS in order to create a loop mimic. Native Cys are replaced by a Cys-acetamidomethyl residue.

For an eighth library, β-turn epitope mimics of length 22 were generated. On positions 2-21 are 20-mer peptides derived from the target sequence of CCL14 with an offset of one residue. Residues on positions 11 and 12 are replaced by a "PG" motif in order to induce the β-turn formation. Cys residues were inserted on positions 1 and 22 and joined by mP2 CLIPS in order to stabilize the mimic. Native Cys are replaced by a Cys-acetamidomethyl residue.

For a ninth library, α-helical epitope mimics of length 22 were generated. Cys residues were inserted on positions 1 and 5 in order to nucleate an α-helical turn using mP2 CLIPS. Cys residues were inserted on positions 1 and 22 and joined by mP2 CLIPS in order to stabilize the mimic. Native Cys are replaced by a Cys-acetamidomethyl residue.

For a tenth library, peptides of length 25 derived from the CCL14 were generated. Each 25-mer peptide contains a pair of cysteine residues that are indicated to form a disulfide bridge as per UniProt information on post-translational modification of CCL14. Cys residues not participating in the disulfide bridge formation are replaced by a Cys-acetamidomethyl residue.

For an eleventh library, peptides of length 27 derived from the CCL14 were generated. Each 27-mer is composed of two 11-mer peptides joined via "GGSGG" linker. Two combined 11-mers contain a pair of cysteine residues that are indicated to form a disulfide bridge as per UniProt information on post-translational modification of CCL14. Cys residues not participating in the disulfide bridge formation are replaced by a Cys-acetamidomethyl residue.

For a twelfth library, bicyclic peptides of length 27 were generated. On positions 2-13 and 15-26 are 12-mer peptides derived from the sequence of CCL14. Cys residues are inserted on positions 1, 14 and 27 in order to create a discontinuous mimic by means of T3 CLIPS. Native Cys are replaced by a Cys-acetamidomethyl residue.

For a thirteenth library, bicyclic peptides of length 33 were generated. On positions 2-16 and 18-32 are 15-mer peptides derived from the sequence of CCL14. Cys residues are inserted on positions 1, 17 and 33 in order to create a discontinuous mimic by means of T3 CLIPS. Native Cys are replaced by a Cys-acetamidomethyl residue.

Antibodies were diluted in buffer and applied to the peptide library array. Each antibody tested was optimized for the array by testing different blocking conditions and sample concentration. Results were analyzed and binding events were noted with at least three times the median value. Epitope mapping was precluded in the case of antibodies showing high binding signals throughout the array.

Based on binding to the array, the following CCL14 epitopes were identified for antibodies of the present invention:

| Clone | Epitope |
|---|---|
| 10H3/10K1 | HSVCTNPSDKWVQDYI (SEQ ID NO: 23) |
| 31H1/31K1 | CCFTYTTYKIPRQR (SEQ ID NO: 24) |
| 25H2/25K1 | DKWVQDYIKDMK (SEQ ID NO: 25) and MDYYETNSQCSK (SEQ ID NO: 26) |

-continued

| Clone | Epitope |
|---|---|
| 2H3/2K1 | ECCFTYTTYKIPR (SEQ ID NO: 27) and<br>TNSQCSKPG (SEQ ID NO: 28) |
| 19H2/19K3 | ETNSQCSKP (SEQ ID NO: 29) |
| AF324 (goat<br>polyclonal) | KTESSSRGPYHPSE (SEQ ID NO: 30)<br>and YTTYKIPRQRIM (SEQ ID NO: 31) |
| MAB3241 (mouse<br>monoclonal) | CCFTYTTYKIPRQR (SEQ ID NO: 24) |

Example 3. Antibody Pairing

Various antibodies of the invention were tested for their ability to form sandwich complexes in a lateral flow format. Urine was used as a sample matrix for CCL14 antigen standards. One member of the antibody pair (the "strip" antibody) was immobilized onto a nitrocellulose membrane, and the other member of the antibody pair was prepared as a labeled conjugate with a label that is detectable by the ASTUTE 140® meter system for reading to the test strip.

CCL14 standard was prepared using R&D Systems catalog number 324-HC to the following target concentrations (all ng/mL): 20, 5, 2, 0.5, and 0.2. antibodies tested were 2H3/2K1, 31H1/31K1, 18H1/18K1, and 10H3/10K1. Pairing results are shown in FIG. 3.

To further understand the ability of the antibodies of the present invention to pair, a matrix of various antibodies was analyzed at a single CCL14 concentration of 5 ng/mL in a 100 μL sample volume. The solid phase "strip" antibody was applied to nitrocellulose in 3 μL of a 0.25 μg/mL solution. The conjugate was mixed with the sample volume to a concentration of 10 μg/mL. The following pairings were observed:

| | 2H3/2K1<br>Strip | 3H1/3K1<br>Strip | 31H1/31K1<br>Strip | 12H2/12K1<br>Strip | AF324<br>Strip |
|---|---|---|---|---|---|
| 4H1/4K3<br>Conjugate | Yes | Yes | Yes | Yes | Yes |
| 17H2/17K1<br>Conjugate | Yes | Yes | Yes | Yes | Yes |
| 18H1/18K1<br>Conjugate | Yes | Yes | Yes | Yes | Yes |
| 19H2/19K3<br>Conjugate | Yes | Yes | Yes | Yes | Yes |
| 25H2/25K1<br>Conjugate | Yes | Yes | Yes | Yes | Yes |
| 10H3/10K1<br>Conjugate | Yes | Yes | Yes | Yes | Yes |

While the invention has been described and exemplified in sufficient detail for those skilled in this art to make and use it, various alternatives, modifications, and improvements should be apparent without departing from the spirit and scope of the invention. The examples provided herein are representative of preferred embodiments, are exemplary, and are not intended as limitations on the scope of the invention. Modifications therein and other uses will occur to those skilled in the art. These modifications are encompassed within the spirit of the invention and are defined by the scope of the claims.

The use of "or" herein means "and/or" unless stated otherwise. Similarly, "comprise," "comprises," "comprising" "include," "includes," and "including" are interchangeable and not intended to be limiting.

It is to be further understood that where descriptions of various embodiments use the term "comprising," those skilled in the art would understand that in some specific instances, an embodiment can be alternatively described using language "consisting essentially of" or "consisting of."

Unless defined otherwise, all technical and scientific terms used herein have the same meaning as commonly understood to one of ordinary skill in the art to which this disclosure belongs. Although any methods and reagents similar or equivalent to those described herein can be used in the practice of the disclosed methods and compositions, the exemplary methods and materials are now described.

All publications mentioned herein are incorporated herein by reference in full for the purpose of describing and disclosing the methodologies, which are described in the publications, which might be used in connection with the description herein. All patents and publications mentioned in the specification are indicative of the levels of those of ordinary skill in the art to which the invention pertains prior to the filing date of the disclosure. Nothing herein is to be construed as an admission that the inventors are not entitled to antedate such disclosure by virtue of prior disclosure.

It will be readily apparent to a person skilled in the art that varying substitutions and modifications may be made to the invention disclosed herein without departing from the scope and spirit of the invention.

The invention illustratively described herein suitably may be practiced in the absence of any element or elements, limitation or limitations which is not specifically disclosed herein. Thus, for example, in each instance herein any of the terms "comprising", "consisting essentially of" and "consisting of" may be replaced with either of the other two terms. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

Other embodiments are set forth within the following claims.

What is claimed is:

1. A monoclonal antibody or antigen binding fragment thereof which specifically binds human CCL14, wherein the antibody or antigen binding fragment thereof comprises a heavy chain variable region comprising a CDR1, CDR2, and CDR3 sequence from SEQ ID NO: 19, and a light chain variable region comprising a CDR1, CDR2, and CDR3 sequence from SEQ ID NO: 20 (31H1/31K1).

2. The monoclonal antibody or antigen binding fragment thereof of claim 1, wherein the antibody comprises a heavy chain variable region of SEQ ID NO: 19 or a corresponding heavy chain variable region having at least 90% sequence similarity to the framework region thereof, and a light chain variable region of SEQ ID NO: 20 or a corresponding light chain variable region having at least 90% sequence similarity to the framework region thereof (31H1/31K1).

3. The monoclonal antibody or antigen binding fragment thereof of claim 1, wherein the monoclonal antibody or antigen binding fragment thereof (a) is conjugated to a signal development element;

(b) is immobilized on a solid support;

(c) is an F(ab) or F(ab')2 fragment; or (d) is a rabbit antibody or an antigen binding fragment thereof.

4. A kit comprising:

a first monoclonal antibody or antigen binding fragment thereof that is the monoclonal antibody or antigen binding fragment of claim 1, and a second monoclonal antibody or antigen binding fragment thereof which specifically binds human CCL14, wherein the first antibody or antigen binding fragment thereof and the second antibody or antigen binding fragment thereof form sandwich complexes with human CCL14.

5. The kit of claim 4, wherein the second antibody or antigen binding fragment is a monoclonal antibody or antigen binding fragment that is different from the first monoclonal antibody or antigen binding fragment.

6. The kit of claim 4, further comprising a disposable test device configured to generate a detectable signal related to the presence or amount of human CCL14 in a biological sample, wherein the first monoclonal antibody or antigen binding fragment thereof or the second monoclonal antibody or antigen binding fragment thereof is immobilized on a surface within the disposable test device.

7. The kit of claim 6, wherein the disposable test device is a lateral flow test device.

8. The kit of claim 6, wherein (a) the first monoclonal antibody or antigen binding fragment thereof is immobilized to a surface within the disposable test device, and the second monoclonal antibody or antigen binding fragment thereof is conjugated to a detectable label;

(b) the first monoclonal antibody or antigen binding fragment thereof is immobilized to a surface within the disposable test device, and the second monoclonal antibody or antigen binding fragment thereof is conjugated to a detectable label and is provided in a separate container from the disposable test device;

(c) the kit is configured to perform an assay method which provides a signal related to the presence or amount of human CCL14 in a biological sample, and wherein the minimum detectable concentration of CCL14 in the assay method is 10 ng/ml or less;

(d) one or both of the first or second monoclonal antibodies or antigen binding fragment thereof is an F(ab) or F(ab')2 fragment;

(e) one or both of the first or second monoclonal antibodies or antigen binding fragment thereof is a rabbit antibody or an antigen binding fragment thereof; or (f) the first and second monoclonal antibodies or antigen binding fragments thereof in the kit are a 31H1/31K1-10H3/10K1 pair, or a corresponding antigen binding fragment thereof, wherein 10H3/10K1 comprises three CDRs of a heavy chain variable region comprising the amino acid sequence of SEQ ID NO: 7, and three CDRs of a light chain variable region comprising the amino acid sequence of SEQ ID NO: 8.

9. The kit of claim 6, wherein the kit further comprises a calibration to relate the detectable signal to a concentration of CCL14.

10. The kit of claim 9, wherein the calibration is a calibration curve provided on an electronic memory device.

11. A method for determining the presence or amount of human CCL14 in a biological sample, comprising:

performing an immunoassay on the biological sample with a first monoclonal antibody or antigen binding fragment thereof and a second monoclonal antibody or antigen binding fragment thereof which together form sandwich complexes with human CCL14, wherein the immunoassay provides a detectable signal that is related to the presence or amount of human CCL14 in the biological sample bound in the sandwich complexes; and relating the detectable signal to the presence or amount of human CCL14 in the biological sample, wherein the first monoclonal antibody or antigen binding fragment thereof is the monoclonal antibody or fragment thereof of claim 1.

12. The method of claim 11, wherein (a) the minimum detectable concentration of CCL14 in the immunoassay is 10 ng/ml or less;

(b) the immunoassay is performed in a lateral flow format;

(c) the immunoassay is an in vitro diagnostic; or (d) the immunoassay is performed by applying the biological sample to a disposable test device, and the detectable signal is obtained by inserting the disposable test device into an analytical instrument, wherein the sandwich complexes comprising the first and second monoclonal antibodies or antigen binding fragments thereof are immobilized for detection in a predetermined zone of the disposable test device, and wherein the analytical instrument detects the immobilized sandwich complexes to provide the detectable signal.

13. The method of claim 11, wherein (a) the first monoclonal antibody or antigen binding fragment thereof is conjugated to a signal development element;

(b) the first monoclonal antibody or antigen binding fragment thereof forms a reaction mixture with the biological sample, and the biological sample is applied to the disposable test device by applying the reaction mixture to the disposable test device;

(c) the second monoclonal antibody or antigen binding fragment thereof is immobilized at the predetermined zone of a solid support;

(d) each of the first and second monoclonal antibodies or antigen binding fragments thereof is a rabbit, mouse, chicken, goat, sheep, donkey, human, llama or camelid antibody or antigen binding fragment thereof;

(e) at least one of the first and second monoclonal antibodies or antigen binding fragment thereof is a rabbit antibody or antibody fragment;

(f) one or both of the first or second monoclonal antibodies or antigen binding fragment thereof is an F(ab) or F(ab')2 fragment;

(g) the second monoclonal antibody or antigen binding fragment thereof forms a sandwich complex with CCL14 and the first monoclonal antibody or antigen binding fragment thereof; or (h) the first and second monoclonal antibodies or antigen binding fragments thereof are a 31H1/31K1-10H3/10K1 pair, or a corresponding antigen binding fragment thereof, wherein 10H3/10K1 comprises three CDRs of a heavy chain variable region comprising the amino acid sequence of SEQ ID NO: 7, and three CDRs of a light chain variable region comprising the amino acid sequence of SEQ ID NO: 8.

14. A method for determining the presence or amount of human CCL14 in a biological sample, comprising:

performing an immunoassay on the biological sample with a monoclonal antibody or antigen binding fragment thereof which binds human CCL14, wherein the immunoassay provides a detectable signal that is related to the presence or amount of human CCL14 in the biological sample; and relating the detectable signal to the presence or amount of human CCL14 in the biological sample, wherein the assay is a competitive assay and the monoclonal antibody or antigen binding fragment thereof is the monoclonal antibody or an antigen binding fragment thereof of claim 1.

15. A monoclonal antibody or antigen binding fragment thereof comprising a heavy chain variable region comprising a CDR1, CDR2, and CDR3 sequence from SEQ ID NO: 19, and a light chain variable region comprising a CDR1, CDR2, and CDR3 sequence from SEQ ID NO: 20 (31H1/ 31K1), wherein the heavy chain variable region has at least 90% sequence similarity within the framework sequences to the framework sequences of SEQ ID NO: 19, and the light chain variable region has at least 90% sequence similarity within the framework sequences to the framework sequences of SEQ ID NO: 20.

\* \* \* \* \*

SEQUENCE LISTING

Sequence total quantity: 31
SEQ ID NO: 1               moltype = AA  length = 142
FEATURE                    Location/Qualifiers -continued

```
REGION                   1..142
                         note = MISC_FEATURE - 2H3 heavy chain variable region
                           sequence
source                   1..142
                         mol_type = protein
                         organism = Oryctolagus cuniculus
SEQUENCE: 1
METGLRWLLL VAVLKGVQCQ EQLKESGGGL VQPGGSLKLS CKASGFAFSS DYMSWVRQAP  60
GKGLEWIGYI DPIFGSTAYA SWVNGRFTIS SHNAQNTLYL HLNSLTAADT ATYFCARDKD  120
YSSGWGGYFN LWGQGTLVTV SS                                           142

SEQ ID NO: 2             moltype = AA   length = 136
FEATURE                  Location/Qualifiers
REGION                   1..136
                         note = MISC_FEATURE - 2K1 light chain variable region
                           sequence
source                   1..136
                         mol_type = protein
                         organism = Oryctolagus cuniculus
SEQUENCE: 2
MDTRAPTQLL GLLLLWLPGA RCGAIVMTQT PASVEAAVGG TVTIKCQASQ SINSYLAWYQ  60
QKPGQPPRLL IYEASTLASG VPSRFKGSGS GTQFTLTISD LECADAATYY CQTYYYSVDS  120
SVGSNAFGGG TEVVVK                                                  136

SEQ ID NO: 3             moltype = AA   length = 138
FEATURE                  Location/Qualifiers
REGION                   1..138
                         note = MISC_FEATURE - 3H1 heavy chain variable region
                           sequence
source                   1..138
                         mol_type = protein
                         organism = Oryctolagus cuniculus
SEQUENCE: 3
METGLRWLLL VAVLKGVQCQ SVRESEGGLF KPADTLTLTC TVSGFSLSSD AISWVRQAPG  60
NGLEWIGAID FGGSAYYASW AKSRSTITRN TNENTVTLKM TSLTAADTAT YFCARSPSFG  120
IVDRLDLWGQ GTLVTVSS                                                138

SEQ ID NO: 4             moltype = AA   length = 136
FEATURE                  Location/Qualifiers
REGION                   1..136
                         note = MISC_FEATURE - 3K1 light chain variable region
                           sequence
source                   1..136
                         mol_type = protein
                         organism = Oryctolagus cuniculus
SEQUENCE: 4
MDTRAPTQLL GLLLLWLPGA RCAVVLTQTA SPVSAPVGGT VTIKCQASED IDSYLAWYQQ  60
KPGQPPKLLI YDVFDLSSGV PSRFKGSGSG TEFTLTISDL ECADAATYYC QSYYYVLGTT  120
STDHNSFGGG TEVVVK                                                  136

SEQ ID NO: 5             moltype = AA   length = 139
FEATURE                  Location/Qualifiers
REGION                   1..139
                         note = MISC_FEATURE - 4H1 heavy chain variable region
                           sequence
source                   1..139
                         mol_type = protein
                         organism = Oryctolagus cuniculus
SEQUENCE: 5
METGLRWLLL VAVLKGVQCQ SVKESEGGLF KPADTLTLTC TVSGFSLSSF AINWVRQAPG  60
EGLEYIGWIS DVGTAYYASW AKSRSTITRN TDENTATLKM TSLTAADTAT YFCAGGDGSY  120
SNYWVSDIWG QGTLVTVSS                                               139

SEQ ID NO: 6             moltype = AA   length = 128
FEATURE                  Location/Qualifiers
REGION                   1..128
                         note = MISC_FEATURE - 4K3 light chain variable region
                           sequence
source                   1..128
                         mol_type = protein
                         organism = Oryctolagus cuniculus
SEQUENCE: 6
MDTRAPTQLL GLLLLWLPGA RCAVVLTQTA SPVSAPVGGT VTVKCQASQT INNRLAWYQQ  60
KQGQPPKLLI YEASKLASGV PSRFKGSGSG TEYTLTIRGV ECADAATYSC QEYADENIFG  120
GGTEVVVK                                                          128
```

-continued

```
SEQ ID NO: 7                moltype = AA  length = 139
FEATURE                     Location/Qualifiers
REGION                      1..139
                            note = MISC_FEATURE - 10H3 heavy chain variable region
                             sequence
source                      1..139
                            mol_type = protein
                            organism = Oryctolagus cuniculus
SEQUENCE: 7
METGLRWLLL VAVLKGVQCQ SVKESEGGLF KPADTLTLTC TVSGFSLSSY AINWVRQAPG  60
EGLEYIGWIS DVGTAYYASW AKSRSTITRN TDENTVTLKM TSLTAADTAT YFCAGGDGSY  120
SNYWVSDIWG QGTLVTVSS                                               139

SEQ ID NO: 8                moltype = AA  length = 128
FEATURE                     Location/Qualifiers
REGION                      1..128
                            note = MISC_FEATURE - 10K1 light chain variable region
                             sequence
source                      1..128
                            mol_type = protein
                            organism = Oryctolagus cuniculus
SEQUENCE: 8
MDTRAPTQLL GLLLLWLPGA RCAVVLTQTP SLVSAPVGGT VTVKCRASQT INSRLAWYQQ  60
KQGQPPKLLI YEASKLASGV PSRFKGSGSG TEYTLTIRGV ECADAATYSC QEYADENIFG  120
GGTEVVVK                                                           128

SEQ ID NO: 9                moltype = AA  length = 138
FEATURE                     Location/Qualifiers
REGION                      1..138
                            note = MISC_FEATURE - 12H2 heavy chain variable region
                             sequence
source                      1..138
                            mol_type = protein
                            organism = Oryctolagus cuniculus
SEQUENCE: 9
METGLRWLLL VAVLKGVQCQ SVRESEGGLF KPADTLTLTC TVSGFSLSSD AISWVRQAPG  60
NGLEWIGAID FGGSAYYASW AKSRSTITRN TNENTVTLKM TSLTAADTAT YFCARSPSFG  120
IVDRLDLWGQ GTLVTVSS                                                138

SEQ ID NO: 10               moltype = AA  length = 136
FEATURE                     Location/Qualifiers
REGION                      1..136
                            note = MISC_FEATURE - 12K1 light chain variable region
                             sequence
source                      1..136
                            mol_type = protein
                            organism = Oryctolagus cuniculus
SEQUENCE: 10
MDTRAPTQLL GLLLLWLPGA RCAVVLTQTA SPVSAPVGGT VTIKCQASED IDSYLAWYQQ  60
KPGQPPKLLI YDVFDLSSGV PSRFKGSGSG TEFTLTISDL ECADAATYYC QSYYYVLGTT  120
STDHNSFGGG TEVVVK                                                  136

SEQ ID NO: 11               moltype = AA  length = 139
FEATURE                     Location/Qualifiers
REGION                      1..139
                            note = MISC_FEATURE - 17H2 heavy chain variable region
                             sequence
source                      1..139
                            mol_type = protein
                            organism = Oryctolagus cuniculus
SEQUENCE: 11
METGLRWLLL VAVLKGVQCQ SVKESEGGLF KPADTLTLTC TVSGFSLSSY AINWVRQAPG  60
EGLEYIGWIS DVGTAYYASW AKSRSTITRN TDENTVTLKM TSLTAADTAT YFCAGGDGSY  120
SNYWVSDIWG QGTLVTVSS                                               139

SEQ ID NO: 12               moltype = AA  length = 128
FEATURE                     Location/Qualifiers
REGION                      1..128
                            note = MISC_FEATURE - 17K1 light chain variable region
                             sequence
source                      1..128
                            mol_type = protein
                            organism = Oryctolagus cuniculus
SEQUENCE: 12
MDTRAPTQLL GLLLLWLPGA RCAVVLTQTA SPVSAPVGGT VTVKCQASQT INSRLAWYQQ  60
KQGQPPKLLI YEASTLASGV PSRFKGSGSG TEYTLTIRGV ECADAATYSC QEYADENIFG  120
GGTEVVVK                                                           128
```

```
SEQ ID NO: 13            moltype = AA   length = 139
FEATURE                  Location/Qualifiers
REGION                   1..139
                         note = MISC_FEATURE - 18H1 heavy chain variable region
                          sequence
source                   1..139
                         mol_type = protein
                         organism = Oryctolagus cuniculus
SEQUENCE: 13
METGLRWLLL VAVLKGVQCQ SVKESEGGLF KPADTLTLTC TVSGFSLSSY AINWVRQAPG  60
EGLEYIGWIS DVGTAYYASW AKSRSTITRN TDENTVTLKM TSLTAADTAT YFCAGGDGSY  120
SNYWVSDIWG QGTLVTVSS                                               139

SEQ ID NO: 14            moltype = AA   length = 128
FEATURE                  Location/Qualifiers
REGION                   1..128
                         note = MISC_FEATURE - 18K1 light chain variable region
                          sequence
source                   1..128
                         mol_type = protein
                         organism = Oryctolagus cuniculus
SEQUENCE: 14
MDTRAPTQLL GLLLLWLPGA RCAVVLTQTA SPVSAPVGGT VTVKCQASQT INSRLAWYQQ  60
KQGQPPKLLI YEASTLASGV PSRFKGSGSG TEYTLTIRGV ECADAATYSC QEYADENIFG  120
GGTEVVVK                                                           128

SEQ ID NO: 15            moltype = AA   length = 139
FEATURE                  Location/Qualifiers
REGION                   1..139
                         note = MISC_FEATURE - 19H2 heavy chain variable region
                          sequence
source                   1..139
                         mol_type = protein
                         organism = Oryctolagus cuniculus
SEQUENCE: 15
METGLRWLLL VAVLKGVQCQ SVKESEGGLF KPADTLTLTC TVSGFSLSSF AINWVRQAPG  60
EGLEYIGWIS DVGTAYYASW AKSRSTITRN ADENTVTLKM TSLTAADTAT YFCAGGDGSY  120
SNYWVSDIWG QGTLVTVSS                                               139

SEQ ID NO: 16            moltype = AA   length = 128
FEATURE                  Location/Qualifiers
REGION                   1..128
                         note = MISC_FEATURE - 19K3 light chain variable region
                          sequence
source                   1..128
                         mol_type = protein
                         organism = Oryctolagus cuniculus
SEQUENCE: 16
MDTRAPTQLL GLLLLWLPGA RCAVVLTQTA SPVSAPVGGT VTVKCQASQT INNRLAWYQQ  60
KQGQPPKLLI YEASKLASGV PSRFKGSGSG TEYTLTIRGV ECADAATYSC QEYADENIFG  120
GGTEVVVK                                                           128

SEQ ID NO: 17            moltype = AA   length = 140
FEATURE                  Location/Qualifiers
REGION                   1..140
                         note = MISC_FEATURE - 25H2 heavy chain variable region
                          sequence
source                   1..140
                         mol_type = protein
                         organism = Oryctolagus cuniculus
SEQUENCE: 17
METGLRWLLL VAVLKGVQCQ SLEESGGDLV KPGASLTLTC TASRFDFSSA YYMCWVRQAP  60
GKGLEWIACI YAGSSGGTYY ATWAKGRFTI SKTSSTTVTL QLTSLTAADT ATYFCAGSTG  120
NSRGSYFNLW GQGTLVTVSS                                              140

SEQ ID NO: 18            moltype = AA   length = 131
FEATURE                  Location/Qualifiers
REGION                   1..131
                         note = MISC_FEATURE - 25K1 light chain variable region
                          sequence
source                   1..131
                         mol_type = protein
                         organism = Oryctolagus cuniculus
SEQUENCE: 18
MDTRAPTQLL GLLLLWLPGA TFAQVLTQTP SPVSAAVGGT VTINCQSSQS VYDNNWLAWY  60
QQKLGQPPKL VIYDASKLAS GVPSRFKGSG SGTHFTLTIS ELQCDDSATY YCQGEYSDIW  120
GFGGGTEVVV K                                                       131
```

```
SEQ ID NO: 19              moltype = AA   length = 138
FEATURE                    Location/Qualifiers
REGION                     1..138
                           note = MISC_FEATURE - 31H1 heavy chain variable region
                            sequence
source                     1..138
                           mol_type = protein
                           organism = Oryctolagus cuniculus
SEQUENCE: 19
METGLRWLLL VAVLKGVQCQ SVRESEGGLF KPADTLTLTC TVSGFSLSSD AISWVRQAPG  60
NGLEWIGAID FGGSAYYASW AKSRSTITRN TNENTVTLKM TSLTAADTAT YFCARSPSFG  120
IVDRLDLWGQ GTLVTVSS                                                138

SEQ ID NO: 20              moltype = AA   length = 136
FEATURE                    Location/Qualifiers
REGION                     1..136
                           note = MISC_FEATURE - 31K1 light chain variable region
                            sequence
source                     1..136
                           mol_type = protein
                           organism = Oryctolagus cuniculus
SEQUENCE: 20
MDTRAPTQLL GLLLLWLPGA KCAVVLTQTA SPVSAPVGGT VTIKCQASED IDSYLAWYQQ  60
KPGQPPKLLI YDVFDLSSGV PSRFKGSGSG TEFTLTISDL ECADAATYYC QSYYVLGTT  120
STDHNSFGGG TEVVVK                                                  136

SEQ ID NO: 21              moltype = AA   length = 93
FEATURE                    Location/Qualifiers
source                     1..93
                           mol_type = protein
                           organism = Homo sapiens
SEQUENCE: 21
MKISVAAIPF FLLITIALGT KTESSSRGPY HPSECCFTYT TYKIPRQRIM DYYETNSQCS  60
KPGIVFITKR GHSVCTNPSD KWVQDYIKDM KEN                               93

SEQ ID NO: 22              moltype = AA   length = 17
FEATURE                    Location/Qualifiers
source                     1..17
                           mol_type = protein
                           organism = Homo sapiens
SEQUENCE: 22
QTGGKPKVVK IQLKLVG                                                 17

SEQ ID NO: 23              moltype = AA   length = 16
FEATURE                    Location/Qualifiers
REGION                     1..16
                           note = MISC_FEATURE - 10H3/10K1 epitope sequence
source                     1..16
                           mol_type = protein
                           organism = Homo sapiens
SEQUENCE: 23
HSVCTNPSDK WVQDYI                                                  16

SEQ ID NO: 24              moltype = AA   length = 14
FEATURE                    Location/Qualifiers
REGION                     1..14
                           note = MISC_FEATURE - 31H1/31K1 epitope sequence
source                     1..14
                           mol_type = protein
                           organism = Homo sapiens
SEQUENCE: 24
CCFTYTTYKI PRQR                                                    14

SEQ ID NO: 25              moltype = AA   length = 12
FEATURE                    Location/Qualifiers
REGION                     1..12
                           note = MISC_FEATURE - 25H2/25K1 epitope sequence 1
source                     1..12
                           mol_type = protein
                           organism = Homo sapiens
SEQUENCE: 25
DKWVQDYIKD MK                                                      12

SEQ ID NO: 26              moltype = AA   length = 12
FEATURE                    Location/Qualifiers
REGION                     1..12
                           note = MISC_FEATURE - 25H2/25K1 epitope sequence 2
```

-continued

```
source                    1..12
                          mol_type = protein
                          organism = Homo sapiens
SEQUENCE: 26
MDYYETNSQC SK                                                          12

SEQ ID NO: 27             moltype = AA   length = 13
FEATURE                   Location/Qualifiers
REGION                    1..13
                          note = MISC_FEATURE - 2H3/2K1 epitope 1
source                    1..13
                          mol_type = protein
                          organism = Homo sapiens
SEQUENCE: 27
ECCFTYTTYK IPR                                                         13

SEQ ID NO: 28             moltype = AA   length = 9
FEATURE                   Location/Qualifiers
REGION                    1..9
                          note = MISC_FEATURE - 2H3/2K1 epitope 2
source                    1..9
                          mol_type = protein
                          organism = Homo sapiens
SEQUENCE: 28
TNSQCSKPG                                                              9

SEQ ID NO: 29             moltype = AA   length = 9
FEATURE                   Location/Qualifiers
REGION                    1..9
                          note = MISC_FEATURE - 19H2/19K3 epitope
source                    1..9
                          mol_type = protein
                          organism = Homo sapiens
SEQUENCE: 29
ETNSQCSKP                                                              9

SEQ ID NO: 30             moltype = AA   length = 14
FEATURE                   Location/Qualifiers
REGION                    1..14
                          note = MISC_FEATURE - AF324 epitope sequence 1
source                    1..14
                          mol_type = protein
                          organism = Homo sapiens
SEQUENCE: 30
KTESSSRGPY HPSE                                                        14

SEQ ID NO: 31             moltype = AA   length = 12
FEATURE                   Location/Qualifiers
REGION                    1..12
                          note = MISC_FEATURE - AF324 epitope sequence 2
source                    1..12
                          mol_type = protein
                          organism = Homo sapiens
SEQUENCE: 31
YTTYKIPRQR IM                                                         12
```